US012766166B2

(12) United States Patent
Traweger et al.

(10) Patent No.: US 12,766,166 B2
(45) Date of Patent: Oct. 20, 2026

(54) MESENCHYMAL STEM CELL-DERIVED EXTRACELLULAR VESICLES AND THEIR MEDICAL USE

(71) Applicant: PARACELSUS MEDIZINISCHE PRIVATUNIVERSITÄT SALZBURG—PRIVATSTIFTUNG, Salzburg (AT)

(72) Inventors: Andreas Traweger, Bürmoos (AT); Mario Gimona, Anif (AT)

(73) Assignee: PARACELSUS MEDIZINISCHE PRIVATUNIVERSITÄT SALZBURG—PRIVATSTIFTUNG, Salzburg (AT)

( * ) Notice: Subject to any disclaimer, the term of this patent is extended or adjusted under 35 U.S.C. 154(b) by 1108 days.

(21) Appl. No.: 16/475,154

(22) PCT Filed: Jan. 10, 2018

(86) PCT No.: PCT/EP2018/050536
§ 371 (c)(1),
(2) Date: Jul. 1, 2019

(87) PCT Pub. No.: WO2018/130554
PCT Pub. Date: Jul. 19, 2018

(65) Prior Publication Data

US 2019/0328792 A1 Oct. 31, 2019

(30) Foreign Application Priority Data

Jan. 11, 2017 (EP) .................................... 17151040

(51) Int. Cl.
*A61K 35/28* (2015.01)
*A61K 38/18* (2006.01)
(Continued)

(52) U.S. Cl.
CPC .......... *A61K 35/28* (2013.01); *A61K 38/1841* (2013.01); *A61P 19/08* (2018.01);
(Continued)

(58) Field of Classification Search
CPC ........ C12N 5/0062–0669; A61K 35/28; A61K 38/1875; A61P 19/00–10
See application file for complete search history.

(56) References Cited

U.S. PATENT DOCUMENTS 5,106,748 A 4/1992 Wozney et al.
5,658,882 A 8/1997 Celeste et al.
(Continued)

FOREIGN PATENT DOCUMENTS

WO WO-9639170 A1 * 12/1996 ......... A61K 38/1875
WO 2010111522 A2 9/2010
(Continued)

OTHER PUBLICATIONS

Pachler, K. et al "A good manufacturing practice-grade standard protocol . . . " Cytother., vol. 19, pp. 458-472. (Year: 2017).*
(Continued)

*Primary Examiner* — Scarlett Y Goon
*Assistant Examiner* — Audrey L Buttice

(57) ABSTRACT

The present invention relates to a method for obtaining extracellular vesicles derived from mesenchymal stromal cells (MSCs), wherein the extracellular-vesicles are essentially free of vesicles not derived from the MSCs, and wherein the extracellular-vesicles are essentially free of heparin. The invention further relates to the extracellular vesicles derived from mesenchymal stromal cells (MSCs), to a pharmaceutical composition comprising such extracellular-vesicles and to the use of the pharmaceutical composition in the treatment of (a) bone defect(s), tendon defect(s) and/or spinal cord injury. The pharmaceutical composition
(Continued)

Figure 2:
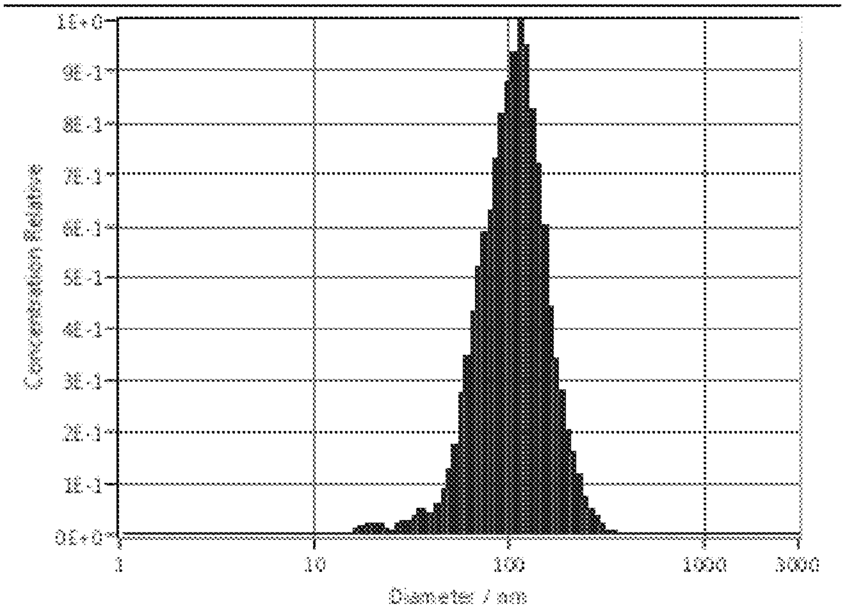
Figure 2:
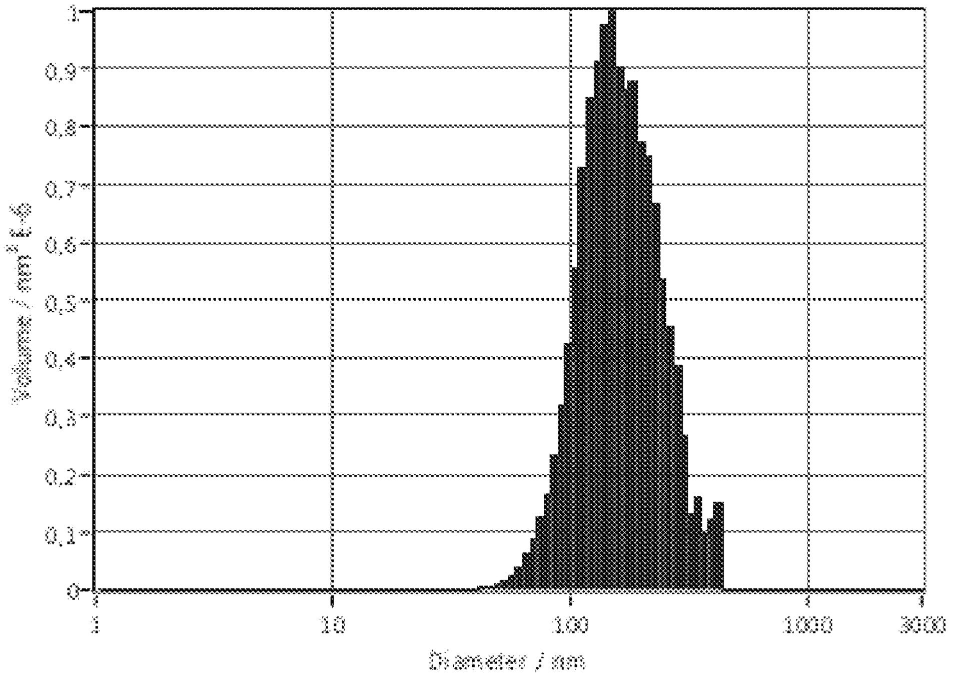
Figure 2:
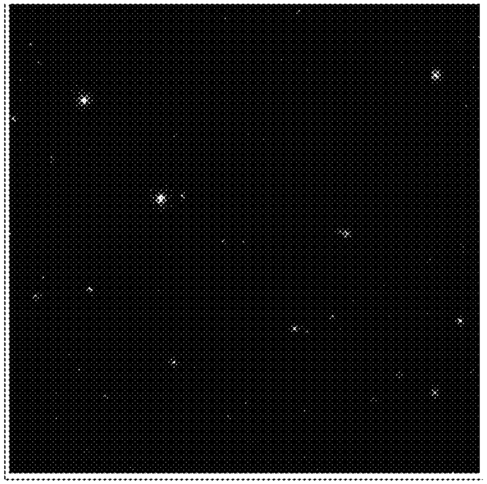

of the invention can further comprise one or more Bone Morphogenic Proteins (BMPs), such as BMP2.

5 Claims, 34 Drawing Sheets

(51) Int. Cl.

| | |
|---|---|
| ***A61K 39/00*** | (2006.01) |
| ***A61K 47/69*** | (2017.01) |
| ***A61P 19/08*** | (2006.01) |
| ***A61P 25/00*** | (2006.01) |
| ***C07K 14/49*** | (2006.01) |
| ***C07K 14/51*** | (2006.01) |
| ***C12N 5/0775*** | (2010.01) |
| ***C12N 15/11*** | (2006.01) |
| ***C12N 15/113*** | (2010.01) |

(52) U.S. Cl.

CPC .............. *A61P 25/00* (2018.01); *C07K 14/49* (2013.01); *C07K 14/51* (2013.01); *C12N 5/0663* (2013.01); *C12N 15/111* (2013.01); *C12N 15/113* (2013.01); *C12N 15/1136* (2013.01); *A61K 2039/55555* (2013.01); *A61K 47/6903* (2017.08); *C12N 2310/141* (2013.01); *C12N 2320/30* (2013.01); *C12N 2502/00* (2013.01)

(56) References Cited

U.S. PATENT DOCUMENTS

| | | | | |
|---|---|---|---|---|
| 6,620,406 | B1 * | 9/2003 | Wozney ............. | A61K 38/1875 424/49 |
| 2015/0045298 | A1 | 2/2015 | Bang et al. | |
| 2016/0184363 | A1 | 6/2016 | Badiavas et al. | |

FOREIGN PATENT DOCUMENTS

| | | | | |
|---|---|---|---|---|
| WO | 2012087241 | A1 | 6/2012 | |
| WO | 2013121426 | A1 | 8/2013 | |
| WO | WO-2014044894 | A1 * | 3/2014 | ........... A61K 9/5153 |
| WO | 2015179227 | A1 | 11/2015 | |
| WO | 2016082882 | A2 | 6/2016 | |

OTHER PUBLICATIONS

Sun, L. et al “Safety evaluation of exosomes derived from human umbilical cord . . . ” Cytother., vol. 18, pp. 413-422. (Year: 2016).*
Teng, X et al “Mesenchymal stem cell-derived exosomes . . . ” Cell. Physiol. Biochem., vol. 37, No. 6, pp. 2415-2424. (Year: 2015).*
Shelke, G. et al “Importance of exosome depletion protocols . . . ” J. Extracellular Vesicles, vol. 3, pp. 1-8. (Year: 2014).*
Malda, J. et al “Extracellular vesicles: new tool for joint repair . . . ” Nat. Rev. Rheumatol., vo 12, pp. 243-249. (Year: 2016).*
Machine translation of WO 2014/044894. (Year: 2014).*
Zhang, J. et al “Exosomes/tricalcium phosphate combination scaffolds . . . ” Stem Cell Res. Ther., vol. 7, pp. 1-14. (Year: 2016).*
Nazirkar, G. et al “Effortless Effort in bone regeneration . . . ” J. Intl. Oral Health, vol. 6, No. 3, pp. 120-124. (Year: 2014).*
Jin, L. et al “Growth differentiation factor 5 regulation . . . ” Curr. Pharm. Design, vol. 19, pp. 3364-3373. (Year: 2013).*
Deluca, A. et al “Synergistic effect of umbilical cord extracellular vesicles . . . ” Stem Cell Res. Ther., vol. 15, No. 144, pp. 1-12. (Year: 2024).*
Hemeda, H. et al “Heparin concentration is critical for cell culture with human platelet lysate” Cytother., vol. 15, pp. 1174-1181. (Year: 2013).*
Ho, S.S., et al (2016) Bone morphogenetic protein-2 promotes human mesenchymal stem cell survival and resultant bone formation when entrapped in photocrosslinked alginate hydrogels Adv Healthc Mater 5(19); 2501-2509 (Year: 2016).*
Keerthikumar, S. et al (2015) Proteogenomic analysis reveals exosomes are more ocogenic than ectosomes Oncotarget 6(17); 15375-15396 (Year: 2015).*
Dominici, M., et al (2006) Minimal criteria for defining multipotent mesenchymal stromal cells. The international society for cellular therapy position statement Cytotherapy 8(4) 315-317 (Year: 2006).*
Zaunschirm-Strutz, J., et al (2025) MicroRNA profiling in umbilical cord plasma: links to maternal metabolism and neonatal metabolic and inflammatory traits J. Physiol 603.6; 1663-1680 (Year: 2025).*
Wang, X., et al (2026) Investigating the therapeutic efficacy of quality-controlled, miR-146a-5p-enriched small extracellular vesicles derived from MSCs against Idiopathic pulmonary fibrosis Stem cell reviews and reports 22; 523-544 (Year: 2026).*
The English translation of the International Search Report, mailed on Jun. 19, 2018, in the corresponding PCT Appl. No. PCT/EP2018/050536.
Tetta Ciro et al: “The role of microvesicles derived from mesenchymal stem cells in tissue regeneration; a dream for tendon repair?”, Muscles, Ligaments and Tendons Journal Jul. 2012, vol. 2, No. 3, Jul. 2012 (Jul. 2012), pp. 212-221, XP002779497.
Nina Heldring et al: “Therapeutic Potential of Multipotent Mesenchymal Stromal Cells and Their Extracellular Vesicles”, Human Gene Therapy, vol. 26, No. 8, Aug. 1, 2015 (Aug. 1, 2015), pp. 506-517, XP055398495.
Ruiz Maxime et al: “Therapeutic application of mesenchymal stem cells in osteoarthritis.”, Expert Opinion on Biological Therapy 2016, vol. 16, No. 1, 2016, pp. 33-42, XP002779498.
Furuta Taisuke et al: “Mesenchymal Stem Cell-Derived Exosomes Promote Fracture Healing in a Mouse Model.”, Stem Cells Translational Medicine 12 2016, vol. 5, No. 12, Dec. 2016 (Dec. 2016), pp. 1620-1630, XP002779499.

* cited by examiner

Figure 1

| Positive marker miRNAs | Range |
|---|---|
| hsa-miR-146a-5p | 80 -100% |
| hsa-miR-92a-3p | > 50% |
| hsa-miR-21-5p | > 15% |
| hsa-miR-221-3p | > 15% |
| hsa-miR-148a-3p | > 10% |
| hsa-let-7i-5p | > 5% |
| hsa-let-7f-5p | > 5% |

| Negative marker miRNAs | |
|---|---|
| hsa-miR-133 | < 0,1% |
| hsa-miR-135 | < 0,1% |
| hsa-miR-204 | < 0,1% |
| hsa-miR-211 | < 0,1% |
| hsa-miR-17 | < 0,1% |
| hsa-miR-106 | < 0,1% |

ZETAVIEW PARTICLEMETRIX
www.particle-metrix.de

Electrophoresis & Brownian Motion
Video Analysis
Laser Scattering Microscopy

Operator (Report): ZetaView
Video Operator: ZetaView

Sample Parameters
Sample Name: EV UCMSC LA0013-1,Hep-med (02.11.16) [5-200nm] (1)
Comment: Operator: AD, test. T=20,0°C CA0087
Electrolyte: PBS, Concentration: 0,000 N
Temperature: 18,87 °C sensed
pH 7,0 entered
Conductivity: 14523,81 µS/cm sensed

Result (sizes in nm)

| | Number | Concentration | Volume |
|---|---|---|---|
| Median (X50) | 101,6 | 101,6 | 149,1 |
| Span | 43,4 | 43,4 | 65,3 |

Concentration: 4,8E+7 Particles / mL
Dilution Factor: 700
Original Concentration: 3,4E+10 Particles / cm³

Quality
Average Counted Particles per Frame: 120
Number of Traced Particles: 646

Measurement Parameters
Cell S/N: CA0012-0114b

Measurement Mode: Size Distribution 2 Cycles
11 Positions, 2 Removed for Analysis

Analysis Parameters
Max Size: 200, Min Size: 5, Min Brightness: 20

Figure 2

Peak Analysis (Concentration)

| Diameter / nm | Particles/mL | FWHM / nm | Percentage |
|---|---|---|---|
| 108,8 | 3,6E+6 | 87,1 | 100,0 |

X Values

| | Number | Concentration | Volume |
|---|---|---|---|
| X10 | 60,6 | 60,6 | 95,7 |
| X50 | 101,6 | 101,6 | 149,1 |
| X90 | 158,1 | 158,1 | 245,3 |
| Span | 1,0 | 1,0 | 1,0 |
| Mean | 109,7 | 109,7 | 167,4 |
| StdDev | 43,4 | 43,4 | 65,3 |

Comment

(Signature)

Analyzed Video: D:\NTA Berichte\20161103_0006_EV UCMSC LA0013-1,Hep-med (02.11.16) [5-200nm]_size_000.avi ZetaVIEW S/N 197, Software ZetaView 8.02.31, Camera 0,703 µm/px Experiment: 2016-11-03 11:09, Report: 2016-11-03 11:11

A

B

B

C

C

D

E

A

B

C

C

D

E

F

G

H

I

J

EV from med. A (mean diameter: 0.126 μm)

EV from med. B (mean diameter: 0.126 μm)

EV from FBS med. (mean diameter: 0.124 μm)

| | 1 | 2 | 3 | 4 | 5 | 6 | 7 | 8 | 9 |
|---|---|---|---|---|---|---|---|---|---|
| Cell lysate (100 µg) | + | + | + | + | + | + | + | + | + |
| PK (37 °C, 30') | 0.05 µg/µl | 0.05 µg/µl | 0.05 µg/µl | 0.05 µg/µl | 0.5 µg/µl | 0.5 µg/µl | 0.5 µg/µl | 0.5 µg/µl | - 37 °C 30' |
| PMSF (RT, 10') | + | + | - | - | + | + | - | - | - RT °C 10' |
| 90 °C, 5' | + | - | + | - | + | - | + | - | + |

C

D

MESENCHYMAL STEM CELL-DERIVED EXTRACELLULAR VESICLES AND THEIR MEDICAL USE

This application is a National Stage Application of PCT/EP2018/050536 filed Jan. 10, 2018, which claims priority from European Patent Application No. 17151040.7, filed on Jan. 11, 2017. The priority of both said PCT and European Patent Application are claimed. Each of prior mentioned applications is hereby incorporated by reference herein in its entirety.

The present invention relates to a method for obtaining extracellular vesicles derived from mesenchymal stromal cells (MSCs), wherein the extracellular-vesicles are essentially free of vesicles not derived from the MSCs, and wherein the extracellular-vesicles are essentially free of heparin. The invention further relates to the extracellular vesicles derived from the mesenchymal stromal cells (MSCs), to a pharmaceutical composition comprising such extracellular-vesicles and to the use of the pharmaceutical composition in the treatment of (a) bone defect(s), tendon defect(s) and/or spinal cord injury. The pharmaceutical composition of the invention can further comprise one or more Bone Morphogenic Proteins (BMPs), such as BMP2.

Adult bone is effectively repaired after damage through an innate regenerative process, in most cases resulting in full restoration of a functional tissue with no apparent scar formation. However, around 10% of all fractures do not heal adequately and especially large osseous defects after trauma, prosthesis loosening, or tumor resection remains clinically challenging (Gomez-Barrena et al., 2011, Keramaris et al., 2008, and Steinmann et al., 1992). Currently, autologous iliac crest bone grafting represents the gold standard for treating large defects in the clinic. However, this procedure is often associated with donor site morbidity and the restricted availability of autologous bone tissue often limits its application. Therefore, the use of adult stem cells, alone or in combination with scaffold materials have gained substantial interest as an alternative treatment modality (Dawson et al., 2014). Adult mesenchymal stromal cells have been isolated from various tissues, including adipose (Lin et al., 2007), umbilical cord (Kim et al., 2004), periodontal ligament (Seo et al., 2004), articular cartilage (Dowthwaite et al., 2004), and tendon (Bi et al., 2007, Salingcarnboriboon et al., 2003, Tempfer et al., 2009, and Kunkel et al., 2015). Although most stromal cell fractions isolated from these tissues have been shown to exhibit osteo-chondro-adipogenic differentiation and share common stem cell-like characteristics, tissue-specific properties and hence potentially functional differences have been demonstrated (Yoshimura et al., 2007). Therefore, identifying alternative cell sources or osteoinductive cell-derived products to stimulate bone growth is highly desirable. Among the various cell types bone marrow stromal cells, referred to as mesenchymal stem cells (MSCs), are the most intensively studied and have already been used for therapeutic bone reconstruction in the clinic (Gomez-Barrena et al., 2011, Dawson et al., 2014, and Rosset et al., 2014). However, therapeutic efficacy has been minimal and the need for reliable, safe and effective therapies remains.

Accordingly, the technical problem underlying the present invention is the provision of an improved treatment of bone defects.

The technical problem is solved by provision of the embodiments provided herein below and as characterized in the appended claims.

The present invention relates to extracellular-vesicles derived from mesenchymal stromal cells (MSCs), wherein the extracellular-vesicles are essentially free of vesicles not derived from the MSCs, and wherein the extracellular-vesicles are essentially free of an anticoagulant (particularly heparin).

As documented herein below, the extracellular vesicles of the invention are essentially free of potential harmful components, such as anticoagulant (particularly heparin) and vesicles comprised in human platelet lysate or fetal bovine serum; see e.g. Example 2 and below. In addition, the extracellular vesicles of the invention demonstrate strong bone regeneration efficiency in an animal model; see e.g. Example 1 and below. Therefore, the extracellular vesicles are suitable for the advantageous treatment of, for example, bone defect(s); such as fractures; and/or tendon defect(s).

Accordingly, the present invention relates to a pharmaceutical composition for use in the treatment of (a) bone defect(s), tendon defect(s) and/or spinal cord injury, wherein the pharmaceutical composition comprises extracellular-vesicles derived from mesenchymal stromal cells (MSCs), wherein the extracellular-vesicles are essentially free of vesicles not derived from the MSCs, and wherein the extracellular-vesicles are essentially free of anticoagulant (particularly heparin).

The present invention further relates to a pharmaceutical composition comprising extracellular-vesicles derived from mesenchymal stromal cells (MSCs), wherein the extracellular-vesicles are essentially free of vesicles not derived from the MSCs, and wherein the extracellular-vesicles are essentially free of an anticoagulant (particularly heparin).

The present invention also relates to a method of treating (a) bone defect(s), tendon defect(s) and/or spinal cord injury, wherein the method comprises the administration of a pharmaceutical composition comprising extracellular-vesicles derived from mesenchymal stromal cells (MSCs), wherein the extracellular-vesicles are essentially free of vesicles not derived from the MSCs, and wherein the extracellular-vesicles are essentially free of an anticoagulant (particularly heparin).

The present invention also relates to a method for obtaining extracellular-vesicles derived from mesenchymal stromal cells (MSCs), wherein the method comprises:

(i) removing fibrinogen from the culture medium, wherein no anticoagulant (particularly heparin) is added to the culture medium, and removing vesicles from the culture medium,
(ii) culturing MSCs in the culture medium of step (i), and
(iii) isolating the extracellular-vesicles derived from the MSCs from the medium.

As documented herein and in the appended examples, it was surprisingly found that the extracellular vesicles of the invention can be obtained. Such extracellular-vesicles are released from MSCs, wherein the MSCs are cultured in culture medium that is essentially free of an anticoagulant (particularly heparin), fibrinogen and vesicles comprised in the culture medium, such as vesicles comprised in cell culture supplements, e.g., serum, plasma or platelet lysate; see illustrative Examples 1 and 2. Accordingly, the present invention relates to a method to obtain extracellular vesicles derived from MSCs, wherein the MSCs are cultured in a culture medium, wherein no anticoagulant (particularly heparin) is added to the culture medium, wherein fibrinogen is removed from the culture medium, and wherein vesicles occurring in the culture medium prior to the culturing of the MSCs are removed from the culture medium. The vesicles occurring in the culture medium prior to the culturing of the MSCs may comprise vesicles that occur in a serum (e.g. fetal bovine serum), plasma or platelet lysate (e.g., human platelet lysate). Such vesicles are herein referred to as vesicles not derived from MSCs. Accordingly, the obtained extracellular-vesicles derived from MSCs are essentially free of vesicles (that are) not derived from the MSCs and are essentially free of anticoagulant (particularly heparin), and preferably fibrinogen. Such extracellular vesicles derived from the MSCs and obtained by the methods of the invention are referred to extracellular vesicles of the invention.

Consequently, the herein provided methods and the obtained extracellular vesicles derived from MSCs are essentially free of anticoagulant (particularly heparin) and vesicles not derived from the MSCs, and optionally fibrinogen, that are comprised in the culture medium. Anticoagulant (particularly heparin), vesicles and fibrinogen comprised in the culture medium might result in adverse effects and thus should be avoided in therapeutic agents applied in clinics. Therefore, the methods and extracellular vesicles provided herein are advantageous.

The extracellular vesicles of the invention show particular characteristics as described in detail below and in the appended Examples. For instance, the miRNA profile and the levels of the miRNAs of the extracellular vesicles of the invention or the extracellular vesicles obtained by the methods of the invention was unexpectedly different compared to other preparations of extracellular vesicles derived from MSCs. For example, the extracellular vesicles purified in Baglio et al., 2015 showed a different miRNA profile and different miRNA abundances compared to the extracellular vesicles of the invention and the extracellular vesicles obtained by the methods of the invention (see below and the appended Examples). Therefore, the extracellular vesicles provided herein are different compared to the extracellular vesicles purified in e.g. Baglio et al. 2015.

Figure 9:
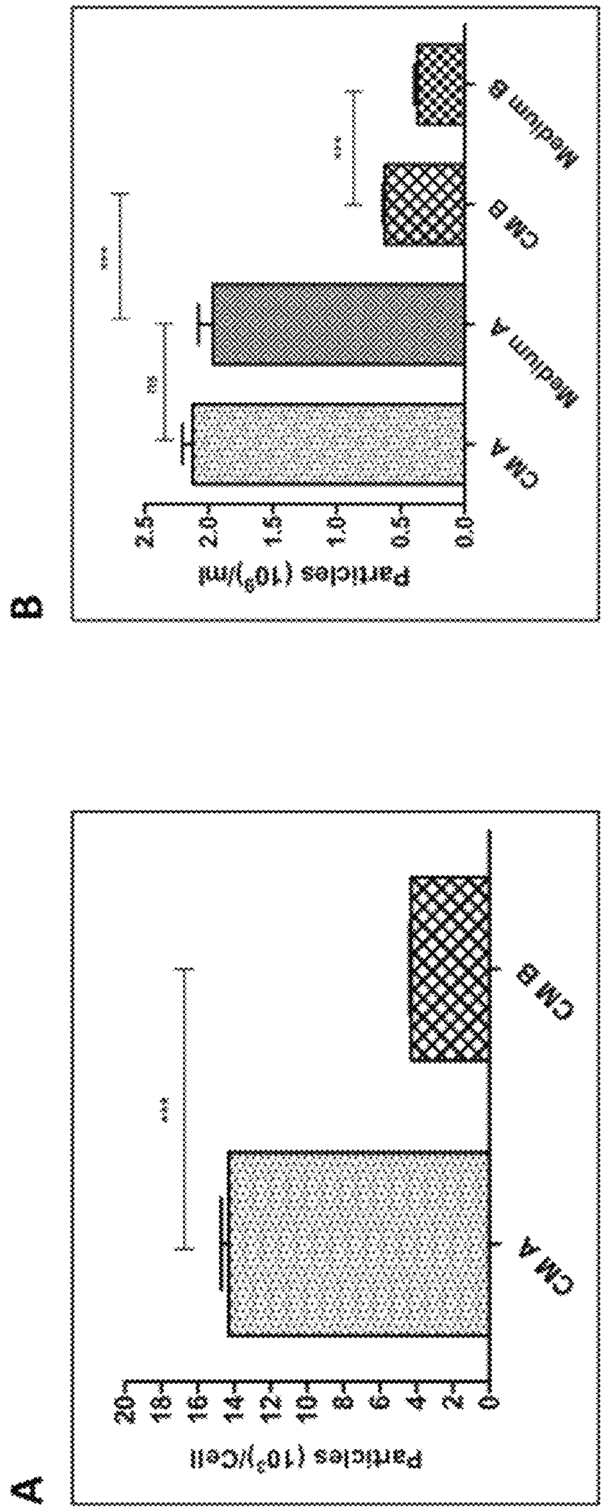
Figure 9:
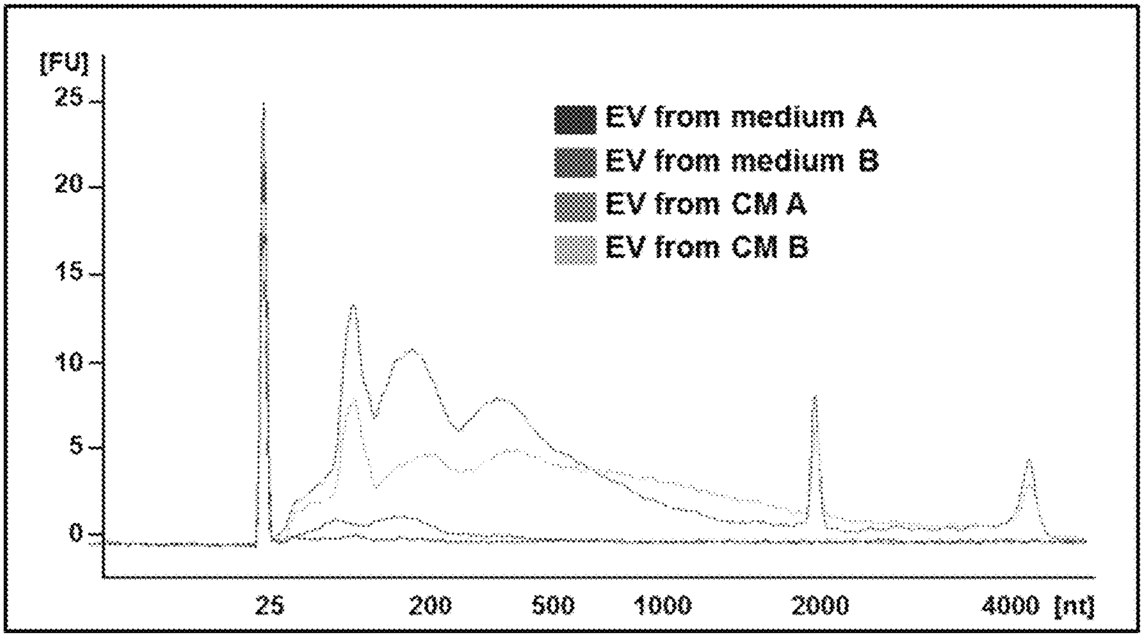
Figure 9:
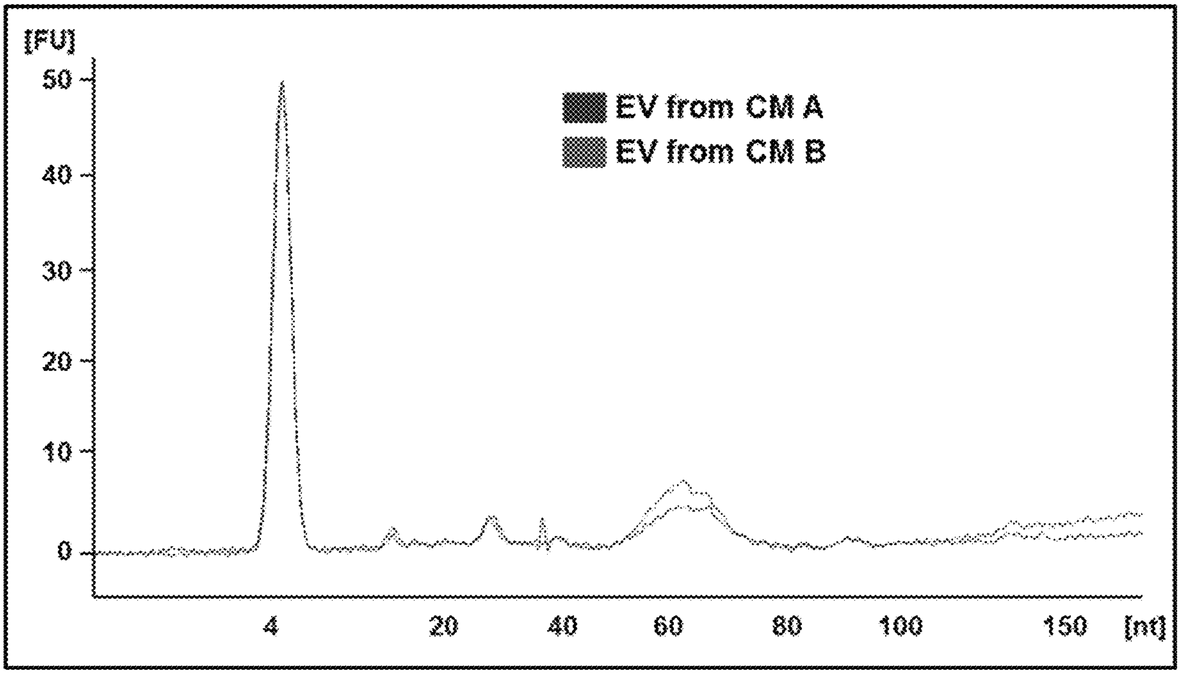
Figure 9:
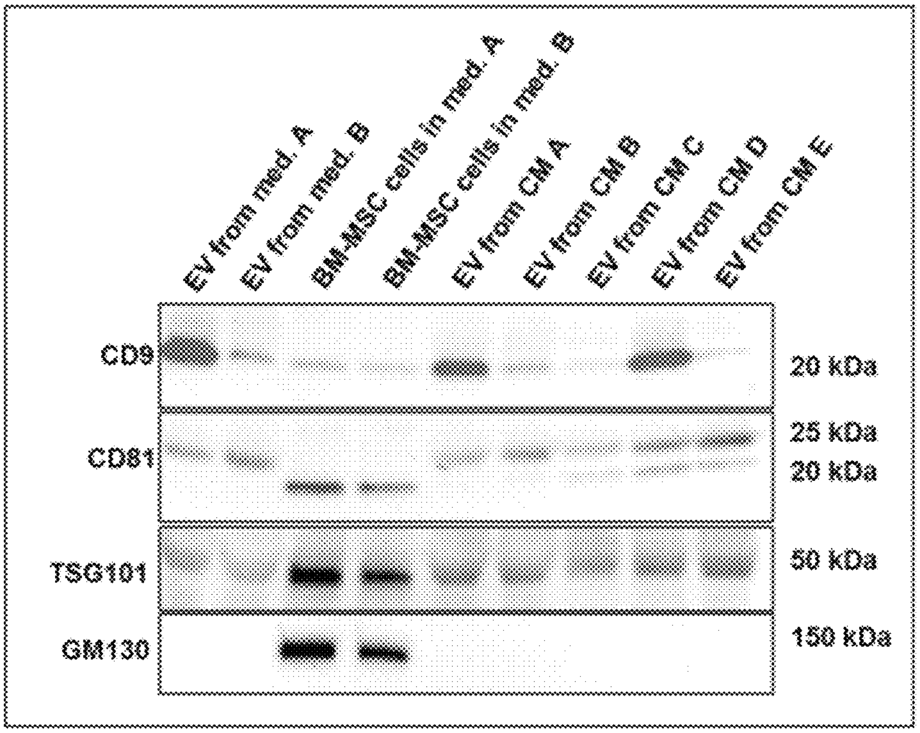
Figure 21:
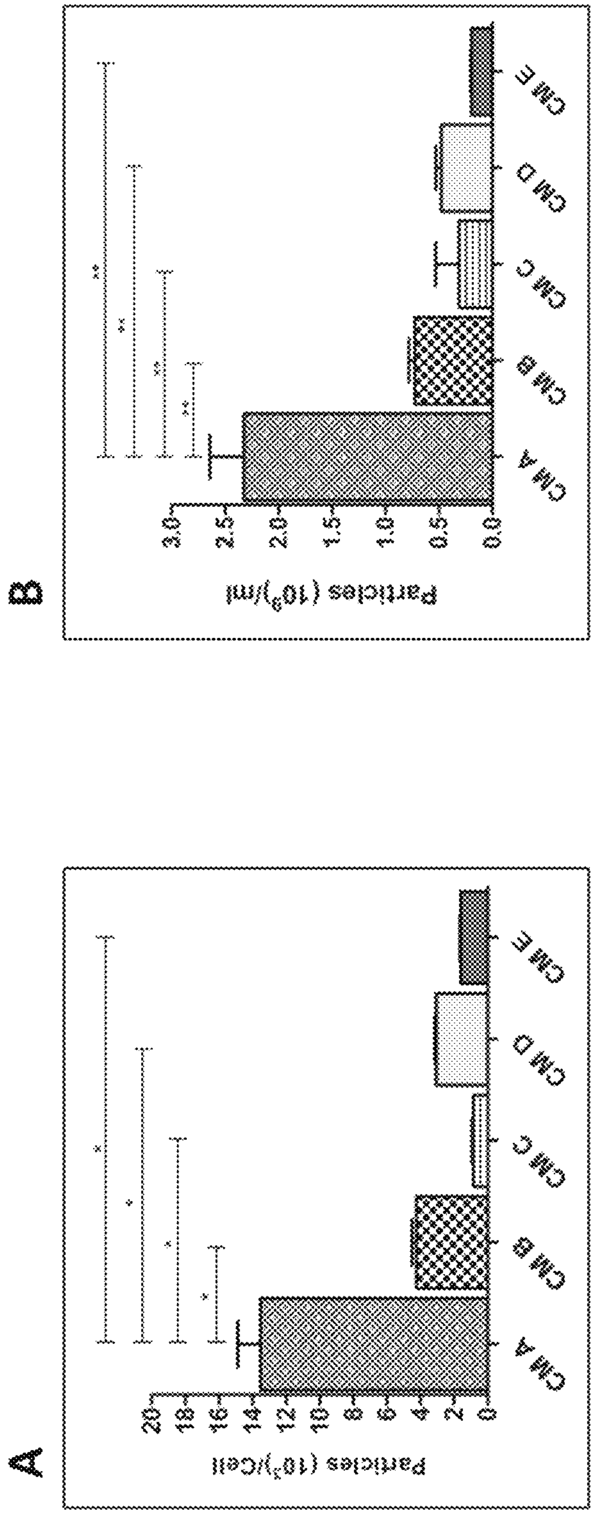
Figure 21:
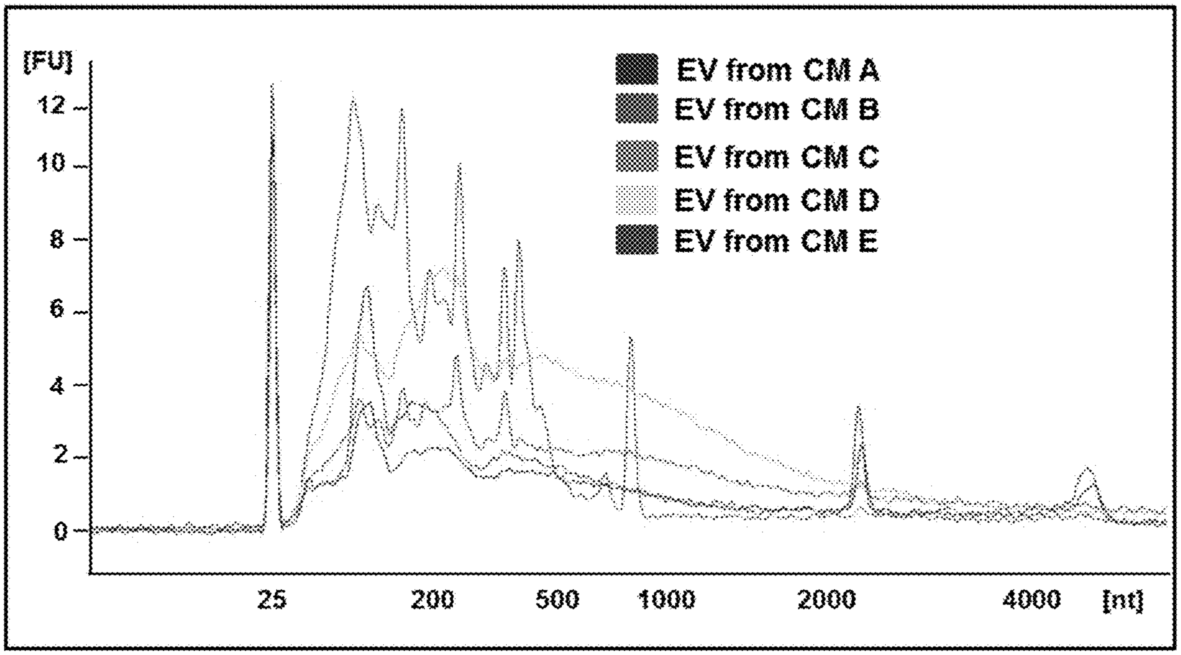
Figure 21:
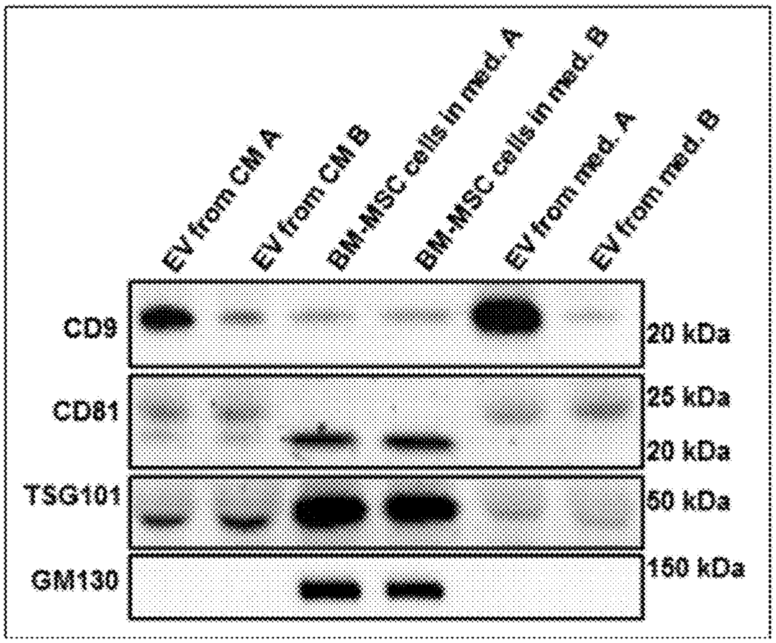

Furthermore, the extracellular-vesicles of the invention are positive for CD9, CD81 and TSG101 and are negative for GM130; see FIGS. 9 and 21. In addition, the MSCs from which the extracellular vesicles of the invention are released are positive for the surface markers CD73, CD90 and CD105, and optionally wherein the MSCs are negative for the surface markers CD14, CD19, CD34, CD45 and HLA-DR.

Accordingly, the extracellular vesicles show particular characteristics.

In addition, the appended examples unexpectedly demonstrated that the extracellular vesicles of the invention induce bone formation in an animal model, e.g., a rat femur segmented defect model; see Example 1. Accordingly, the extracellular vesicles can be used in (a) defect(s), disorder(s) and/or disease(s), wherein bone formation, cartilage formation and/or tendon formation is required.

Figure 3:
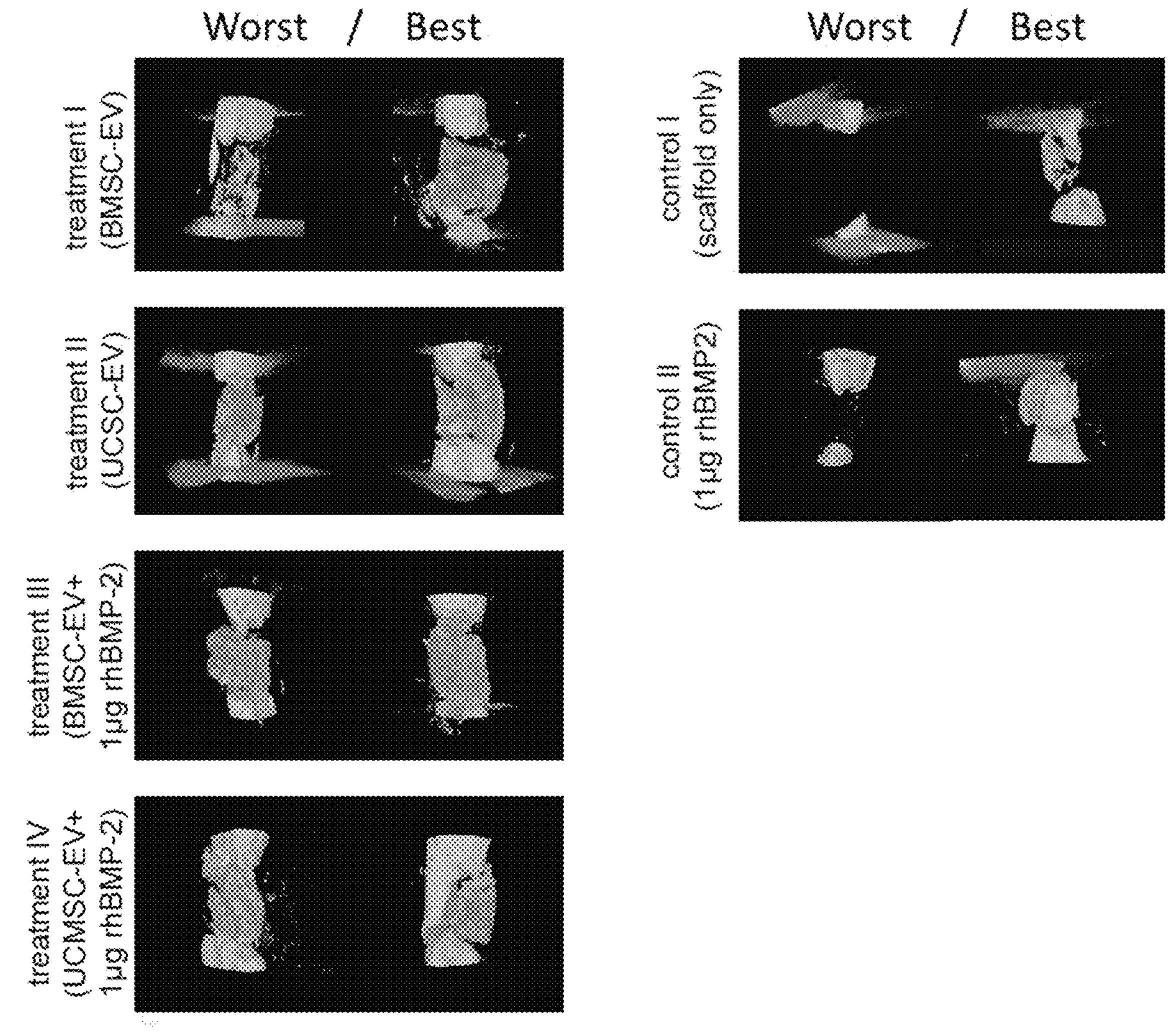

It is also demonstrated in the appended examples that extracellular vesicles derived from umbilical cord-derived mesenchymal stromal cells (UCMSCs) are superior in the bone formation compared to extracellular vesicles derived from bone marrow-derived mesenchymal stromal cells (BMSCs); see illustrative Table 2 and FIGS. 1 and 3. Accordingly, the extracellular vesicles derived from umbilical cord-derived mesenchymal stromal cells (UCMSCs) are herein most preferred.

Moreover, it was unexpectedly demonstrated in the appended examples that a pharmaceutical composition comprising the extracellular vesicles of the invention and a low dose of a Bone Morphogenic Protein (BMP), such as BMP2, results in an even more increased bone formation compared to the treatment with the extracellular vesicles of the invention or BMP2 alone; see e.g. Table 2 and FIGS. 1 and 3. This osteo-inductive effect can be observed with a lower dose of the BMP compared to conventionally administered BMP doses. In the prior art, a conventional dose of BMP2 is, for example, at least 5 μg/200 g in rats (Schmidt-Bleek et al., 2016). In the appended examples, it is surprisingly demonstrated that a single dose of 1 μg BMP2 in combination with the extracellular vesicles further increases the bone formation in a rat femur segmental defect model; see e.g. Table 2 and FIGS. 3 and 4. This is particularly surprising because a reduction to 1 μg rhBMP2 did not induce healing, in particular newly formed bone tissue, in a critical size defect in a rat osteotomy model (Glatt et al., 2016). Such a low dose may correspond in human to a dose of BMP that is between about 10 μg to about 10 mg. Accordingly, the extracellular vesicles obtained according to the method provided herein allow the use of a low dose of at least one BMP in the treatment of a bone defect, tendon defect and/or spinal cord injury. However, the medical intervention of bone defects and tendon defects with the extracellular vesicles of the invention is particularly preferred.

In the animal studies of the appended examples, a scaffold comprising either the extracellular vesicles of the invention alone or the extracellular vesicles of the invention and the BMP was administered to the animal model as a single dose. Therefore, the pharmaceutical composition of the invention is particularly administered as a single dose.

The treatment of a bone defect is further improved by a combination of the extracellular vesicles of the invention and one or more BMPs. This combination therapy even allows the use of lower dose of BMPs than the conventionally administered dose, e.g. of at least 12 mg. Therefore, it is herein above and below plausibly demonstrated that the pharmaceutical composition of the invention comprising the extracellular vesicles of the invention, or the extracellular vesicles of the invention and one or more BMPs can used in the treatment of (a) bone defect(s), tendon defect(s) and/or spinal cord injury.

Furthermore and as demonstrated surprisingly in appended Examples 3, tendon defects, in particular enthesopathies, treated with the extracellular-vesicles of the invention (in particular that are essentially free of heparin), or with the extracellular-vesicles of the invention and BMP are significantly less stiffer compared to untreated tendon defects. Therefore, it is herein demonstrated that the pharmaceutical composition of the invention comprising the extracellular-vesicles of the invention, or the extracellular-vesicles of the invention and one or more BMPs can be used in the treatment of (a) tendon defect(s), in particular in the treatment of enthesopathies, with reduced stiffness of the treated tendon, in particular of the enthesis. Thus, the invention also relates to the pharmaceutical composition comprising the extracellular-vesicles of the invention, or the extracellular-vesicles of the invention and one or more BMPs for reducing the tendon stiffness, in particular tendon enthesis stiffness, of (a) tendon defect(s), in particular enthesopathies. In other words, the invention also relates to the pharmaceutical composition comprising the extracellular-vesicles of the invention, or the extracellular-vesicles of the invention and one or more BMPs for reducing the tendon stiffness, in particular tendon enthesis stiffness, in or after the treatment of (a) tendon defect(s), in particular enthesopathies.

Accordingly, the invention also relates to the pharmaceutical composition comprising the extracellular-vesicles of the invention, or the extracellular-vesicles of the invention and one or more BMPs for increasing the tendon elasticity or flexibility, in particular the tendon enthesis elasticity or flexibility, e.g. in or after the treatment of (a) tendon defect(s), in particular enthesopathies.

In accordance with this embodiment, the treatment/medical intervention of/in tendon defects with use of the extra-cellular-vesicles of the invention provides for unexpected, surprisingly beneficial medical results.

The reduced stiffness of the tendon (in particular the reduced stiffness of the tendon enthesis) may refer to an increased elasticity or flexibility of the tendon, and in particular of the tendon enthesis.

Accordingly, the pharmaceutical composition comprising the extracellular vesicles of the invention, or the extracellular-vesicles of the invention and one or more BMPs may increase the tendon elasticity or flexibility, in particular the tendon enthesis elasticity or flexibility (or may reduce the tendon stiffness, in particular tendon enthesis stiffness) compared to a tendon defect that is not (or that is not yet) medically treated by a medical physician or the like, e.g. wherein this effect is employed in or after the treatment of (a) tendon defect(s), in particular enthesopathies. This effect can also be increased or reduced, respectively, in comparison to the tendon defect of a group of patients suffering from a tendon defect that is not (or that is not yet) medically treated by a medical physician or the like.

The increased elasticity/flexibility of the tendon (in particular the tendon enthesis) is beneficial since further tendon defects may be prevented, e.g. the rupture of the tendon, in particular the tendon enthesis.

The skilled person is aware how to determine the stiffness or elasticity (flexibility) of tendon(s) or tendon enthesis. An exemplary method for the determination is demonstrated in the appended Example 3.

In the appended examples, it is also surprisingly shown that MSCs that are cultured in a medium that is essentially free of vesicles not derived from the MSCs (such as vesicles occurring in cell culture supplements), heparin and fibrinogen exhibit a more homogenous osteogenic pattern compared to MSCs that are cultured in a medium that is essentially free of heparin and fibrinogen; see Example 2, e.g., FIG. 8*c*. The adipogenic differentiation potential of the MSCs was comparable in both culture media. Consequently, the removal of vesicles not derived from the MSCs from the culture medium in addition to the removal of heparin and fibrinogen from the culture medium does not negatively influence the MSC differentiation potential, but rather show an unexpected positive effect on the osteogenic differentiation potential of the MSCs.

In addition, the extracellular-vesicles of the invention or the extracellular-vesicles obtained by the methods of the invention are immunomodulatory.

The herein provided extracellular-vesicles are also documented to comprise TSG-6. This marker indicates an effective suppression of inflammation. Accordingly, the extracellular-vesicles of the invention or the extracellular-vesicles obtained by the methods of the invention may be used in suppressing inflammation.

The extracellular vesicles of the invention, the methods obtaining the extracellular vesicles of the invention, and the pharmaceutical composition comprising the extracellular vesicles provide, inter alia, the following advantages over prior art methods and extracellular vesicles. The extracellular vesicles of the invention are obtained by culturing MSCs in a culture medium that is essentially free of heparin and vesicles not derived from the MSCs, such as vesicles occurring in FBS, pHPL or other cell culture supplement. The use of a culture medium that is essentially free of heparin seems to be advantageous for the production of therapeutically active extracellular vesicles. Atai et al., 2013 demonstrated that heparin interferes with uptake of tumor-derived as well as non-tumor-derived extracellular vesicles into recipient cells. Therefore, the methods for the production of the extracellular vesicles and the extracellular vesicles obtained by the methods of the invention are advantageous because heparin is avoided.

Furthermore, cell culture supplements, such as FBS or pHPL, comprise fibrinogen/fibrin. Under the conditions of a common cell culture medium, fibrin clot formation takes place. Therefore, the components of the cell culture supplements, such as fibrin, necessitate addition of anticoagulants, for example heparin, to prevent gelatinization of cell culture medium. In addition, fibrin/fibrinogen may contribute to extracellular vesicle aggregation (Mulcahy et al., 2014). Accordingly, the avoidance of fibrin or fibrinogen in the production of extracellular vesicles is further beneficial. Therefore, extracellular vesicles essentially free of fibrin and/or fibrinogen are beneficial.

Moreover, extracellular vesicles derived from MSCs are usually contaminated with vesicles not derived from MSCs, such as vesicles occurring in serum, plasma or platelet lysate, in the prior art (Linares et al., 2015; Baglio et al, 2015; Gardiner et al, 2016). Such serum-derived vesicles or vesicles not derived from MSCs are co-purified with the extracellular vesicles derived from the MSCs. Such co-purified vesicles interfere with a reliable characterisation and may even result in adverse effects when administered to the patient. For example, such co-purified vesicles are internalised into cells and may have an impact on cell migration, proliferation and differentiation (see e.g., Shelke et al., and Torreggiani et al.). The methods herein provided to obtain the extracellular vesicles of the invention use a culture medium to culture the MSCs that is, inter alia, essentially free of such co-purified vesicles derived from cell culture supplements, such as FBS or pHPL. Accordingly, the obtained extracellular vesicles of the invention are essentially free of such co-purified vesicles derived from cell culture supplements, such as FBS or pHPL. Accordingly, the obtained extracellular vesicles of the invention are more enriched/concentrated compared to the prior art vesicles.

Therefore, the extracellular vesicles are essentially free of animal-derived xenogenic additives. Thus, the extracellular vesicles provided herein fulfil the demand of a near homogenous content as well as production under defined medium conditions, devoid of both xenogenic substances and serum-derived vesicles. Therefore, the methods provided herein provide a GMP-grade protocol for clinical applications. Moreover, this method allows the definition of the MSC-derived active compounds as no other source of vesicle contamination other than the cultured and immunophenotyped MSCs contribute to the conditioned media. Accordingly, the extracellular vesicles can be an off-the-shelf product.

Therefore, the herein provided methods and extracellular vesicles are advantageous over the prior art.

In summary, the herein provided methods provide extracellular vesicles derived from MSCs (i) that are essentially free of potential harmful components, which should thus be avoided in clinical practice, (ii) that show particular characteristics and are thus different from other extracellular vesicle preparations, and (iii) that demonstrate strong bone regeneration efficiency.

The invention relates to methods for obtaining extracellular-vesicles derived from mesenchymal stromal cells (MSCs), wherein the extracellular-vesicles are essentially free of vesicles not derived from the MSCs, and wherein the extracellular-vesicles are essentially free of heparin, and preferably fibrinogen. The invention also relates to the extracellular-vesicles obtained by the methods of the invention. The invention also relates to the medium comprising such extracellular vesicles and the MSCs secreting such extracellular vesicles. The above and below provided definitions and explanations refer to all of the embodiments of the invention mutatis mutandis.

As used herein, the term "extracellular vesicles", "extracellular-vesicles" or "EVs" refers to extracellular vesicles that are membrane surrounded structures released by mesenchymal stromal cells (MSCs) that are cultured in a culture medium that is essentially free of vesicles not derived from the MSCs and that is essentially free of heparin, and preferably that is essentially free of fibrinogen. In particular aspects, the "extracellular-vesicles" are released by MSCs cultured in medium that is essentially free of vesicles comprised in serum, human platelet lysate, or plasma and that is essentially free of heparin, and preferably that is essentially free of fibrinogen. In even more particular aspects, the "extracellular-vesicles" are released by MSCs cultured in medium that is essentially free of vesicles comprised in HPL and/or FBS and that is essentially free of heparin, and preferably that is essentially free of fibrinogen. The extracellular vesicles may include exosomes, microvesicles, cell-derived vesicles, and shedding vesicles.

As used herein, the term "extracellular-vesicles derived from mesenchymal stromal cells (MSCs)" refers to extracellular vesicles that are released from the MSCs or that are secreted by the MSCs.

As used herein, the term "vesicles not derived from the MSCs" refers to non-MSC origin vesicles. In other words, the term "vesicles not derived from the MSCs" refers to the term "vesicles that are not derived from the MSCs". The vesicles not derived from the MSCs may be identified by the content of the vesicles. For example, such vesicles may comprise a different RNA profile in comparison to vesicles of the invention. Thus, the skilled person could for example identify vesicles not derived from the MSCs by RNA sequencing/profiling. The vesicles not derived from the MSCs may be comprised in a culture medium. Accordingly, the vesicles not derived from the MSCs may be comprised in a culture medium prior to the culturing of the MSCs in order to release the extracellular-vesicles. The vesicles not derived from the MSCs can be comprised in a cell culture supplement that is added to the culture medium. As used herein, the term "culture medium" refers to a culture medium that includes (a) cell culture supplement(s). Such a culture medium can be used to culture MSCs with a sufficient survival rate, e.g., at least 90%. Thus, the culture medium may comprise (a) cell culture supplement(s) such as serum (e.g. fetal bovine serum (FBS)), platelet lysate (e.g. human platelet lysate (HPL)), and/or plasma. The culture medium may further comprise additives referring to chemically defined substances, such as glutamine or buffer salts, and growth promoting factors, such as various growth factors produced by cells in tissue such as blood.

Accordingly, the term "vesicles not derived from the MSCs" may particularly refer to vesicles that are comprised in serum, human platelet lysate, and/or plasma. Accordingly, in such aspects, the extracellular vesicles of the invention may be essentially free of vesicles that are comprised in serum, human platelet lysate, and/or plasma. Such extracellular vesicles can be obtained by the method, wherein the MSCs are cultured in a culture medium to release the extracellular vesicles, wherein the culture medium comprises serum, human platelet lysate, and/or plasma and wherein the culture medium is depleted of vesicles comprised in serum, human platelet lysate, and/or plasma.

In particular aspects, the invention relates to the extracellular-vesicles derived from mesenchymal stromal cells (MSCs), or to the methods for obtaining such extracellular-vesicles or to such extracellular vesicles obtained by such methods, wherein the extracellular-vesicles are essentially free of vesicles that are comprised in serum, human platelet lysate, and/or plasma, and wherein the extracellular-vesicles are essentially free of heparin, and preferably wherein the extracellular-vesicles are essentially free of fibrinogen/fibrin.

In further particular aspects, the term "vesicles not derived from the MSCs" refers to vesicles comprised in HPL and/or FBS. Accordingly, and in such aspects, the extracellular vesicles of the invention are essentially free of vesicles that are comprised in human platelet lysate and/or FBS. Such extracellular vesicles can be obtained by the method, wherein the MSCs are cultured in a culture medium to release the extracellular vesicles, wherein the culture medium comprises HPL and/or FBS and wherein the culture medium is depleted of vesicles comprised in HPL and/or FBS.

In such aspects, the invention relates to the extracellular-vesicles derived from mesenchymal stromal cells (MSCs), or to the methods for obtaining such extracellular-vesicles or to such extracellular vesicles obtained by such methods, wherein the extracellular-vesicles are essentially free of vesicles that are comprised in human platelet lysate (HPL) and/or fetal bovine serum (FBS), and wherein the extracellular-vesicles are essentially free of heparin, and preferably wherein the extracellular-vesicles are essentially free of fibrinogen/fibrin.

The extracellular vesicles of the invention are essentially free of vesicles that are not derived from the MSCs and are essentially free of heparin and preferably fibrinogen/fibrin. Accordingly, the extracellular-vesicles of the invention comprise at least about 80%, preferably at least about 85%, more preferably at least about 90%, more preferably at least about 94.4%, more preferably at least about 95%, more preferably at least about 96%, more preferably at least about 97%, more preferably at least about 98%, more preferably at least about 99%, more preferably at least about 99.5%, more preferably at least about 99.6%, more preferably at least about 99.7%, more preferably at least about 99.8%, or more preferably at least about 99.9% of extracellular-vesicles derived from the MSCs, or most preferably 100% of extracellular-vesicles derived from the MSCs.

As used herein, the term "essentially free of vesicles not derived from the MSCs" means that less than about 5%, preferably less than about 1%, more preferably less than about 0.5%, more preferably less than about 0.1%, or most preferably less than about 0.05% of vesicles not derived from the MSCs are comprised in the extracellular vesicles of the invention.

As used herein, the term "essentially free" of vesicles that are comprised in serum, human platelet lysate, and/or plasma means that less than about 5%, preferably less than about 1%, more preferably less than about 0.5%, more preferably less than about 0.1%, or most preferably less than about 0.05% of vesicles comprised in serum, human platelet lysate, and/or plasma are comprised in the extracellular vesicles of the invention.

As used herein, the term "essentially free" of vesicles that are comprised in human platelet lysate (HPL) and/or fetal bovine serum (FBS) means that less than about 5%, preferably less than about 1%, more preferably less than about 0.5%, more preferably less than about 0.1%, or most preferably less than about 0.05% of vesicles comprised in human platelet lysate (HPL) and/or fetal bovine serum (FBS) are comprised in the extracellular vesicles of the invention.

The extracellular vesicles of the invention are essentially free of vesicles not derived from the MSCs and are essentially free of an anticoagulant. Further, the extracellular vesicles of the invention are essentially free of vesicles not derived from the MSCs and are essentially free of an anticoagulant and fibrinogen. Further, the extracellular vesicles of the invention are essentially free of vesicles not derived from the MSCs and are essentially free of fibrinogen. Further, the extracellular vesicles of the invention are essentially free of vesicles not derived from the MSCs and are essentially free of an anticoagulant (e.g. heparin) and/or of fibrinogen. The culture medium employed in the methods to obtain the extracellular vesicles of the invention and the extracellular-vesicles provided herein are essentially free of anticoagulants. Various anticoagulants are known to the skilled person. Heparin is an exemplary anticoagulant.

As used herein, the term "essentially free" of an anticoagulant or of heparin means that less than about 5%, preferably less than about 1%, more preferably less than about 0.5%, more preferably less than about 0.1%, or most preferably less than about 0.05% extracellular vesicles comprise or bind to the anticoagulant or heparin. In particular, essentially free of an anticoagulant or of heparin may refer herein that less than about 5%, preferably less than about 1%, more preferably less than about 0.5%, more preferably less than about 0.1%, or most preferably less than about 0.05% extracellular vesicles comprise or bind to exogenously anticoagulant or exogenously heparin, i.e. anticoagulant or heparin that has been added, e.g. by artificial means, to the MSCs or to the extracellular vesicles.

Fibrinogen is a glycoprotein that promotes the formation of clots in vertebrates. If no anticoagulant is added to the culture medium, fibrin clot formation takes place. The fibrinogen clots if the calcium concentration is high enough. The culture medium usually has a concentration of calcium such that fibrin clots. Therefore, the methods provided herein may comprise a step of removing the fibrin or the fibrinogen from the culture medium. As used herein, the term "fibrinogen" includes fibrinogen and fibrin. Accordingly, essentially free of fibrinogen may refer to essentially free of fibrinogen and fibrin.

As used herein, the term "essentially free" of fibrinogen/fibrin means that less than about 5%, preferably less than about 1%, more preferably less than about 0.5%, more preferably less than about 0.1%, or most preferably less than about 0.05% extracellular vesicles comprise or bind to fibrinogen/fibrin.

The extracellular-vesicles essentially free of vesicles not derived from the MSCs, e.g. vesicles comprised in FBS or HPL, can be obtained by the methods provided herein. For example, the extracellular-vesicles derived from mesenchymal stromal cells (MSCs) may be obtained by:

(i) removing fibrinogen/fibrin from the culture medium, wherein no heparin is added to the culture medium, and removing vesicles from the culture medium,
(ii) culturing MSCs in the culture medium of step (i),
(iii) isolating the extracellular-vesicles derived from the MSCs from the medium.

Further, the extracellular-vesicles derived from mesenchymal stromal cells (MSCs) that are essentially free of vesicles not derived from the MSCs may be obtained by:

(i) culturing of the MSCs in a culture medium that is essentially free of vesicles not derived from the MSCs and that is essentially free of heparin, and preferably that is essentially free of fibrinogen/fibrin; and
(ii) isolating the extracellular-vesicles derived from the MSCs from the culture medium.

Further, the extracellular-vesicles derived from mesenchymal stromal cells (MSCs) may be obtained by:

(i) adding HPL or FBS to a culture medium,
(ii) removing fibrinogen/fibrin from the culture medium, wherein no heparin is added to the culture medium,
(iii) removing vesicles from the culture medium,
(iv) culturing MSCs in the culture medium of steps (i) to (iii), and
(v) isolating the extracellular-vesicles derived from the MSCs from the medium.

Further, the extracellular-vesicles derived from mesenchymal stromal cells (MSCs) may be obtained by:

(i) adding HPL or FBS, and N(2)-L-alanine-L-glutamine to a minimum essential culture medium,
(ii) removing fibrinogen/fibrin from the culture medium, wherein no heparin is added to the culture medium,
(iii) removing vesicles from the culture medium,
(iv) culturing MSCs in the culture medium of steps (i) to (iii), and
(v) isolating the extracellular-vesicles derived from the MSCs from the medium.

As used herein, the term "removing vesicles" from the culture medium or the term "removing vesicles not derived from the MSCs" is used interchangeably herein and it means that vesicles that are comprised in the culture medium (e.g. that are comprised in the FBS or HPL) are removed or depleted. The methods provided herein can also comprise a step wherein a minimal medium, such as Alpha-modified Minimal Essential Medium Eagle (alpha-MEM) is supplemented with a serum, platelet lysate, and/or serum in order to obtain the culture medium to culture the MSCs. Prior to the culturing of the MSCs to release the extracellular-vesicles derived from the MSC, the vesicles of the culture medium may be removed in the methods of the present invention. In order to remove vesicles of the culture medium, any technique known to the skilled person can be applied that removes the vesicles such that the culture medium is essentially free of vesicles not derived from the MSCs. An exemplary procedure is described in the appended Examples; see e.g. Examples 1 and 2. For example, the vesicles comprised in the culture medium, e.g. comprising FBS or HPL, is centrifuged such that the vesicles comprised in the culture medium are separated from the culture medium. For instance, the culture medium can be centrifuged at 120.000 g for 3 hours.

Further, the vesicles comprised in the culture medium can be removed by means and methods that are based on sieving (e.g. Exomir) and/or affinity forces. For example, devices comprising glass fibers can be used to remove the vesicles comprised in the culture medium. In general, means and methods to obtain the extracellular vesicles, as described below, could also be employed to remove the vesicles comprised in culture medium.

As used herein, the term "vesicles not derived from the MSCs are vesicles that are comprised in a culture medium prior to the culturing of the MSCs" refers to the vesicles that occur in a culture medium, e.g. after the culture medium was supplemented with serum and/or lysate. In order to obtain the extracellular-vesicles of the invention, the MSCs are cultured in culture medium that was depleted from the vesicles comprised in the culture medium. Accordingly, prior to the culturing step, the vesicles comprised in the culture medium are depleted/removed.

As used herein, the term "removing fibrinogen" from the culture medium means that fibrinogen, and preferably fibrin is removed from the culture medium. The culture medium employed in the methods of the invention in order to obtain the extracellular-vesicles is essentially free of an anticoagulant, such as heparin, i.e. no anticoagulant (e.g. heparin) is added to the culture medium. Thus, the fibrin/fibrinogen forms a fibrin clot in the absence of the anticoagulant in the culture medium. The fibrin/fibrinogen can be removed from the culture medium, e.g. by centrifugation/pelleting. An exemplary procedure to remove the fibrin/fibrinogen from the culture medium is documented in the appended Examples; see e.g. Examples 1 and 2. For example, the culture medium that does not comprise the anticoagulant can be incubated until the fibrin clot is formed and can subsequently be centrifuged to separate the fibrin from the culture medium. In particular aspects, no heparin is added to the culture medium prior to the removal of the fibrinogen.

As understood herein, in the methods of the present invention, the order of the steps removing fibrinogen/fibrin and removing vesicles not derived from the MSCs can be changed, so that first fibrinogen/fibrin is removed from the culture medium or that first the vesicles not derived from the MSCs are removed from the culture medium.

As used herein, the term "culturing of the MSCs" or grammatical variants thereof means that MSCs are maintained in a culture medium such that the MSCs release extracellular-vesicles into this culture medium. Accordingly, the extracellular-vesicles are derived from MSCs that are cultured in a culture medium, and wherein the fibrinogen/fibrin and the vesicles were removed from the culture medium prior to the culturing of the MSCs, and preferably wherein said culture medium was supplemented with a cell culture supplement (such as FBS or HPL) comprising vesicles.

Accordingly, the term "culturing MSCs in the culture medium of steps (i) to (iii)" refers to culturing MSCs in the culturing medium obtained in the step "removing vesicles from the culture medium (e.g. designated step (iii)).

Before the MSCs are cultured in the culture medium that is used to release and collect the extracellular vesicles of the invention, the MSCs can be maintained in a culture medium that comprises heparin, fibrin/fibrinogen, and vesicles not derived from the MSCs. Prior to the culturing step to release the extracellular vesicles, the MSCs may optionally be washed, e.g., with culture medium and/or phosphate buffer saline (PBS). Subsequently, the washed MSCs may be cultured in the culture medium essentially free of vesicles not derived from the MSCs (e.g. vesicles of FBS and/or HPL) and essentially free of heparin, and preferably essentially free of fibrin/fibrinogen. Such a procedure is documented in the appended Examples. For example, the MSCs can be cultured in the culture medium for about 48 hours.

As used herein, the term "isolating the extracellular-vesicles", "collecting the extracellular-vesicles" or "purifying the extracellular vesicles" (or grammatical variants thereof) derived from the MSCs from the medium means that the extracellular vesicles (of interest) that are comprised in the culture medium are concentrated in order to obtain a more homogenous extracellular-vesicle preparation. In this context, the extracellular vesicles (of interest) that are comprised in the culture medium mean that prior to the culturing of the MSCs, the culture medium is essentially free of vesicles not derived from the MSCs and the culture medium is essentially free of the anticoagulant, such as heparin, and preferably is essentially free of fibrin/fibrinogen. The culturing of the MSCs leads to a release of the extracellular vesicles into the culture medium. Accordingly, the extracellular vesicles released from the MSCs can be collected and obtained from the culture medium. An exemplary procedure to isolate/collect/purify the extracellular vesicles of the invention is described in the appended Examples. For examples, the extracellular vesicles can be isolated by ultracentrifugation, ultrafiltration and/or tangential flow filtration. Exemplary procedures are described in Nordin et al., 2015 and Heinemann et al., 2014. Particularly, the extracellular-vesicles can be collected by ultrafiltration. The skilled person knows which further means and methods can be applied to isolate the extracellular vesicles.

The extracellular-vesicles of the invention, which can be obtained by the methods provided herein, were shown to have particular characteristics.

As shown in the appended Example 3, the extracellular vesicles obtained by the methods of the invention show a particular cytokine profile.

In particular aspects, the extracellular-vesicles or the extracellular vesicles obtained by the methods of the invention may comprise:

> about 200 pg/mL SDF1,
> about 200 pg/mL IL-6,
> about 200 pg/mL IL8,
> about 20 pg/mL GM-CSF, and/or
> about 100 pg/mL BDNF.

The corresponding measurements and methods for determining a cytokine profile are known in the art and are also exemplified in the appended examples. Accordingly, one method comprises an immune-assay, such as an ELISA assay.

In particular aspects, the extracellular-vesicles or the extracellular vesicles obtained by the methods of the invention may comprise combinations of any or all of the above of the provided cytokines.

During development, brain derived neurotrophic factor (BDNF) promotes the survival and differentiation of selected neuronal populations of the peripheral and central nervous systems. BDNF participates in axonal growth, pathfinding and in the modulation of dendritic growth and morphology and is a major regulator of synaptic transmission and plasticity at adult synapses in many regions of the CNS. Therefore, the versatility of BDNF is emphasized by its contribution to a range of adaptive neuronal responses including long-term potentiation (LTP), long-term depression (LTD) and certain forms of short-term synaptic plasticity.

Stromal cell-derived factor-1α ("SDF-1α" or "SDF-1") is a chemokine that plays a major role in cell trafficking and homing of CD34(+) stem cells. Studies employing SDF-1/CXCR4 have demonstrated its therapeutic potential in tissue engineering. During injury, cells from the injured organ highly express SDF-1, which causes an elevation of localized SDF-1 levels. This leads to recruitment and retention of circulating CD34(+) progenitor cells at the injury site via chemotactic attraction toward a gradient of SDF-1. The general approaches for SDF-1 introduction in tissue engineering are direct protein incorporation into scaffolds and transplantation of SDF-1-overexpressing cells and both methods are successful in improving the regeneration of the damaged tissue/organ. These SDF-1 delivery designs and platforms hold much room for improvement. Regardless of the different techniques of SDF-1 delivery, they have proved to be effective in recruitment of various stem/progenitor cells. Interleukin 1 (IL-1) family is a group of cytokines with multiple local and systemic effects, which regulates both innate and adaptive immune responses. Generally, most IL-1 family cytokines express prevailing pro-inflammatory activities (IL-1α, IL-1β, IL-18, IL-33, IL-36 α, β, γ), whereas others are anti-inflammatory (IL-1Ra (IL-1 receptor antagonist), IL-36Ra, IL-38, IL-37). In addition to their immunomodulatory roles, some of them are also involved in the physiological modulation of homeostatic processes and directly affect mRNA transcription. IL-1 family cytokines bind to specific receptors composed of a ligand-binding chain and an accessory chain. The pro-inflammatory effects of IL-1 family cytokines are regulated on the level of transcription, enzymatic processing of precursors, release of soluble antagonists, and expression of decoy receptors. Members of the IL-1 family regulate the recruitment and activation of effector cells involved in innate and adaptive immunity, but they are also involved in the pathogenesis of chronic disorders, including inflammatory bowel disease, rheumatoid arthritis, and various autoimmune and autoinflammatory diseases.

Accordingly, it is plausible that the extracellular-vesicles of the invention comprising these cytokines support the immunomodulatory and neuroprotective therapeutic activity.

The extracellular vesicles obtained by the methods of the invention may also be characterized via a particular miRNA profile and/or protein profile.

For example, the appended Examples demonstrate that the extracellular-vesicles show a particular miRNA profile. The extracellular vesicles may comprise at least one of the miRNA selected from the group consisting of hsa-miR-146a-5p, hsa-miR-92a-3p, hsa-miR-21-5p, hsa-miR-148a-3p, hsa-miR-221-3p, hsa-let-7i-5p, and hsa-let-7f-5p. In particular aspects, the extracellular vesicles may comprise hsa-miR-146a-5p, hsa-miR-92a-3p, hsa-miR-21-5p, hsa-miR-148a-3p, hsa-miR-221-3p, hsa-let-7i-5p, and hsa-let-7f-5p.

In particular, the extracellular-vesicles or the extracellular vesicles obtained by the methods of the invention may comprise hsa-miR-146a-5p, hsa-miR-92a-3p, hsa-miR-21-5p, hsa-miR-148a-3p, hsa-miR-221-3p, hsa-let-7i-5p, and hsa-let-7f-5p among the 20 most abundant miRNAs. These miRNAs are not found among the 20 most abundant miRNAs in the extracellular vesicles obtained in the prior art, e.g. in Baglio et al., 2015.

In particular, the extracellular-vesicles or the extracellular vesicles obtained by the methods of the invention may comprise hsa-miR-148a-3p and/or hsa-miR-221-3p among the 20 most abundant miRNAs, or preferably among the 20 most abundant miRNAs.

In particular, the extracellular-vesicles or the extracellular vesicles obtained by the methods of the invention may comprise:

hsa-miR-146a-5p,
hsa-miR-148a-3p,
hsa-miR-92a-3p,
hsa-miR-21-5p,
hsa-miR-221-3p,
hsa-let-7i-5p, and hsa-let-7f-5p, wherein the level of these miRNAs together comprise up to about 50% of the total miRNA content among the 20 most abundant miRNAs.

Further, the extracellular-vesicles may be essentially free of at least one, preferably two, more preferably four, most preferably all of the miRNAs selected from the group consisting of hsa-miR-133, hsa-miR-135, hsa-miR-204, hsa-miR-211, hsa-miR-17, and hsa-miR-106. In particular aspects, the extracellular-vesicles may be essentially free of hsa-miR-133, hsa-miR-135, hsa-miR-204, hsa-miR-211, hsa-miR-17, and hsa-miR-106. Such miRNAs are disclosed in Kang and Hata, 2014. In this context, essentially free of a particular miRNA means that less than about 5%, preferably less than about 1%, more preferably less than about 0.5%, more preferably less than about 0.1%, or most preferably less than about 0.05% of this particular miRNA is comprised in the extracellular vesicles.

The miRNA, hsa-miR-146a-5p, regulates, inter alia, immunetolerance via Stat1 in T-regs, proinflammatory cytokine production, monocyte and dendritic cell activation and mediates protective innate immune tolerance. hsa-miR-146a-5p targets at least tumor necrosis factor receptor-associated factor 6 (TRAF6), IL-1 receptor-associated kinase-1 (IRAK1), CXCR4 and Stat1 (Lu et al., 2010; Chassin et al, 2010; So et al., 2013; Wang et al, 2013; Park et al, 2015). The terms “hsa-miR-146a-5p” and “miRNA 146a-5p” refer to the same miRNA and can be used exchangeable.

The miRNA, hsa-miR-92a-3p, regulates cell proliferation and apoptosis, suppresses angiogenic activity of MSC by down-regulating HGF, is involved in chondrogenesis and the chondrocyte response induced by IL-1β, positively contributes to the expression of col9a2 and aggrecan. Further, hsa-miR-92a-3p targets tumor necrosis factor alpha receptor (TNFR1) and collagen type1 (Hou et al., 2015, Li et al., 2012).

The miRNA, hsa-miR-21-5p, mediates the osteogenic switch, shows an increased expression during osteogenesis, suppresses pluripotency, increases osteogenic differentiation and increases expression of Runx2. Further, hsa-miR-21-5p targets Sox2, a repressor of cell differentiation (Eguchi et al., 2013).

The miRNA, hsa-miR-148a-3p promotes osteoclast differentiation and is upregulated during osteoclastogenesis (Liu, X. Y. et al, 2015; Liu, J. et al. 2015).

The miRNA, hsa-let-7i-5p, is a positive regulator of bone development, a negative regulator of adipogenic differentiation, is in adults restricted to tissue of mesenchymal origin, is associated with highly proliferating MSCs, is tightly regulated by FGF2, acts as a negative regulator of angiotensin2 and is induced inflammation and fibrosis (Wang et al. 2015; Wei et al. 2014, Kalomoiris et al., 2016).

The miRNA, hsa-miR-221-3p, exerts cytoprotective effects in hypoxia-reoxygenation injury (H/R), protective effects are due to the inhibition of H/R-induced autophagy, attenuates the osteogenic differentiation of human annulus fibrosus cells and silencing miR-221 has a prochondrogenic role in vivo (Yeh et al., 2016).

The miRNA, hsa-let-7f-5p, suppresses glioma cell proliferation, migration and invasion. hsa-let-7f-5p targets periostin Yan et al., 2015; Bonnet et al., 2016; Walker et al., 2016).

The miRNA, hsa-miR-22-3p, mediates the osteogenic switch, shows an increased expression during osteogenesis and inhibits adipogenic differentiation. Further, hsa-miR-22-3p targets HDAC 6, and a co-repressor of RUNX2 (Huang et al., 2012).

In particular aspects, the extracellular-vesicles of the invention comprise a particular miRNA profile. The extracellular vesicles or the extracellular vesicles obtained by the methods of the invention comprise hsa-miR-146a-5p as the most abundant miRNA. In this context, the term “miRNA 146a-5p is the most abundant miRNA” or “hsa-miR-146a-5p as the most abundant miRNA” may refer to a level of about 80% to 100% of hsa-miR-146a-5p in extracellular vesicles. In this context, the term "about" refers to ±10% of the indicated numerical value, and preferably to ±5% of the indicated numerical value. The measurement of the level of 80% to 100% of hsa-miR-146a-5p in the extracellular vesicles is shown in FIG. 1. The measurements of the hsa-miR-146a-5p level in extracellular vesicles cultured in other culture media is shown in table 1 and described herein below.

In order to determine the miRNA profile, the level of the miRNAs of the extracellular vesicles is determined. The determination and/or quantification of miRNA is routine in the art. The level of the miRNA, e.g. the miRNA content in the extracellular vesicle preparation, can be determined by various techniques, e.g., nucleic acid sequencing techniques, or qPCR. An exemplary procedure is documented in the appended examples. For example, the miRNA can be isolated from the extracellular vesicles, e.g. by a commercially available kit, such as mirVana miRNA Isolation Kit, and subsequently the nucleic acid sequence of the miRNAs can be can be determined by nucleic acid sequencing. The level of the miRNAs can also be expressed as the number of the reads in the sequencing analysis. The levels of the miRNAs may then be compared to each other and the ratios can be formed as described herein above and in the appended Examples.

The term "reads per million", "rpm", "transcripts per million", or "TPM" is herein used exchangeable. The term "TPM" refers to a unit used to measure expression in next generation sequencing experiments. The number of reads for a particular miRNA is divided by the total number of mapped reads and multiplied by one million (Tags per Million).

The particular level of the miRNAs comprised in the extracellular vesicles can be also ranked/sorted such that the miRNA with the highest level is the number one in the ranking and the miRNA with second highest level is the number 2 in the ranking and so forth. Accordingly, a miRNA not comprised among a number "X" of most abundant miRNAs refers to a miRNA that has a lower level compared to the miRNAs sorted with the numbers 1 to "X". For example, a miRNA not comprised among the 10 most miRNAs in the extracellular vesicles refers to a miRNA that has a lower level than the 10 most abundant miRNAs. An exemplary ranking/sorting of the 20 most abundant miRNAs is shown in table 1. In table 1, the miRNAs were sorted according to the level determined in the extracellular vesicles.

As described above, the miRNA 146a-5p may be the most abundant miRNA in the extracellular vesicles obtained by the methods of the invention (see FIG. 1). Accordingly, the level of the miRNA 146a-5p can be used as a reference in this analysis, i.e., the level of hsa-miR-146a-5p can be set to 100%. The level of the further miRNAs may then be determined in relation to this level, i.e. a ratio between the level of the further miRNA and the level of hsa-miR-146a-5p can be calculated.

As used herein, the term "the level of hsa-miR-146a-5p is set to 100%" means that the level of the miRNA 146a-5p is used as the reference miRNA. Accordingly, the level of hsa-miR-146a-5p may be set to 100%. The levels of the further/other miRNAs (e.g. hsa-miR-92a-3p, hsa-miR-21-5p, hsa-miR-148a-3, hsa-miR-221-3p, hsa-let-7i-5 and hsa-let-7f-5p) of the extracellular vesicles can be determined in relation to the level of the hsa-miR-146a-5p. That is, a ratio is formed between the level of the further/other miRNA and the level of hsa-miR-146a-5p. In such aspects, the extracellular-vesicles or the extracellular vesicles obtained by the methods of the invention may comprise:

| | |
|---|---|
| 100% of | hsa-miR-146a-5p, |
| at least about 50% of | hsa-miR-92a-3p, |
| at least about 15% of | hsa-miR-21-5p, |
| at least about 10% of | hsa-miR-148a-3p, |
| at least about 15% of | hsa-miR-221-3p, |
| at least about 5% of | hsa-let-7i-5p, and |
| at least about 5% of | hsa-let-7f-5p, |

wherein the level of hsa-miR-146a-5p is set to 100%. Optionally, the extracellular-vesicles may further comprise at least about 2% of hsa-miR-22-3p.

In certain aspects, the extracellular-vesicles or the extracellular vesicles obtained by the methods of the invention may comprise:

| | |
|---|---|
| 100% of | hsa-miR-146a-5p, |
| about 50 to 80% of | hsa-miR-92a-3p, |
| about 15 to 35% of | hsa-miR-21-5p, |
| about 10 to 20% of | hsa-miR-148a-3p, |
| about 15 to 30% of | hsa-miR-221-3p, |
| about 5 to 10% of | hsa-let-7i-5p, and |
| about 5 to 10% of | hsa-let-7f-5p, |

wherein the level of hsa-miR-146a-5p is set to 100%. Optionally, the extracellular-vesicles further comprise at least about 2% of hsa-miR-22-3p.

In particular aspects, the extracellular-vesicles or the extracellular vesicles obtained by the methods of the invention may comprise:

| | |
|---|---|
| 100% of | hsa-miR-146a-5p, |
| less than about 0.1% | hsa-miR-133, |
| less than about 0.1% | hsa-miR-135, |
| less than about 0.1% | hsa-miR-204, |
| less than about 0.1% | hsa-miR-211, |
| less than about 0.1% | hsa-miR-17, and |
| less than about 0.1% | hsa-miR-106, |

wherein the level of hsa-miR-146a-5p is set to 100%.

In particular, the extracellular-vesicles or the extracellular vesicles obtained by the methods of the invention may comprise:

hsa-miR-17,
hsa-miR-106,
hsa-miR-133,
hsa-miR-135,
hsa-miR-204, and
hsa-miR-211, wherein the level of these miRNAs together comprise less than about 5% of the total miRNA content among the 20 most abundant miRNAs.

In particular aspects, the extracellular-vesicles or the extracellular vesicles obtained by the methods of the invention may comprise:

| | |
|---|---|
| 100% of | hsa-miR-146a-5p, |
| at least about 50% of | hsa-miR-92a-3p, |
| at least about 15% of | hsa-miR-21-5p, |
| at least about 10% of | hsa-miR-148a-3p, |
| at least about 15% of | hsa-miR-221-3p, |
| at least about 5% of | hsa-let-7i-5p, |
| at least about 5% of | hsa-let-7f-5p, |
| less than about 0.1% | hsa-miR-133, |

-continued

| | |
|---|---|
| less than about 0.1% | hsa-miR-135, |
| less than about 0.1% | hsa-miR-204, |
| less than about 0.1% | hsa-miR-211, |
| less than about 0.1% | hsa-miR-17, and |
| less than about 0.1% | hsa-miR-106, |

wherein the level of hsa-miR-146a-5p is set to 100%. Optionally, the extracellular-vesicles further comprise at least about 2% of hsa-miR-22-3p.

In particular aspects, the extracellular-vesicles or the extracellular vesicles obtained by the methods of the invention do not comprise miR-22-3p and/or miR-222-3p among the 5 most abundant miRNAs, preferably among the 10 most abundant miRNAs, or most preferably among the 20 most abundant miRNAs. Preferably, the extracellular-vesicles are derived from umbilical cord-derived mesenchymal stromal cells (UC-MSCs) in this context.

In particular aspects, the extracellular-vesicles or the extracellular vesicles obtained by the methods of the invention do not comprise miR-486-5p and/or miR-191-5p among the 5 most abundant miRNAs, preferably among the 10 most abundant miRNAs, or most preferably among the 15 most abundant miRNAs. Preferably, the extracellular-vesicles are derived from umbilical cord-derived mesenchymal stromal cells (UC-MSCs) in this context.

In particular aspects, the extracellular-vesicles or the extracellular vesicles obtained by the methods of the invention do not comprise miR-22-3p, miR-222-3p, miR-486-5p and miR-191-5p among the 5 most abundant miRNAs, preferably among the 10 most abundant miRNAs, or most preferably among the 15 most abundant miRNAs. Preferably, the extracellular-vesicles are derived from umbilical cord-derived mesenchymal stromal cells (UC-MSCs) in this context.

Further, the extracellular vesicles of the invention may be positive for CD9, CD81 and TSG101 and may be negative for GM130. As used in this context, the term "positive" means that a level of the protein or a fragment thereof is determined that can be differentiated from the background, i.e. the level of the protein or the fragment thereof is increased compared to a blank. As used in this context, the term "negative" means that a level of the protein or a fragment thereof is not determined that can be differentiated from the background, i.e. the level of the protein or the fragment thereof is equal or similar compared to a blank.

In particular aspects of the invention, the level of CD9 of the extracellular vesicles of the invention is reduced in comparison to extracellular vesicles obtained by a cultivation in a culture medium that is free of fibrinogen/fibrin and heparin and that comprises vesicles comprised in the HPL or FBS, and preferably the level of CD9 of the extracellular-vesicles of the invention is increased in comparison to extracellular vesicles that are cultured in a culture medium that does not comprise serum or lysate, such as FBS or pHPL.

The protein content of the extracellular vesicles can be determined by various techniques, which are suitable to determine the protein content, e.g. Western Blot, or mass spectrometer based techniques. For example, Western Blot analysis is suitable as documented in the Examples. For such an analysis, the extracellular vesicles are collected from the respective culture medium and are lysed. A respective amount of the protein lysate is analyzed by SDS-PAGE. After blotting, the membrane is incubated with the respective antibodies and the level of the binding is determined.

Exemplary antibodies are documented in the appended Examples, e.g. against CD9 (sc-13118, Santa Cruz Biotechnology), CD81 (sc-7637, Santa Cruz Biotechnology), TSG101 (sc-7964, Santa Cruz Biotechnology), and GM130 (610823, BD Transduction Laboratories). The antibodies can be diluted 1:250 in TBS-T containing 0.5% non-fat dry milk, and can be incubated, e.g. at room temperature for 4 hours. After washing with TBS-T, the secondary antibody (goat anti-mouse HRP-conjugated, K4004, DAKO), can be diluted 1:200 in TBS-T containing 0.5% non-fat dry milk, e.g. for one hour at room temperature. Proteins were detected with ECL Prime Western Blotting Detection Reagent (RPN2232, GE Healthcare) and ChemiDoc MP System (Bio-Rad).

In particular aspects of the invention, the MSCs releasing the extracellular vesicles of the invention into the culture medium or the MSCs of the invention may be positive for the surface markers CD73, CD90 and CD105, and optionally wherein the MSCs are negative for the surface markers CD14, CD19, CD34, CD45 and HLA-DR. Such an analysis can be performed when the extracellular-vesicles are isolated. Thus, the MSCs are positive for the cell surface markers (CD73, CD90 and CD105) and are negative for the cell surface markers (CD14, CD19, CD34, CD45 and HLA-DR) when the extracellular-vesicles are isolated, i.e. at the time of harvest. As used in this context, the term "positive" means that a level of the protein or a fragment thereof is determined that can be differentiated from the background, i.e. the level of the protein or the fragment thereof is increased compared to a blank. As used in this context, the term "negative" means that a level of the protein or a fragment thereof is not determined that can be differentiated from the background, i.e. the level of the protein or the fragment thereof is equal or similar compared to a blank. In particular, the MSCs are considered to be positive for CD105, CD73 and CD90 expression if at least about 90% of cells stain for these proteins; the MSCs are considered to be negative for CD14, CD45, CD34 and CD19 expression if less than about 2% of cells stain for these proteins; and the MSCs are considered to be negative for MHC Class II (HLA-DR) if less than about 1% of cells stain for MHC Class II (HLA-DR).

Accordingly, the extracellular-vesicles are derived from MSCs or the extracellular vesicles obtained by the methods of the invention, wherein ≥90% of cells have CD105 expression;
≥90% of cells have CD73 expression;
≥90% of cells have CD90 expression;
≤2% of cells have CD14 expression;
≤2% of cells have CD45 expression;
≤2% of cells have CD34 expression;
≤2% of cells have CD19 expression; and
≤1% of cells have MHC Class II (HLA-DR) expression.

Accordingly, the cell surface markers may characterize the cells from which the extracellular vesicles obtained by the methods of the invention are derived from.

The surface marker expression can be analyzed by various techniques, which are suitable to determined surface markers. For example, fluorescence activated cell sorting (FACS) is suitable as documented in the appended Examples. For this method, the following exemplary antibodies can be employed: CD90 (IM1839U, Beckman Coulter, France), CD105 (MCHD10505, Life Technologies, Austria), CD14, CD19, CD34, CD45, CD73, HLA-II (DR) (345785, 345802, 345808, 550257, 347400 Becton Dickinson, Austria), or with corresponding isotype controls (345815, 345818, 555743, 345816, 349051, Becton Dickinson, Austria). Settings of the flow cytometer are also specified in the appended Examples.

Further, the extracellular-vesicles of the invention are derived/released from MSCs that have a viability of at about 90% when the extracellular vesicles are isolated. Further, the extracellular-vesicles of the invention are derived/released from MSCs that are essentially free of Mycoplasma and/or microbes. Such conditions can be tested by sterility tests (aerobic and anaerobic bacterial cultures). Further, the extracellular-vesicles of the invention are derived/released from MSCs that are essentially free of endotoxin, preferably the endotoxin level is below 0.05 EU/mL.

Further, the extracellular vesicles of the invention have a particular size. The extracellular vesicles of the invention may have a diameter of about 30 nm to about 150 nm, preferably the extracellular vesicles of the invention may have a diameter of about 40 nm to about 150 nm, more preferably the extracellular vesicles of the invention may have a diameter of about 50 nm to about 150 nm, more preferably the extracellular vesicles of the invention may have a diameter of about 60 nm to about 150 nm, more preferably the extracellular vesicles of the invention may have a diameter of about 70 nm to about 150 nm, more preferably the extracellular vesicles of the invention may have a diameter of about 80 nm to about 150 nm, more preferably at least about 90% of the extracellular vesicles of the invention may have a diameter of about 80 nm to about 150 nm, more preferably the extracellular vesicles of the invention may have a diameter of about 90 nm to about 150 nm, more preferably the extracellular vesicles of the invention may have a diameter of about 100 nm to about 150 nm, more preferably the extracellular vesicles of the invention may have a diameter of about 100 nm to about 140 nm, more preferably the extracellular vesicles of the invention may have a diameter of about 100 nm to about 130 nm, more preferably the extracellular vesicles of the invention may have a diameter of about 100 nm to about 120 nm, most preferably the extracellular vesicles of the invention may have a diameter of about 100 nm to about 115 nm.

In order to determine the size of the extracellular-vesicles of the invention, various techniques can be employed that are suitable to determine the average size of membrane vesicles. For example, nanoparticle tracking analysis (NTA) can be performed as documented in the appended examples. In order to determine the size of the vesicles, the concentration of the extracellular vesicles can be $>4\times10^{11}$ particles/mL from a starting concentration of $80\times10^{6}$ cells. Further, the extracellular vesicles may comprise >5%, >6%, >7%, >8%, >9% or >10% membrane containing vesicular structures as detected by fluorescence NTA employing PHK67 staining.

The culture medium used to culture the MSCs may comprise about 2%, preferably about 3%, more preferably about 4%, more preferably about 5%, more preferably about 6%, more preferably about 7%, more preferably about 8%, more preferably about 9% or most preferably about 10% of a cell culture supplement, such as HPL or FBS. The concentration of the cell culture supplement may also be higher than the indicated concentrations. In certain aspects of the invention, the culture medium may also be a culture medium that does not comprise a cell culture supplement, such as serum, human platelet lysate, or plasma. For example, the culture medium can be a synthetic serum-free culture medium. The synthetic serum-free culture medium is herein less preferred. In certain aspects, the culture medium may not be a synthetic (serum-free) culture medium.

As used herein, "human platelet lysate" or "HPL" refers to a light-yellow liquid that is obtained from human blood platelets after lysis. The lysis can be achieved by freeze/thaw cycle(s). The freeze/thaw cycle causes the platelets to lyse, releasing a large quantity of growth factors necessary for cell expansion. Accordingly, the HPL comprises growth factors that promote the growth of cells. The term "pHPL" refers to pooled HPL. Thus, the HPL is obtained from a pool of subjects.

As used herein, "fetal bovine serum", "FBS" or "fetal calf serum" is the blood fraction remaining after the natural coagulation of blood, followed by centrifugation to remove remaining red blood cells. Fetal bovine serum is a used serum-supplement for the in vitro cell culture of eukaryotic cells. FBS has a low level of antibodies and containing growth factors.

As used herein, "serum" in the context of the present invention is the liquid fraction of whole blood that is collected after the blood is allowed to clot. When coagulated blood (clotted blood) is centrifuged serum can be obtained as supernatant.

As used herein, "plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood), for example for at least 15 minutes at 2000 to 3000 g.

In certain aspects of the invention, the culture medium used to culture the MSCs in order to release the extracellular vesicles is essentially free of non-human (xenogenic) additives. Thus, the obtained extracellular-vesicles are essentially free of non-human xenogenic additives.

The invention further relates to a pharmaceutical composition wherein the pharmaceutical composition comprises extracellular-vesicles derived from mesenchymal stromal cells (MSCs), wherein the extracellular-vesicles are essentially free of vesicles not derived from the MSCs, and wherein the extracellular-vesicles are essentially free of heparin, and preferably wherein the extracellular-vesicles are essentially free of fibrinogen/fibrin.

In particular, the invention further relates to a pharmaceutical composition wherein the pharmaceutical composition comprises extracellular-vesicles derived from mesenchymal stromal cells (MSCs), wherein the extracellular-vesicles are essentially free of vesicles of HPL and/or FBS, and wherein the extracellular-vesicles are essentially free of heparin, and preferably wherein the extracellular-vesicles are essentially free of fibrinogen/fibrin.

The extracellular vesicles or the culture medium of the invention comprised in the pharmaceutical composition can be obtained by the methods provided herein. Accordingly, the invention may relate to a pharmaceutical composition comprising the extracellular-vesicles, the extracellular-vesicles obtained by the methods of the invention and/or the culture medium of the invention.

The invention also relates to the pharmaceutical composition, the extracellular-vesicles, the extracellular-vesicles obtained by the methods, or the culture medium of the invention for use as a medicament. In particular, the invention relates to the pharmaceutical composition, the extracellular-vesicles, or the medium comprising the extracellular vesicles for use in the treatment of one or more of the diseases and/or disorders selected from the group consisting of bone defects, tendon defects, segmental bone defects, non-unions, malunions, delayed unions, bone cysts, necroses, developmental abnormalities, conditions requiring bone augmentation, joint reconstruction, augmentation of bone-implant contact, sinus augmentation, cosmetic reconstruction, bone fusions, spinal fusion, joint fusion, tendinopathy, including tendinitis, tendonitis, tendinosis, paratendinitis, tenocynovitis, tendon overuse injury, trauma, peritendinitis, paratenonitis, tendon, ligament defects, tendon detachment, and ligament detachment from bone.

The invention also relates to the pharmaceutical composition, the extracellular-vesicles, the extracellular-vesicles obtained by the methods of the invention, or the culture medium of the invention for use in the treatment of one or more bone and tendon defects, such as segmental bone defects, non-unions, malunions or delayed unions, bone cysts, necroses or developmental abnormalities.

The invention also relates to the pharmaceutical composition, the extracellular-vesicles, the extracellular-vesicles obtained by the methods or the culture medium of the invention for use in the treatment of conditions requiring bone augmentation, such as joint reconstruction, augmentation of bone-implant contact, sinus augmentation, cosmetic reconstruction or bone fusion, such as spinal fusion or joint fusion.

The invention also relates to the pharmaceutical composition, the extracellular-vesicles, the extracellular-vesicles obtained by the methods or the culture medium of the invention for use in the treatment of tendinopathy, including tendinitis, tendonitis, tendinosis, paratendinitis, tenocynovitis, tendon overuse injury and trauma, peritendinitis, paratenonitis, and tendon or ligament defects, as well as tendon or ligament detachment from bone to improve the healing response associated with surgical repairs.

The invention also relates to the pharmaceutical composition, the extracellular-vesicles, the extracellular-vesicles obtained by the methods, or the culture medium of the invention for use in the treatment of (a) bone defect(s), tendon defect(s) and/or spinal cord injury.

The invention also relates to the pharmaceutical composition, the extracellular-vesicles, the extracellular-vesicles obtained by the methods, or the culture medium of the invention in the treatment of (a) bone defect(s), tendon defect(s) and/or spinal cord injury.

In certain aspects of the invention, the invention relates to the pharmaceutical composition, the extracellular-vesicles, the extracellular-vesicles obtained by the methods, or the culture medium of the invention in the treatment of (a) bone damage(s) and tendon damage(s). In particular aspects of the invention, the invention relates to the pharmaceutical composition, the extracellular-vesicles, the extracellular-vesicles obtained by the methods, or the culture medium of the invention in the treatment of (a) bone defect(s) and tendon defect(s). The invention also relates to the pharmaceutical composition, the extracellular-vesicles, the extracellular-vesicles obtained by the methods, or the culture medium of the invention in the repair of bone, tendon and/or spinal cord.

In particular aspects, the invention relates to the extracellular-vesicles or the extracellular vesicles obtained by the methods of the present invention, or the pharmaceutical composition comprising the extracellular-vesicles for use in the treatment of (a) bone defect(s) and tendon defect(s).

Various adult stem cells (e.g. MSCs) have been evaluated for their potential to augment tendon repair and reduce inflammation for various tendinopathies in several small and large animal models. As extracellular vesicles derived from MSCs demonstrate beneficial therapeutic effects, as also shown in the appended Examples and as documented herein, similar to those seen for MSCs themselves, the extracellular vesicles have the potential to improve tendon quality, for example, via their immunomodulatory and/or pro-angiogenic action.

As shown in the appended Examples, the extracellular-vesicles of the invention or the extracellular-vesicles obtained by the methods of the invention inhibit T-cell proliferation. Further, the extracellular-vesicles of the invention or the extracellular-vesicles obtained by the methods of the invention do essentially not inhibit alloantigen-driven mixed leukocyte reaction. Accordingly, the extracellular-vesicles of the invention or the extracellular-vesicles obtained by the methods of the invention are immunomodulatory.

In addition, extracellular vesicles derived from MSCs may augment the functional repair of tendon-to-bone insertions (e.g. rotator cuff, and Achilles tendon enthesis), for example, via the capacity to modulate osteogenic processes. Accordingly, extracellular vesicles could be used to treat diseased tendons or tendon defects. In addition, the use of extracellular vesicles eliminate some of the potential disadvantages when using active, replicating cells that may, for example, undergo mal-differentiation or mutation.

Transplantation of bone marrow stem cells into spinal cord lesions enhances axonal regeneration and promotes functional recovery in animal studies and the mechanisms by which MSCs might promote spinal cord repair following transplantation have been extensively investigated. Animal studies have demonstrated that transplanted MSCs modify the inflammatory environment in the acute setting and reduce the effects of the inhibitory scar tissue in the sub-acute/chronic setting to provide a permissive environment for axonal extension. In addition, grafted cells may provide a source of secreted paracrine factors to enhance axonal elongation across spinal cord lesions. Preliminary clinical data indicate that autologous bone marrow cell transplantation can be used to treat patients with SCI without any immediate serious complications (Morita et al. 2016; Wright, et al. 2011).

For almost two decades, cell-based therapies have been tested in modern regenerative medicine to either replace or regenerate human cells, tissues, or organs and restore normal function. There is increasing evidence that the success of cell-based SCI therapy is due mainly to secreted factors rather than to cell implantation per se. These secreted factors (or secretome) include a variety of proteins, lipids, microRNAs, and extracellular vesicles. The MSC secretome has been investigated in pre-clinical settings and other cell types, such as peripheral blood mononuclear cells (PBMCs), are also capable of releasing biologically active paracrine factors that exert beneficial regenerative effects. The PBMC-secretome had therapeutic effects in a rat SCI contusion model and its possible underlying mechanisms. Rats treated with PBMC-secretome showed substantially improved functional recovery, attenuated cavity formation, and reduced acute axonal injury compared to control animals. Histological evaluation revealed higher vascular density in the spinal cords of treated animals and showed angiogenic properties ex vivo in aortic rings and spinal cord tissue.

Accordingly, secreted factors, including extracellular vesicles, can mitigate the pathophysiological processes of secondary damage after SCI and improve functional outcomes. (Haider et al. 2015; Beer et al. 2016). Therefore, the extracellular vesicles of the invention can be used in the treatment of spinal cord injury.

As used herein, the term "bone defect" may refer to a disease and/or disorder selected from the group consisting of a segmental bone defect, non-union, malunion, delayed union, bone cyst, necrose, developmental abnormality, condition requiring bone augmentation, joint reconstruction, augmentation of bone-implant contact, sinus augmentation, bone fusion, spinal fusion, and joint fusion. The term "bone defect" may refer to one or more diseases and/or disorders selected from the group consisting of osteoporosis with pathological fracture (e.g. M80), disorders of continuity of bone (e.g. M84), fracture of bone following insertion of orthopaedic implant, joint prosthesis, or bone plate (e.g. M96.6), complications of internal orthopaedic prosthetic devices, implants and grafts (e.g. T84), osteomyelitis (e.g. M86), and osteonecrosis (e.g. M87). Exemplary classes of the International Statistical Classification of Diseases and Related Health Problems 10th Revision (ICD-10)-WHO Version for 2016 are also given herein in brackets. Such classes are exemplary and should not to be conceived as limiting. Further, all the diseases and/or disorders provided in sub-classes of the provided classes, and if suitable provided in the antecedent class, may also be included into the particular disease and/or disorder.

As used herein, the term "tendon defect" may refer to a disease and/or disorder selected from the group consisting of tendinopathy, tendinitis, tendonitis, tendinosis, paratendinitis, tenosynovitis, tendon overuse injury, trauma, peritendinitis, paratenonitis, tendon detachment from bone, and ligament detachment from bone. The tendon defect may also refer to a ligament defect. The term "tendon defect" may also refer to one or more diseases and/or disorders selected from the group consisting of synovitis and tenosynovitis (e.g. M65), Spontaneous rupture of synovium and tendon (e.g. M66), other disorders of synovium and tendon (e.g. M67), shoulder lesions (e.g. M75), in particular rotator cuff syndrome (e.g. M75.1), Enthesopathies of lower limb (e.g. M76), and other enthesopathies (e.g. M77). Accordingly, a tendon defect is an enthesopathy comprising a tendon enthesis defect, as treated in the exemplary part. An exemplary enthesopathy is a tendon enthesis defect. The treatment of a tendon enthesis defect is demonstrated in Example 3. Accordingly, the pharmaceutical composition provided herein may be employed in the treatment of enthesopathies, in particular tendon enthesis defects.

The treatment of spinal cord injury is herein less preferred. The skilled person can evaluate by standard medical examination whether a treatment has a beneficial effect or at least has no deleterious effect on the patient. Thus, the skilled person knows that a specific treatment is only applied if the patient has a need for the treatment. As used herein, the term "spinal cord injury" or "SCI" refers to damage to the spinal cord that causes changes in its function, either temporary or permanent. The spinal cord injury as used herein may involve a damage of the spine. The spinal cord injury may also refer to diseases and/or disorders provided in S14, S24 and/or S34 and the corresponding sub-classes of the International Statistical Classification of Diseases and Related Health Problems 10th Revision (ICD-10)-WHO Version for 2016.

Spinal cord injury (SCI) may disrupt the neuronal connections between the brain and the periphery, resulting in a loss of function. Spinal cord injuries can be classified based on function or on where the damage occurred. The spinal cord is surrounded by protective rings of bone called vertebrae. The vertebrae and spinal nerves are organized into segments, starting at the top of the spinal cord. Within each segment, the vertebrae and nerves are numbered. The segments are as follows: Cervical. The neck area contains 7 cervical vertebrae (C1 through C7) and 8 cervical nerves (C1 through C8). Cervical SCIs usually cause loss of function in the chest, arms, and legs. Cervical injuries can also affect breathing and bowel and bladder control. Thoracic. The chest area contains 12 thoracic vertebrae (T1 through T12) and 12 thoracic nerves (T1 through T12). The first thoracic vertebra, T1, is the vertebra where the top rib attaches to the spine. Thoracic SCIs usually affect the chest and the legs. Injuries to the upper thoracic area can affect breathing. Thoracic injuries can also affect bowel and bladder control. Lumbar. The lumbar area (between the chest area and the pelvis) contains 5 lumbar vertebrae (L1 through L5) and 5 lumbar nerves (L1 through L5). Lumbar SCIs usually affect the hips and legs. Lumbar injuries can also affect bowel and bladder control. Sacral. The sacral area (from the pelvis to the end of the spine) contains 5 sacral vertebrae (S1 through S5) and 5 sacral nerves (S1 through S5). Sacral SCIs also usually affect the hips and legs. Injuries to the upper sacral area can also affect bowel and bladder control.

As used herein, the term SCI may refer to cervical SCIs, thoracic SCIs, lumbar SCIs and/or sacral SCIs.

As used herein, the SCI may be complete and incomplete, and an incomplete injury is further classified into four subsections. The American Spinal Injury Association (ASIA) classifies SCIs as follows: Classification of spinal cord injuries:

A: Complete: No feeling or movement of the areas of the body that are controlled by the lowest sacral nerves. People with complete SCI do not have control of bowel and bladder function.

B: Incomplete: Feeling but no movement below the level of injury, including sacral segments that control bowel and bladder function.

C: Incomplete: Feeling and movement below the level of injury. More than half of key muscles can move, but not against gravity. Moving against gravity means moving up, for example, raising the hand to mouth when sitting up.

D: Incomplete: Feeling and movement below the level of injury. More than half of key muscles can move against gravity.

E: Feeling and movement are normal. (Scores as determined by American Spinal Injury Association (ASIA))

The invention also relates to the extracellular-vesicles, the pharmaceutical composition comprising the extracellular-vesicles, or the pharmaceutical composition for use in the treatment of condition, pathological condition, disease and/or disorder for the induction/stimulation of bone and/or tendon formation.

The "treatment" of a disorder or disease may also lead to a partial response (e.g., amelioration of symptoms) or complete response (e.g., disappearance of symptoms) of the subject/patient suffering from the disorder, disease or defect. The term treatment also includes the prevention of the defect, disease or disorder. A partial or complete response may be followed by a relapse. It is to be understood that a subject/patient may experience a broad range of responses to a treatment (e.g., the exemplary responses as described herein above). The treatment of a disorder or disease may, inter alia, comprise curative treatment (preferably leading to a complete response and eventually to healing of the defect, disorder, or disease) and palliative treatment (including symptomatic relief). Thus, the term "treatment" means obtaining a desired pharmacological and/or physiological effect. The effect may also be prophylactic in terms of completely or partially preventing a disease/medical condition/disorder or symptom thereof and/or may be therapeutic in terms of partially or completely curing a disease/medical condition/disorder and/or adverse effect attributed to the disease/medical condition/disorder. It is to be understood that a defect, disorder or disease to be prevented in accordance with the present invention has not been diagnosed or cannot be diagnosed in the patient/subject (for example, the patient/subject does not show any clinical or pathological symptoms). Thus, the term "prevention" comprises the use of compounds of the present invention before any clinical and/or pathological symptoms are diagnosed or determined or can be diagnosed or determined by the attending physician.

Further, the invention also relates to a cosmetic composition comprising the extracellular vesicles of the invention, the extracellular vesicles obtained by the methods of the invention, and/or the culture medium of the invention. The cosmetic composition of the invention may be used in cosmetic reconstructions. An exemplary cosmetic reconstruction might be the reconstruction in the maxillofacial area.

The invention further relates to a method of treatment or a cosmetic method. In the method of treatment, the method comprises the administration to a subject in need of such treatment a pharmaceutical active/effective amount of the pharmaceutical composition. The method of treatment provided herein is suitable for the treatment of the herein above and below defined diseases and/or disorders.

In the cosmetic method, the method comprises the administration to a subject an active amount of the cosmetic composition.

The pharmaceutical composition or the cosmetic composition of the invention may comprise the extracellular vesicles of the invention, the extracellular vesicles obtained by the methods of the invention, and/or the culture medium of the invention and may further comprise one or more Bone Morphogenic Proteins (or a fragment(s) thereof) and/or PDGF (or a fragment thereof).

As used herein, "Bone Morphogenetic Protein" or "BMP" is a signaling molecule that belongs to the Transforming Growth Factor-β (TGF-β) superfamily of proteins. Particularly, the term BMP means BMP2, BMP4, BMP6, BMP7, BMP12, BMP13 and BMP14. BMP2, BMP4, BMP6, and BMP7 are documented to be osteogenic (Katagiri et al., 2016). BMP7 (Klatte-Schulz et al., 2016), BMP12, BMP13 and BMP14 are documented to be tenogenic (Docheva et al., 2015).

As used herein, "Platelet-derived growth factor" or "PDGF" is a growth factor that mediates/regulates cell growth and division.

The pharmaceutical composition or the cosmetic composition of the invention may comprise one or more Bone Morphogenic Proteins. Further, the pharmaceutical composition or the cosmetic composition of the invention may comprise one or more Bone Morphogenic Proteins and PDGF. Further, the pharmaceutical composition or the cosmetic composition of the invention may comprise PDGF. Further, the pharmaceutical composition or the cosmetic composition of the invention may comprise one or more Bone Morphogenic Proteins and/or PDGF, wherein the one or more Bone Morphogenic Protein(s) (BMP(s)) are selected from the group consisting of Bone Morphogenic Protein 2 (BMP2), Bone Morphogenic Protein 3 (BMP3), Bone Morphogenic Protein 4 (BMP4), Bone Morphogenic Protein 5 (BMP5), Bone Morphogenic Protein 6 (BMP6), Bone Morphogenic Protein 7 (BMP7), Bone Morphogenic Protein 8a (BMP8a), Bone Morphogenic Protein 8b (BMP8b), Bone Morphogenic Protein 12 (BMP12), Bone Morphogenic Protein 13 (BMP13), and Bone Morphogenic Protein 14 (BMP14).

In certain aspects, the pharmaceutical composition or the cosmetic composition of the invention may comprise one or more Bone Morphogenic Proteins selected from the group consisting of Bone Morphogenic Protein 2 (BMP2), Bone Morphogenic Protein 3 (BMP3), Bone Morphogenic Protein 4 (BMP4), Bone Morphogenic Protein 5 (BMP5), Bone Morphogenic Protein 6 (BMP6), Bone Morphogenic Protein 7 (BMP7), Bone Morphogenic Protein 8a (BMP8a), Bone Morphogenic Protein 8b (BMP8b), Bone Morphogenic Protein 12 (BMP12), Bone Morphogenic Protein 13 (BMP13), and Bone Morphogenic Protein 14 (BMP14).

In certain aspects, the pharmaceutical composition or the cosmetic composition of the invention may comprise the extracellular vesicles of the invention, BMP2 and BMP7.

The pharmaceutical composition or the cosmetic composition of the invention may further comprise one or more Bone Morphogenic Proteins and/or PDGF, wherein the one or more Bone Morphogenic Protein(s) (BMP(s)) are selected from the group consisting of BMP2, BMP4, BMP6, BMP7, BMP 12, BMP 13, and BMP 14.

Particularly, the pharmaceutical composition or the cosmetic composition of the invention may comprise a Bone Morphogenic Protein. In particular aspects, the pharmaceutical composition or the cosmetic composition of the invention may comprise BMP2.

Accordingly, the pharmaceutical composition or the cosmetic composition may comprise the extracellular vesicles of the invention, the extracellular vesicles obtained by the methods of the invention, and/or the culture medium of the invention comprising the extracellular-vesicles and one BMP. Particularly, the pharmaceutical composition or the cosmetic composition may comprise the extracellular vesicles of the invention, the extracellular vesicles obtained by the methods of the invention, and/or the culture medium of the invention comprising the extracellular-vesicles and BMP2.

Further, the pharmaceutical composition or the cosmetic composition of the invention may comprise BMP4. Further, the pharmaceutical composition or the cosmetic composition of the invention may comprise BMP6. Further, the pharmaceutical composition or the cosmetic composition of the invention may comprise BMP7. Further, the pharmaceutical composition or the cosmetic composition of the invention may comprise BMP12. Further, the pharmaceutical composition or the cosmetic composition of the invention may comprise BMP13. Further, the pharmaceutical composition or the cosmetic composition of the invention may comprise BMP14. Further, the pharmaceutical composition or the cosmetic composition of the invention may comprise PDGF.

The BMP(s) and PDGF can be obtained recombinantly. Particularly, the BMP(s) and PDGF are recombinant human BMP(s) and/or PDGF.

The skilled person knows in which cases a combination of the extracellular-vesicles with BMP(s) and/or PDGF is beneficial for the patient. The beneficial treatment can be determined by standard examination.

The pharmaceutical composition, the cosmetic composition, or the extracellular-vesicles of the invention may be comprised in a scaffold. Accordingly, it is understood herein that the pharmaceutical composition or the cosmetic composition can comprise a scaffold and wherein the extracellular-vesicles and/or the further components comprised in the pharmaceutical composition or the cosmetic composition are included in this scaffold. As used herein, the scaffold is a matrix and the matrix is formulated into a sponge-like material that is suitable for an implantable formulation. The matrices of the present invention may be formed into any shape. The matrix can be selected of the group consisting of a ceramic implant, a polymer, hydrogel, bone matrix and demineralized bone matrix. For example, the matrix can be a granular or three-dimensionally formed ceramic implant, e.g. βTCP, HA, or combinations thereof. The matrix can also be a natural or synthetic, resorbable polymer or hydrogel, including demineralized bone matrix of human or animal origin. The matrix can be degradable. That is, the matrix dissolves itself after administration to the subject and releases its components. The pharmaceutical composition or the cosmetic composition may be administered in a sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988). Sustained release pharmaceutical composition also include liposomally entrapped compound.

The scaffold and the matrix can be shaped as a mat, cube, cylinder, block or an anatomical site and can be formed of a powder, granules, or structurally stable, three dimensional structure.

The pharmaceutical composition or the cosmetic of the invention may comprise a pharmaceutically acceptable carrier. By "pharmaceutically acceptable carrier" is meant a non-toxic solid, semisolid or liquid filler, diluent, encapsulating material or formulation auxiliary of any type. Examples of such carriers include water, saline, Ringer's solution, and dextrose solution. Non aqueous vehicles such as fixed oils and ethyl oleate are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

Furthermore, it is envisaged that the pharmaceutical composition or cosmetic composition of the invention might comprise further biologically or pharmaceutically active agents, depending on the intended use of the pharmaceutical composition. These further biologically or pharmaceutically active agents may be e.g. antibodies, antibody fragments, hormones, growth factors, enzymes, binding molecules, cytokines, chemokines, nucleic acid molecules and drugs.

The pharmaceutical composition or cosmetic composition of the invention comprises the extracellular vesicles, the extracellular vesicles obtained by the methods, and/or the culture medium of the invention, e.g. in a dose. A suitable dose may not induce DNA damage or hemolysis, and may reveal no detectable toxicity. Suitable doses of extracellular vesicles are known, e.g. (Maji et al., 2016).

The dose of the extracellular vesicles or the extracellular vesicles comprised in the pharmaceutical composition or cosmetic composition of the invention may be about, $2\times10^{19}$ particles. The particle number or dose of the extracellular vesicles may be determined by NTA. A dose of the extracellular vesicles may also be equivalent to $20\times10^{6}$ MSCs (cell equivalent or CE). The dose of the extracellular vesicles of the invention may comprise between about $1\times10^{7}$ to about $1\times10^{12}$ particles/EVs from MSCs or CE of EVs of about $1\times10^{8}$. The dose of the extracellular vesicles of the invention may comprise between about $1\times10^{9}$ to about $1\times10^{12}$ particles. The dose of the extracellular vesicles of the invention may comprise about $2\times10^{7}$ particles. The dose of the extracellular vesicles may also be higher or lower than indicated above as long as the dose induces bone and/or tendon formation.

The pharmaceutical composition or cosmetic composition of the invention may further comprise a dose of the one or more BMP(s) and/or PDGF. Particularly, the dose of the BMP or the PDGF may be below 12 mg. More particularly, the dose of the BMP or the PDGF may be between about 10 μg to about 11 mg. More particularly, the dose of the BMP or the PDGF may be between about 10 μg to about 10 mg. The herein provided doses may refer to a total dose of the different BMP(s) and/or PDGF (sum of all doses of different components of BMP(s) and/or PDGF). For example, the total dose of all the BMPs and/or PDGF may sum up between about 10 μg to about 11 mg.

As used herein, the term "dose" or "unit dose" means the amount of a medication that is administered or is to be administered to a subject, e.g., a human, in a single dose.

The dose of the BMP(s) and/or the PDGF may be between about 10 μg to about 10 mg. Particularly, the dose of the BMP(s) may be between about 10 μg to about 10 mg. Particularly, the dose of the BMP may be between about 10 μg to about 10 mg. Particularly, the dose of the BMP(s) and/or the PDGF may be between about 10 μg to about 10 mg. The dose of the BMP(s) may be between about 10 μg to about 10 mg. The dose of the BMP may be between about 10 μg to about 10 mg.

In particular aspects of the invention, the following doses refer to the dose of a BMP, e.g. BMP2. The dose of the BMP(s) may be between about 10 μg to about 10 mg. Preferably, the dose of the BMP(s) (e.g. of BMP2) may be below 12 mg. More preferably, the dose of the BMP(s) (e.g. of BMP2) may be between about 10 μg to about 5 mg, more preferably between about 10 μg to about 1 mg, more preferably between about 10 μg to about 0.9 mg, more preferably between about 10 μg to about 0.9 mg, more preferably between about 50 μg to about 0.9 mg, more preferably between about 100 μg to about 0.9 mg, more preferably between about 200 μg to about 0.9 mg, more preferably between about 300 μg to about 900 μg, more preferably between about 375 μg to about to about 900 μg, more preferably between about 375 μg to about to about 600 μg.

The dose of the BMP(s) (e.g. of BMP2) may be less than about 12 mg, more preferably less than about 11 mg, more preferably less than about 10 mg, more preferably less than about 9 mg, more preferably less than about 8 mg, more preferably less than about 7 mg, more preferably less than about 6 mg, more preferably less than about 5 mg, more preferably less than about 4 mg, more preferably less than about 3 mg, more preferably less than about 2 mg, more preferably less than about 1 mg, more preferably less than about 900 μg, more preferably less than about 700 μg, more preferably less than about 500 μg, or more preferably less than about 400 μg, most preferably the dose of the BMP(s) (e.g. of BMP2) may be 375 μg. In preferred aspects of the invention, the dose of the BMP may be about 375 μg. In most preferred aspects of the invention, the dose of the BMP2 may be about 375 μg.

The dose may also be referred to in relation to the body weight of a subject. Example 1 demonstrates that 1 μg of the pharmaceutical composition of the invention show the beneficial effect in a rat. A rat can be estimated to have an average weight of 200 g. The average weight of a human subject can be estimated to be 75 kg. Accordingly, the skilled person can calculate appropriate doses in relation to the weight of a subject.

The dose of the one or more BMPs (e.g. of BMP2) and/or the PDGF may be lower than 160 μg/kg. The dose of the one or more BMPs (e.g. of BMP2) and/or the PDGF may be between about 130 ng/kg to about 130 μg/kg. Particularly, the dose of the one or more BMPs (e.g. of BMP2) may be lower than 160 μg/kg or may be between about 130 ng/kg to about 130 μg/kg. More particularly, the dose of the one BMP (e.g. of BMP2) may be lower than 160 μg/kg or may be between about 130 ng/kg to about 130 μg/kg.

In particular aspects of the invention, the dose of the one or more BMPs (e.g. of BMP2) may be between about 130 ng/kg to about 100 μg/kg, more preferably between about 130 ng/kg to about 50 μg/kg, more preferably between about 200 ng/kg to about 50 μg/kg, more preferably between about 300 ng/kg to about 50 μg/kg, more preferably between about 500 ng/kg to about 50 μg/kg, more preferably between about 750 ng/kg to about 50 μg/kg, more preferably between about 1 μg/kg to about 50 μg/kg, more preferably between about 1 μg/kg to about 40 μg/kg, more preferably between about 1 μg/kg to about 30 μg/kg, more preferably between about 1 μg/kg to about 20 μg/kg, more preferably between about 1 μg/kg to about 15 μg/kg, most preferably between about 2 μg/kg to about 10 μg/kg.

More preferably, the dose of the one or more BMPs (e.g. of BMP2) may be about 1 μg/kg, more preferably about 2 μg/kg, more preferably about 3 μg/kg, more preferably about 4 μg/kg, or most preferably about 5 μg/kg.

In preferred aspects of the invention, the dose of the BMP may be about 5 μg/kg. In most preferred aspects of the invention, the dose of the BMP2 may be about 5 μg/kg.

The pharmaceutical compositions or the cosmetic composition provided herein can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently.

As used herein, an "effective amount", "active amount", or a "therapeutically effective amount" of a compound or composition disclosed herein is an amount of such compound or composition that is sufficient to effect beneficial or desired results as described herein when administered to a subject. Effective dosage forms, modes of administration, and dosage amounts are as disclosed herein or as modified by a medical professional. It is understood by the skilled person that the dosage amount will vary with the route of administration, the rate of excretion, the duration of the treatment, the identity of any other drugs being administered, the age and size of the subject, and like factors well known in the arts of medicine. A suitable dose of a composition according to the invention will be that amount of the composition, which is the lowest dose effective to produce the desired effect, i.e. a low dose. The effective dose of a composition of the present invention is described above and demonstrated below. The pharmaceutical composition, the cosmetic composition, the extracellular vesicles, the extracellular vesicles obtained by the methods, or the culture medium of the invention may be administered or may to be administered by different ways.

In certain aspects of the invention, the pharmaceutical composition, the cosmetic composition, the extracellular vesicles, the extracellular vesicles obtained by the methods, or the culture medium of the invention is administered or is to be administered to the target site, e.g. the traumatic and/or disordered area. The traumatic and/or disordered area may refer to area where the bone and/or the tendon has a defect, e.g. a fracture or rupture.

In particular aspects, the pharmaceutical composition or the cosmetic composition of the invention is administered or is to be administered to the target site, e.g. the traumatic and/or disordered area.

In preferred aspects of the invention, the dose of the pharmaceutical composition or the cosmetic composition of the invention is or is to be administered to the traumatic and/or disordered area.

In certain aspects, the pharmaceutical composition, the cosmetic composition, the extracellular vesicles, the extracellular vesicles obtained by the methods, or the culture medium of the invention is administered or is to be administered intraosseously, parenterally, subcutaneously, intravenously, intraarterially, intraperitoneally, topically, and, particularly for local treatment, intralesional administration. In preferred aspects, the pharmaceutical composition, the cosmetic composition, the extracellular vesicles, the extracellular vesicles obtained by the methods, or the culture medium of the invention is administered or is to be administered into the bone, tendon, and/or cartilage.

Parenteral administrations include intraperitoneal, intramuscular, intradermal, subcutaneous, intravenous or intraarterial administration.

The administration of the herein provided compositions may, inter alia, comprise an administration twice daily, every day, every other day, every third day, every forth day, every fifth day, once a week, once every second week, once every third week, once every month, etc.

In particular aspects of the invention, the pharmaceutical composition, the cosmetic composition, the extracellular vesicles, the extracellular vesicles obtained by the methods, or the culture medium of the invention is/are administered once to the subject. In preferred aspects of the invention, the dose of the pharmaceutical composition or the cosmetic composition of the invention is or is to be administered as a single dose.

An intravenous bag solution may also be employed. The length of treatment needed to observe changes and the interval following treatment for responses to occur appears to vary depending on the desired effect. The particular amounts may be determined by conventional tests which are well known to the person skilled in the art.

The components of the pharmaceutical composition to be used for therapeutic administration must be sterile. Sterility is readily accomplished by filtration through sterile filtration membranes (e.g., 0.2 micron membranes). Therapeutic components of the pharmaceutical composition generally are placed into a container having a sterile access port, for example, an intravenous solution bag or vial having a stopper pierceable by a hypodermic injection needle.

The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic Water-for-Injection.

As used herein, the term "mesenchymal stem cells", or "MSCs" refer to multipotent stromal cells that can differentiate into a variety of cell types, including osteoblasts (bone cells), chondrocytes (cartilage cells), myocytes (muscle cells) and adipocytes (fat cells). In particular aspects of the invention, the MSCs are umbilical cord-derived mesenchymal stromal cells (UCMSCs) and/or bone marrow-derived mesenchymal stromal cells (BMSCs). In preferred aspects of the invention, the MSCs are umbilical cord-derived mesenchymal stromal cells (UCMSCs). In other words, in preferred aspects of the invention, the extracellular-vesicles are derived from umbilical cord-derived mesenchymal stromal cells (UCMSCs).

The invention also relates to mesenchymal stromal cells (MSCs) that are comprised and/or cultured in a culture medium that is essentially free of vesicles not derived from the MSCs, and preferably wherein the culture medium is essentially free of heparin and/or fibrinogen.

In particular aspects, wherein the MSCs have an improved osteogenic differentiation potential (at least more than 10% of the reference) compared to the osteogenic differentiation potential of MSCs that are comprised and/or cultured in a culture medium that is essentially free of heparin, and preferably that is essentially free of fibrinogen; and/or wherein the MSCs have a similar (+/−10% of the reference) or equal adipogenic differentiation potential compared to the adipogenic differentiation potential of MSCs that are comprised and/or cultured in a culture medium that is essentially free of heparin, and preferably that is essentially free of fibrinogen.

The MSCs of the invention may be characterized by:

≥90% of cells have CD105 expression;
≥90% of cells have CD73 expression;
≥90% of cells have CD90 expression;
≤2% of cells have CD14 expression;
≤2% of cells have CD45 expression;
≤2% of cells have CD34 expression;
≤2% of cells have CD19 expression; and
≤1% of cells have MHC Class II (HLA-DR) expression.

The mesenchymal stromal cells (MSCs) of the invention that are comprised and/or cultured in a culture medium, wherein the fibrinogen and the vesicles comprised in the culture medium prior to the culturing of the MSCs were removed, and preferably wherein the culture medium was supplemented with a cell culture supplement comprising vesicles.

The invention also relates to a culture medium, wherein the culture medium comprises extracellular-vesicles derived from mesenchymal stromal cells (MSCs), and wherein the extracellular-vesicles are essentially free of vesicles not derived from the MSCs, and preferably wherein the culture medium is essentially free of heparin and preferably fibrinogen.

In particular aspects of the culture medium the fibrinogen and the vesicles comprised in the culture medium prior to culturing of the MSCs were removed, and preferably wherein the culture medium was supplemented with a cell culture supplement comprising vesicles.

The invention further relates to a kit comprising the components provided herein to obtain the extracellular-vesicles of the invention. The kit may further comprise components to test whether the extracellular vesicles are vesicles according to the present invention. For example, as described above and below, the means may be comprised to analyze the miRNA profile, the cell surface markers and or the protein content. The kit may also comprise the extracellular vesicles of the invention, the culture medium of the invention, and/or the MSCs of the invention, and may further comprise the BMP(s) and/or the PDGF.

As used herein, "essentially free" of a particular component means that less than about 5%, preferably less than about 1%, more preferably less than about 0.5%, more preferably less than about 0.1%, or most preferably less than about 0.05% of this particular component is comprised in the fraction, medium or extracellular vesicles.

As used herein, "cell" refers to a living body which is a structural unit of tissue of a multicellular organism. A cell is surrounded by a membrane structure which isolates it from the outside, has the capability of self-replicating, and has genetic information and a mechanism for expressing it. Cells used herein may be naturally-occurring cells or artificially modified cells (e.g., fusion cells, genetically modified cells, etc.).

As used herein, the term "stem cell" refers to a cell capable of self-replication and pluripotency.

The term "method" refers to manners, means, techniques and procedures for accomplishing a given task including, but not limited to, those manners, means, techniques and procedures either known to, or readily developed from known manners, means, techniques and procedures, by practitioners of the chemical, biological and biophysical arts.

The terms "polypeptide", "peptide" and "protein" are used herein interchangeably and refer to a polymer of two or more amino acids linked via amide or peptide bonds that are formed between an amino group of one amino acid and a carboxyl group of another amino acid. Preferably, a peptide bond is formed between the α-amino group of one amino acid and the α-carboxyl group of another amino acid. The amino acids comprised in the peptide or protein, which are also referred to as amino acid residues, may be selected from the 20 standard proteinogenic α-amino acids (i.e., Ala, Arg, Asn, Asp, Cys, Glu, Gln, Gly, His, Ile, Leu, Lys, Met, Phe, Pro, Ser, Thr, Trp, Tyr, and Val).

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of". Thus, the terms "comprising"/"including"/"having" mean that any further component (or likewise features, integers, steps and the like) can/may be present.

The term "consisting of" means that no further component (or likewise features, integers, steps and the like) is present.

The term "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

Thus, the term "consisting essentially of" means those specific further components (or likewise features, integers, steps and the like) can be present, namely those not materially affecting the essential characteristics of the composition, device or method. In other words, the term "consisting essentially of" (which can be interchangeably used herein with the term "comprising substantially"), allows the presence of other components in the composition, device or method in addition to the mandatory components (or likewise features, integers, steps and the like), provided that the essential characteristics of the device or method are not materially affected by the presence of other components.

The term "about" preferably refers to ±10% of the indicated numerical value, more preferably to ±5% of the indicated numerical value, and in particular to the exact numerical value indicated.

As used herein, the term "about" refers to ±10% of the indicated numerical value, and in particular to ±5% of the indicated numerical value. Whenever the term "about" is used, a specific reference to the exact numerical value indicated is also included. If the term "about" is used in connection with a parameter that is quantified in integers, such as the number of nucleotides in a given nucleic acid, the numbers corresponding to ±10% or ±5% of the indicated numerical value are to be rounded to the nearest integer. For example, the expression "about 25 amino acids" refers to the range of 23 to 28 amino acids, in particular the range of 24 to 26 amino acids, and preferably refers to the specific value of 25 amino acids.

Unless otherwise indicated, established methods of recombinant gene technology were used as described, for example, in Sambrook, Russell "Molecular Cloning, A Laboratory Manual", Cold Spring Harbor Laboratory, N.Y. (2001)) which is incorporated herein by reference in its entirety.

The given definitions and explanations are also applicable to these items and apply mutatis mutandis. In accordance with the above, the present invention relates to the following items in certain embodiments.

1. Extracellular-vesicles derived from mesenchymal stromal cells (MSCs), a pharmaceutical composition comprising extracellular-vesicles derived from mesenchymal stromal cells (MSCs), or the pharmaceutical composition for use in the treatment of (a) bone defect (s) and tendon defect(s),
   wherein the extracellular-vesicles are essentially free of vesicles not derived from the MSCs, and wherein the extracellular-vesicles are essentially free of heparin.
2. The extracellular-vesicles of item 1, the pharmaceutical composition of item 1, or the pharmaceutical composition for use of item 1, wherein the extracellular-vesicles comprise:

| | |
|---|---|
| 100% of | hsa-miR-146a-5p, |
| at least about 50% of | hsa-miR-92a-3p, |
| at least about 15% of | hsa-miR-21-5p, |
| at least about 10% of | hsa-miR-148a-3p, |
| at least about 15% of | hsa-miR-221-3p, |
| at least about 5% of | hsa-let-7i-5p, and |
| at least about 5% of | hsa-let-7f-5p, |

wherein the level of hsa-miR-146a-5p is set to 100%.
3. The extracellular-vesicles of item 1 or 2, the pharmaceutical composition of item 1 or 2, or the pharmaceutical composition for use of item 1 or 2,
   wherein the extracellular-vesicles are essentially free of fibrinogen.
4. The extracellular-vesicles of any one of items 1 to 3, the pharmaceutical composition of any one of items 1 to 3, or the pharmaceutical composition for use of any one of items 1 to 3,
   wherein the vesicles not derived from the MSCs are vesicles that are comprised in a culture medium prior to the culturing of the MSCs, such as vesicles that are comprised in serum, human platelet lysate, or plasma.
5. The pharmaceutical composition of any one of items 1 to 4, or the pharmaceutical composition for use of any one of items 1 to 4,
   wherein the pharmaceutical composition comprises one or more Bone Morphogenic Proteins and/or PDGF, wherein the one or more Bone Morphogenic Proteins are selected from the group consisting of Bone Morphogenic Protein 2 (BMP2), Bone Morphogenic Protein 3 (BMP3), Bone Morphogenic Protein 4 (BMP4), Bone Morphogenic Protein 5 (BMP5), Bone Morphogenic Protein 6 (BMP6), Bone Morphogenic Protein 7 (BMP7), Bone Morphogenic Protein 8a (BMP8a), Bone Morphogenic Protein 8b (BMP8b), Bone Morphogenic Protein 12 (BMP12), Bone Morphogenic Protein 13 (BMP13), and Bone Morphogenic Protein 14 (BMP14).
6. The pharmaceutical composition of any one of items 1 to 5, or the pharmaceutical composition for use of any one of items 1 to 5,
   wherein the pharmaceutical composition comprises BMP2.
7. The pharmaceutical composition of any one of items 1 to 6, or the pharmaceutical composition for use of any one of items 1 to 6,
   wherein the dose of the BMP(s), preferably of the BMP2, is between about 10 μg to about 10 mg.
8. The pharmaceutical composition of any one of items 1 to 7, or the pharmaceutical composition for use of any one of items 1 to 7,
   wherein the dose of the BMP, preferably of the BMP2, is about 375 μg.
9. The extracellular-vesicles of any one of items 1 to 4, the pharmaceutical composition of any one of items 1 to 8, or the pharmaceutical composition for use of any one of items 1 to 8,
   wherein the extracellular-vesicles or the pharmaceutical composition is to be administered to the traumatic and/or disordered area.
10. The extracellular-vesicles of any one of items 1 to 4 and 9, the pharmaceutical composition of any one of items 1 to 9, or the pharmaceutical composition for use of any one of items 1 to 9,
    wherein the extracellular-vesicles comprise at least about 99.5% of extracellular-vesicles derived from the MSCs.
11. The extracellular-vesicles of any one of items 1 to 4, 9 and 10, the pharmaceutical composition of any one of items 1 to 10, or the pharmaceutical composition for use of any one of items 1 to 10,
    wherein the extracellular-vesicles are essentially free of hsa-miR-133, hsa-miR-135, hsa-miR-204, hsa-miR-211, hsa-miR-17, and hsa-miR-106.

12. The extracellular-vesicles of any one of items 1 to 4, 9 to 11, the pharmaceutical composition of any one of items 1 to 11, or the pharmaceutical composition for use of any one of items 1 to 11,
 wherein the extracellular vesicles are positive for CD9, CD81 and TSG101, and optionally are negative for GM130.
13. The extracellular-vesicles of any one of items 1 to 4, 9 to 12, the pharmaceutical composition of any one of items 1 to 12, or the pharmaceutical composition for use of any one of items 1 to 12,
 wherein the MSCs are positive for the surface markers CD73, CD90 and CD105, and optionally wherein the MSCs are negative for the surface markers CD14, CD19, CD34, CD45 and HLA-DR.
14. The extracellular-vesicles of any one of items 1 to 4, 9 to 13, the pharmaceutical composition of any one of items 1 to 13, or the pharmaceutical composition for use of any one of items 1 to 13,
 wherein the pharmaceutical composition or the extracellular vesicles are in a scaffold.
15. Method for obtaining extracellular-vesicles derived from mesenchymal stromal cells (MSCs), wherein the method comprises:
 (i) removing fibrinogen from a culture medium, wherein no heparin is added to the culture medium, and removing vesicles from the culture medium,
 (ii) culturing the MSCs in the culture medium of step (i), and
 (iii) isolating the extracellular-vesicles derived from the MSCs from the medium.

The present invention is further described by reference to the following non-limiting figures and examples. The Figures show:

FIG. 1: miRNA sequencing results for EVs. miRNA 146a-5p is used as the reference miRNA since this miRNA consistently shows the highest values in EVs prepared according to the procedure described further above. The values are set to 100%—all other percentages are given in relation to this value and do not reflect total content percentages.

FIG. 2: NTA (Nanoparticle tracking analysis). Amount and size of particles were measured using a ZetaView Nanoparticle Tracking Analyzer. Particle size was calculated according to the Stokes-Einstein equation by the ZetaView software.

FIG. 3: 3D μCT reconstructions of the defect region for two representative specimens (worst and best result) of each treatment group 6 weeks after surgery.

Figure 4:
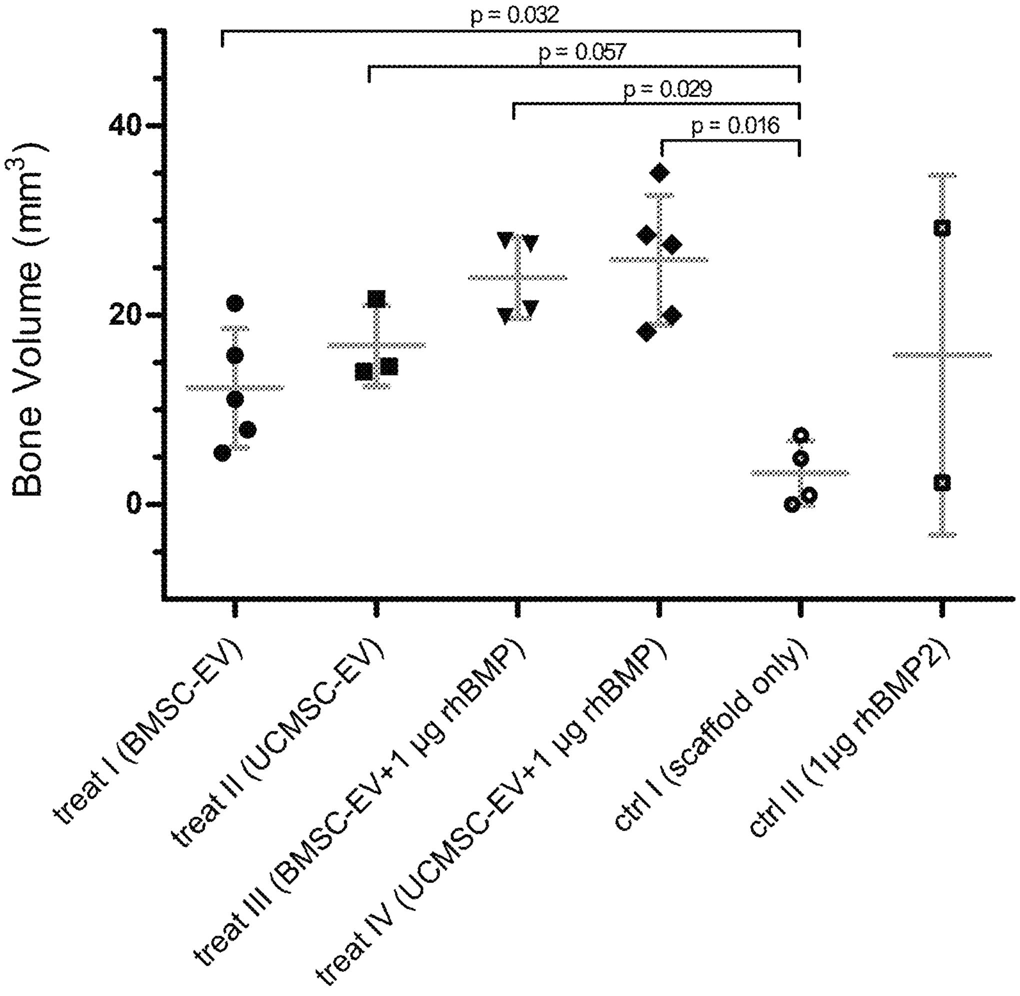

FIG. 4: Comparison of BV between the control and treatment groups that had formed 6 weeks after surgery (p values determined by Mann-Whitney U test are indicated).

Figure 5:
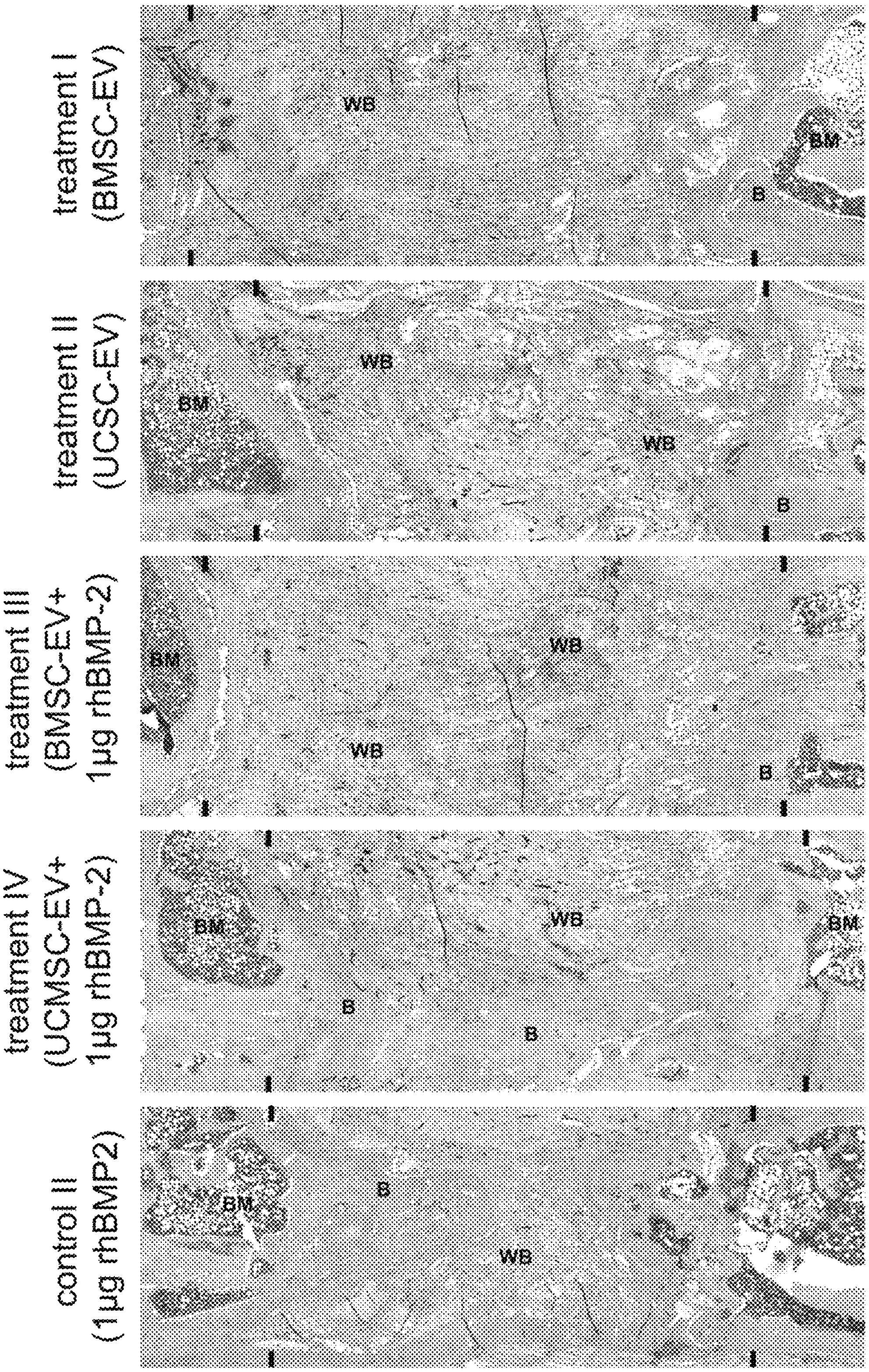

FIG. 5: Histology of representative specimens from each treatment group. Masson's Goldner trichrome stained sections of decalcified femurs for each treatment group and control group II harvested 6 weeks post-surgery.

Black bars indicate site of osteotomy; WB . . . immature, woven bone; B . . . compact bone; BM . . . bone marrow.

Figure 6:
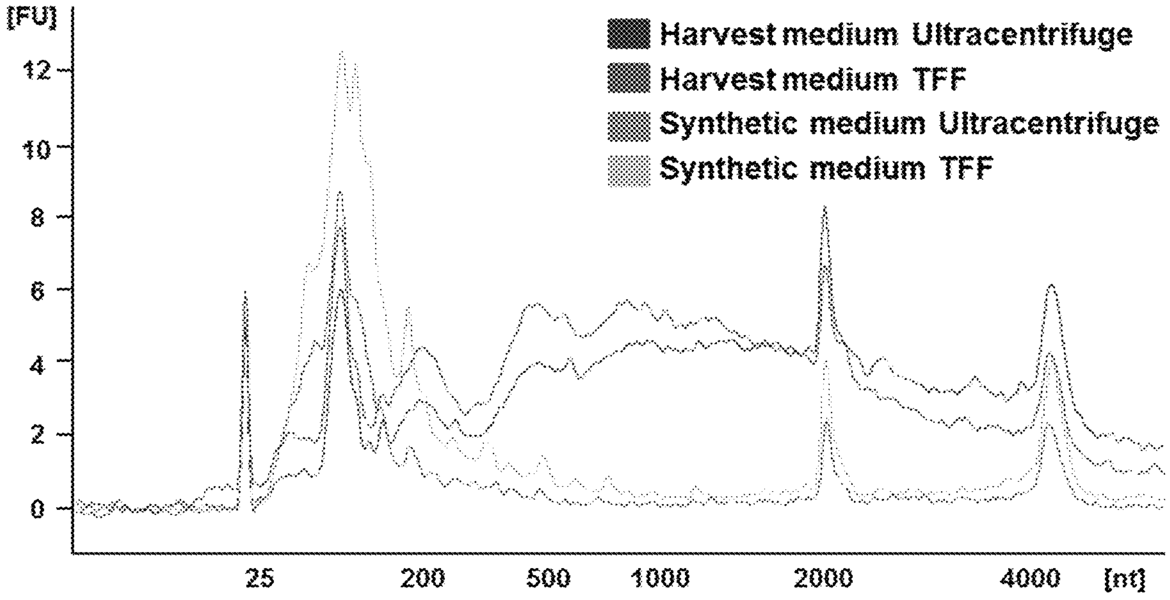

FIG. 6: RNA profiling. EV were isolated from EV-depleted medium B and enriched either by ultracentrifugation or tangential flow filtration (TFF). RNA profiles were obtained through Agilent Bioanalyzer; the x-axes represent RNA size in nt, y-axes the arbitrary fluorescence intensity.

Figure 7:
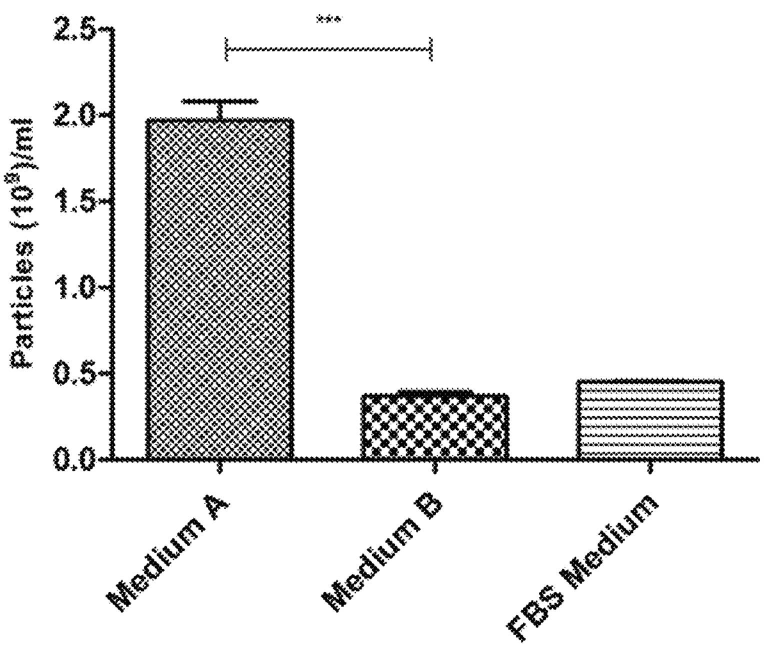
Figure 7:
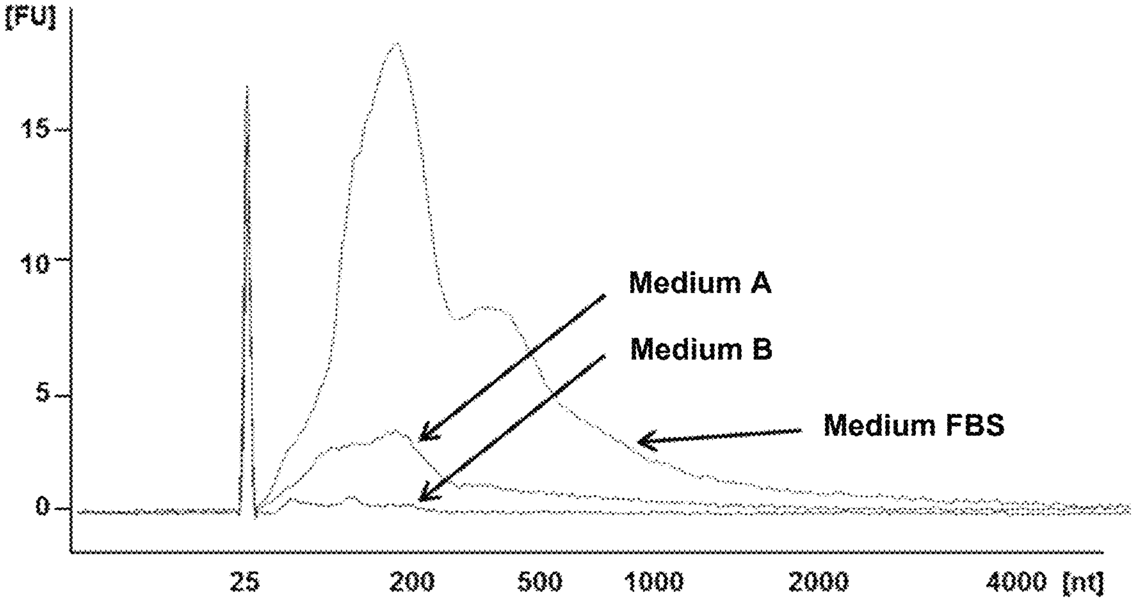

FIG. 7. A single 180 minute centrifugation eliminates RNA-containing pHPL-derived EV. EV were isolated from standard medium A (containing 10% pHPL), EV-depleted medium B (10% pHPL, supernatant after 3 hours at 120,000×g), and medium supplemented with 10% FBS by centrifugation at 120,000×g for 3 hours (n=3). (a) Amount of obtained serum-/pHPL particles per mL medium was determined by NTA: Medium B contains 18.8±2.5% of particles detected in medium A; ***=p<0.001. (b) For RNA profiling, EV were isolated from 120 mL per medium condition as described, RNA was prepared from EV pellets and analyzed with Agilent RNA 6000 Pico technique; the x-axis represents RNA size in nt, y-axis the arbitrary fluorescence intensity: FBS-derived particles contain far more total RNA than pHPL-derived particles. In medium B, the RNA concentration of particles is below the detection limit.

Figure 8A:
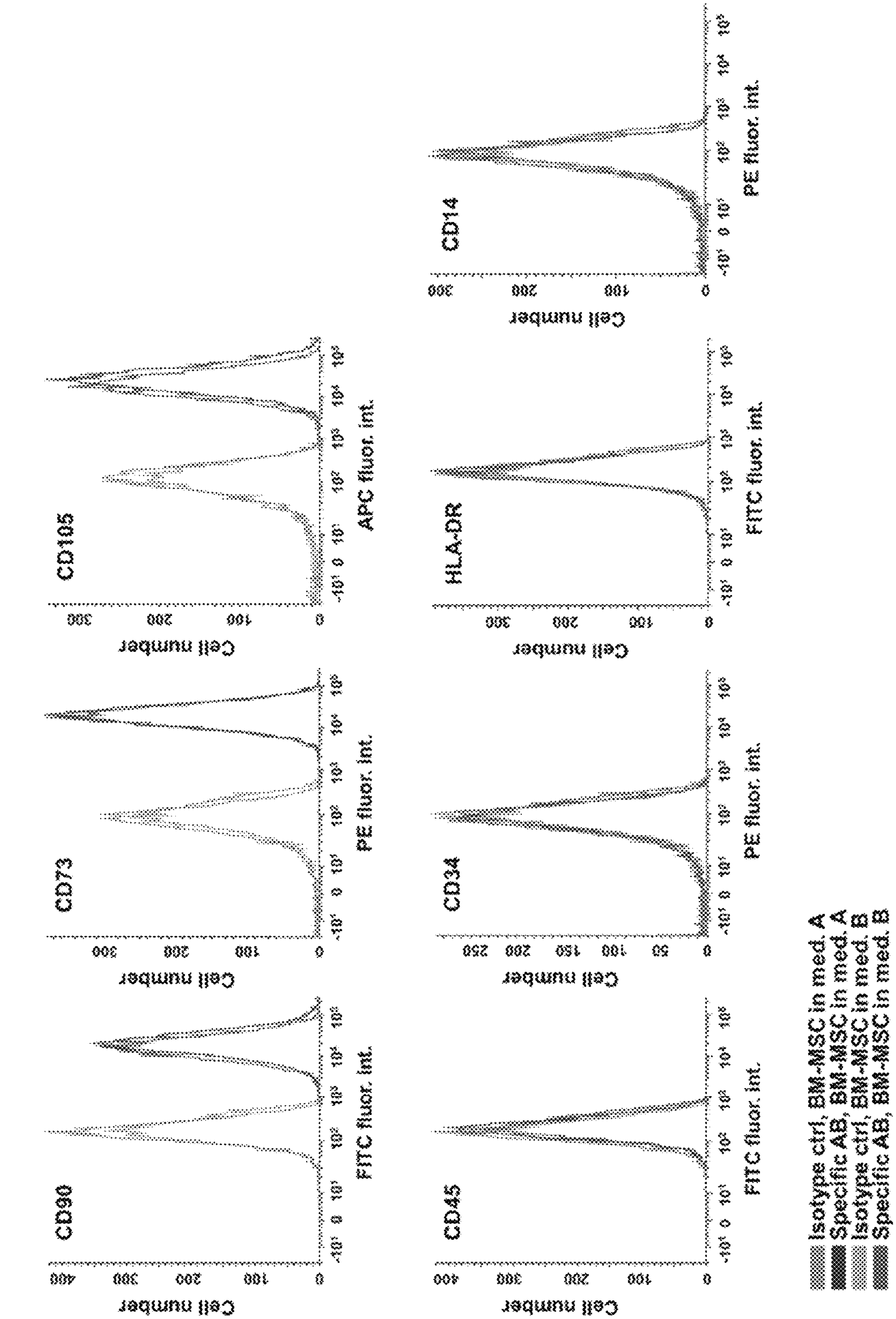
Figure 8:
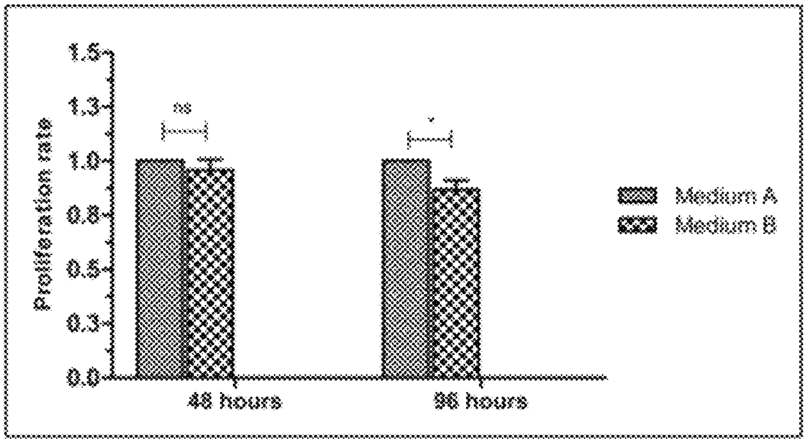
Figure 8:
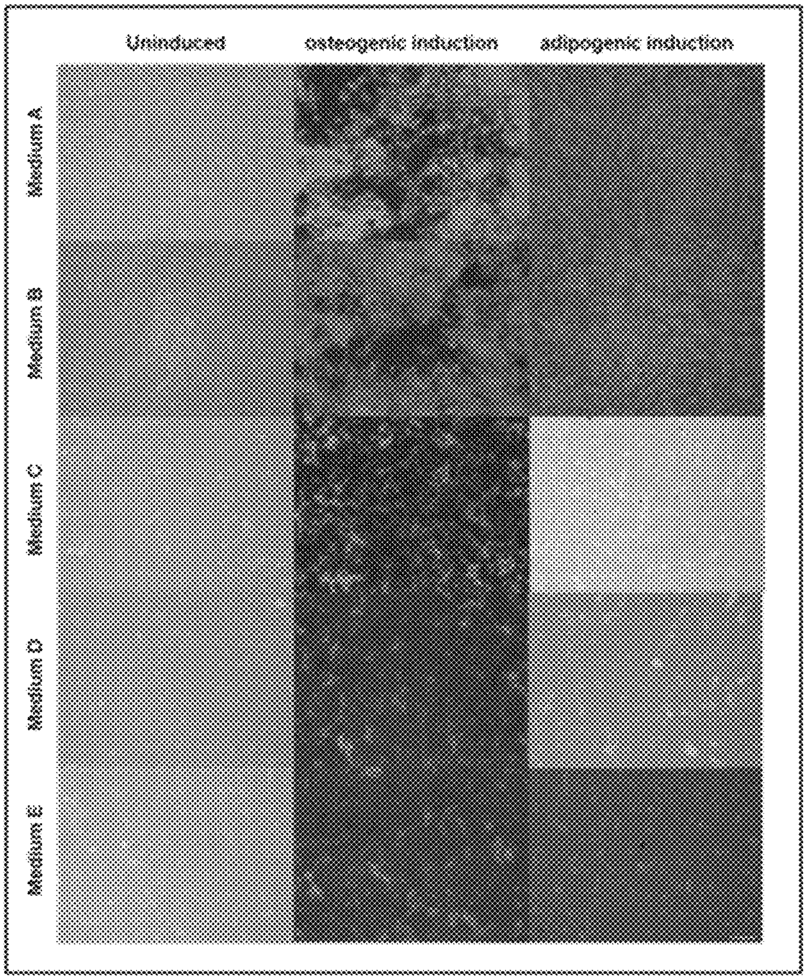

FIG. 8. BM-MSC cultured in EV-depleted medium display the characteristic MSC immunophenotype (a), show slightly reduced proliferation (b) but strong differentiation capacity (c). (a) Flow cytometric analyses shows no difference in surface marker expression of BM-MSC when cultured in medium A (10% pHPL) or medium B (10% pHPL/EV-depleted) over two passages (n=2). (b) Proliferation of cells cultivated in medium A or B over a period of 96 hours analyzed by xCELLigence impedance measurement: Proliferation of BM-MSC is not significantly (ns) decreased after 48 hours but is decreased by 13% after 96 hours (*=p<0.05) in medium B compared to medium A (three individual experiments with 4 wells/condition). (c) The in vitro cell differentiation potential of BM-MSC in different media (medium A, medium B, medium C=serum-/pHPL-free, medium D=2% pHPL, medium E=2% pHPL/EV-depleted) was determined by incubation with differentiation media for 14 days (three individual experiments with 3 wells/condition); osteogenic differentiation was visualized by Alizarin Red S staining, adipogenic differentiation by Sudan III staining: In medium B as basal differentiation medium, osteogenic and adipogenic differentiation are comparable to medium A. pHPL-reduced or serum-/pHPL-free media lead to enhanced osteogenic differentiation and reduced adipogenic differentiation (media C to E). Scale bar: 200 μm.

FIG. 9. Characterization of number and identity of EV from BM-MSC-conditioned media. BM-MSC were cultivated in either medium A (10% pHPL), or medium B (10% pHPL/EV-depleted), and EV were isolated from conditioned media (CM), n=3. EV pellets were resuspended in PBS and measured with NTA technology (a, b). In (a), the number of particles per cell is given; in (b), the number of particles per mL of CM A or B is compared with the number of particles per mL of starting medium A or B: CM B contained 30% of particles detected in CM A (per cell and per mL) and about twice the amount of particles present in starting medium B (***=p<0.001). In CM A, the amount of particles detected is not significantly (ns) elevated compared to particles from the starting medium A. (c, d) For RNA profiling, EV were purified from 60 mL of starting medium or CM, RNA was extracted and analyzed with Agilent RNA 6000 Pico (c) and Agilent Small RNA (d) technique; the x-axis represents RNA size in nt, y-axis the arbitrary fluorescence intensity. Vesicular RNA from CM A and CM B have equal size; EV from media A and B contain little amounts of RNA (c). For Western Blot detection of EV marker proteins CD9, CD81, and TSG101, as well as of Golgi marker GM130, 100 μg of EV protein lysates or total cell lysates (as control) were loaded per well for all samples. In all EV preparations, EV markers were detected while Golgi marker was undetectable.

Figure 10:
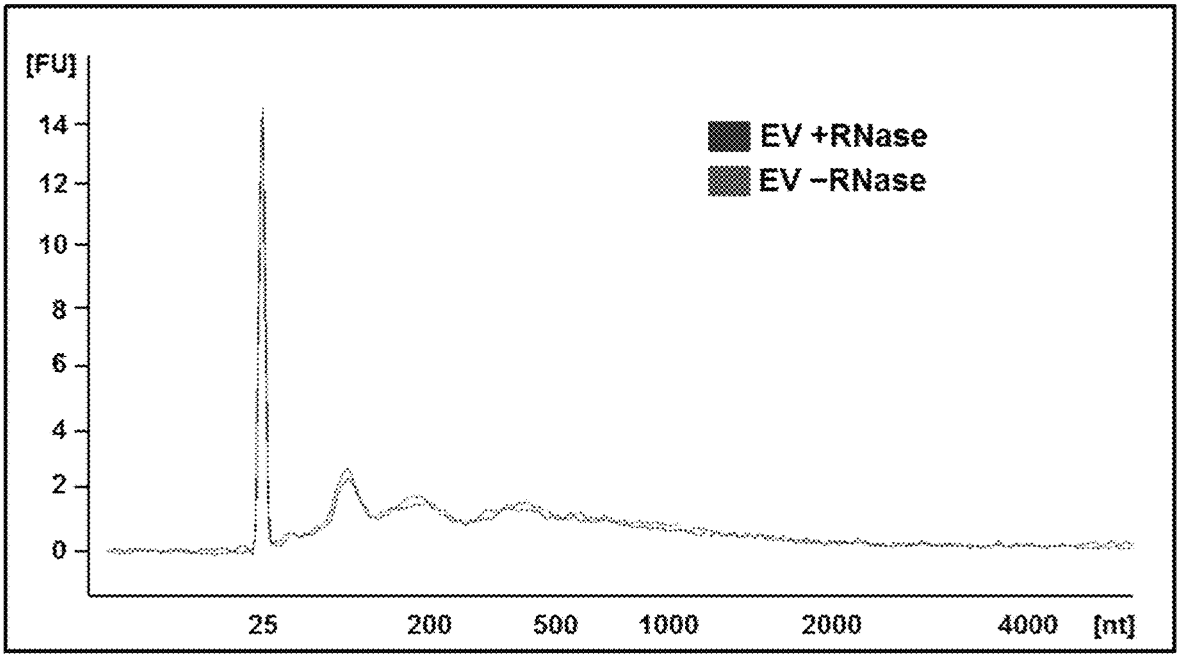
Figure 10:
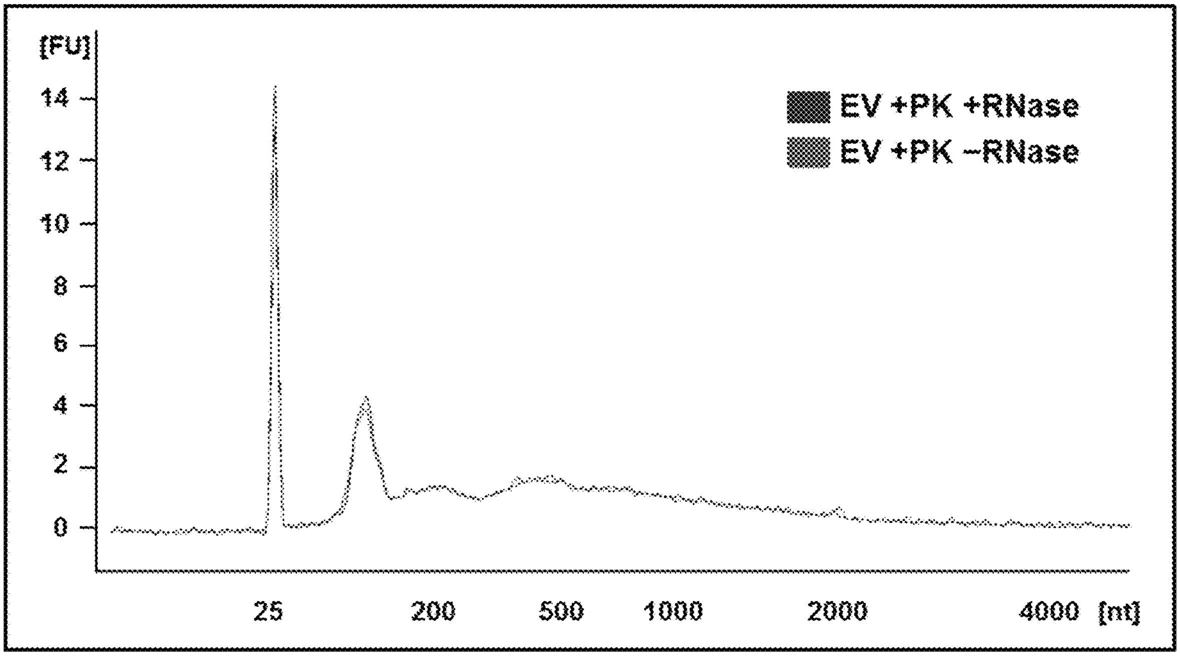
Figure 10:
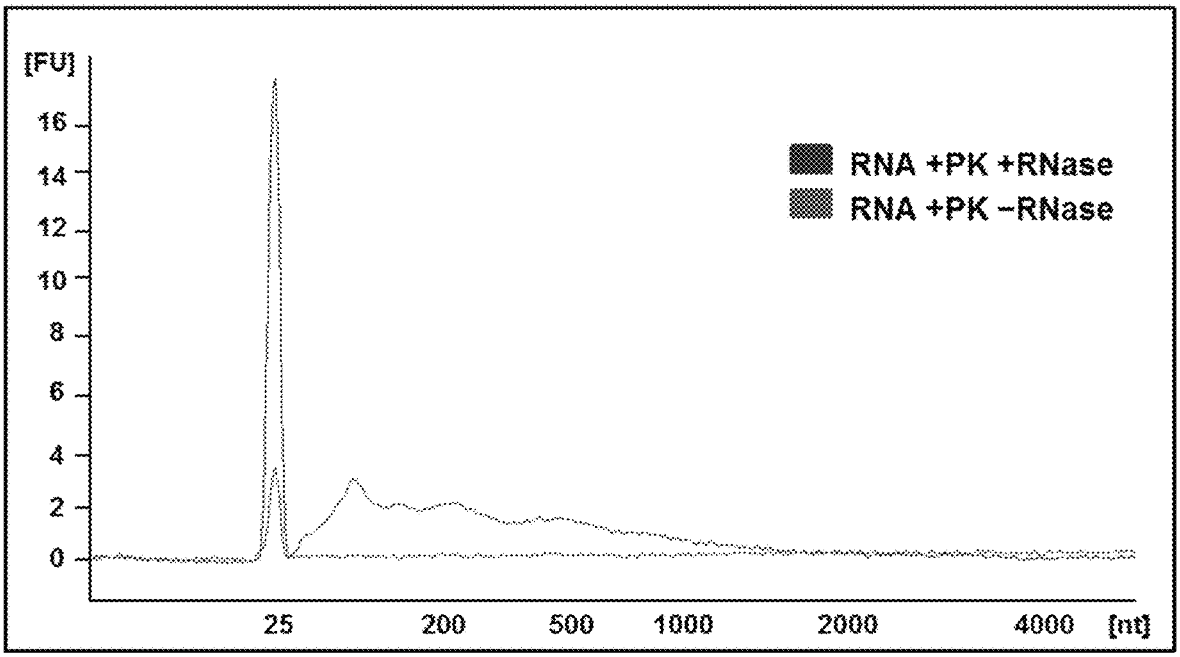

FIG. 10. Isolated RNA is derived from EV. EV pellets from BM-MSC-conditioned medium A (n=2) were incubated with RNase A (a) or with proteinase K followed by RNase A treatment prior to RNA extraction (b). To verify that proteinase K activity is inhibited by incubation at 90° C. for 5 minutes, and to control RNase A activity, RNA isolated from BM-MSC-derived EV was treated with proteinase K and RNase A (c). RNA profiles were obtained through Agilent Bioanalyzer; the x-axes represent RNA size in nt, y-axes the arbitrary fluorescence intensity.

Figure 11:
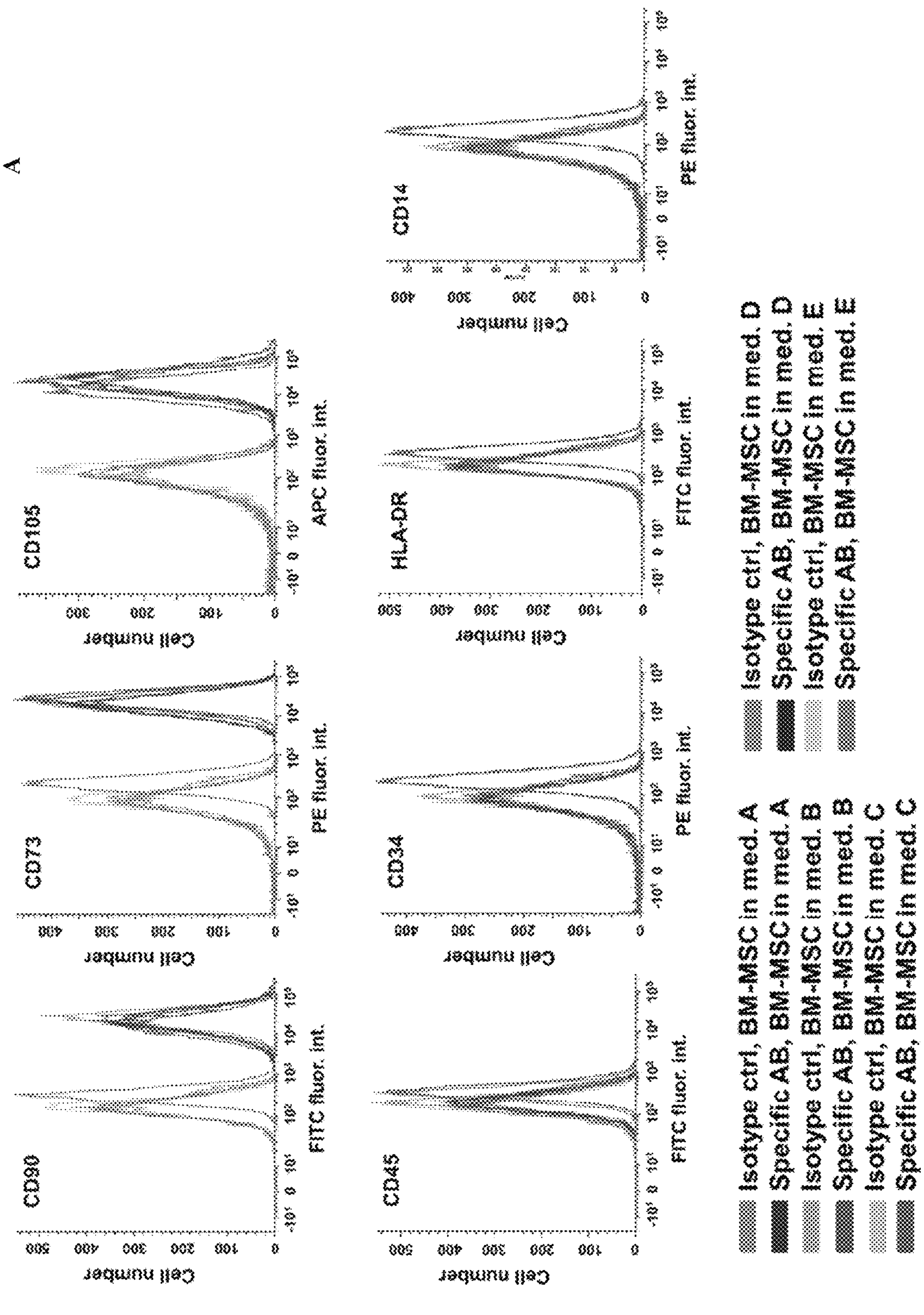
Figure 11:
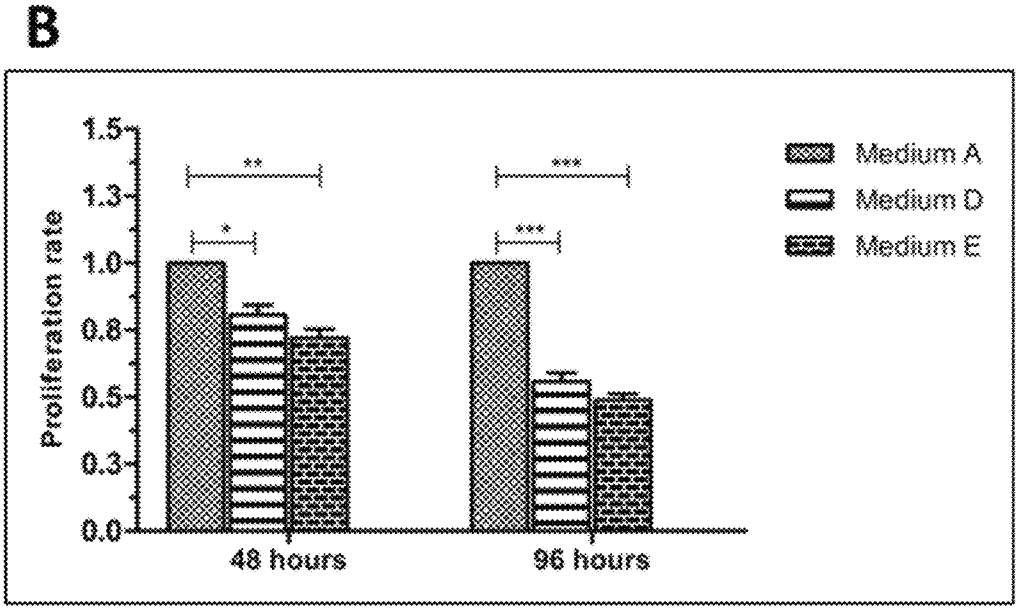

FIG. 11. pHPL-reduced or serum-/pHPL-free culture conditions have no effect on MSC immunophenotype (a) but decrease proliferation (b). (a) Surface marker expression was analyzed by flow cytometry of BM-MSC after five days in medium C (pHPL-free), or after two passages in medium D (2% pHPL) and medium E (2% pHPL/EV-depleted), and compared to marker expression after cultivation in medium A (10% pHPL) and B (10% pHPL/EV-depleted), n=2. (b) Cell proliferation was determined by xCELLigence impedance measurement of cells transferred from medium A to media D or E over a period of 96 hours (three individual experiments with 4 wells/condition). After 48 hours, proliferation in media D and E is decreased by 19% and 28%, after 96 hours by 44% and 51%, respectively, compared to the capacity determined in medium A (*=p<0.05; =p<0.01; *=p<0.001).

Figure 12:
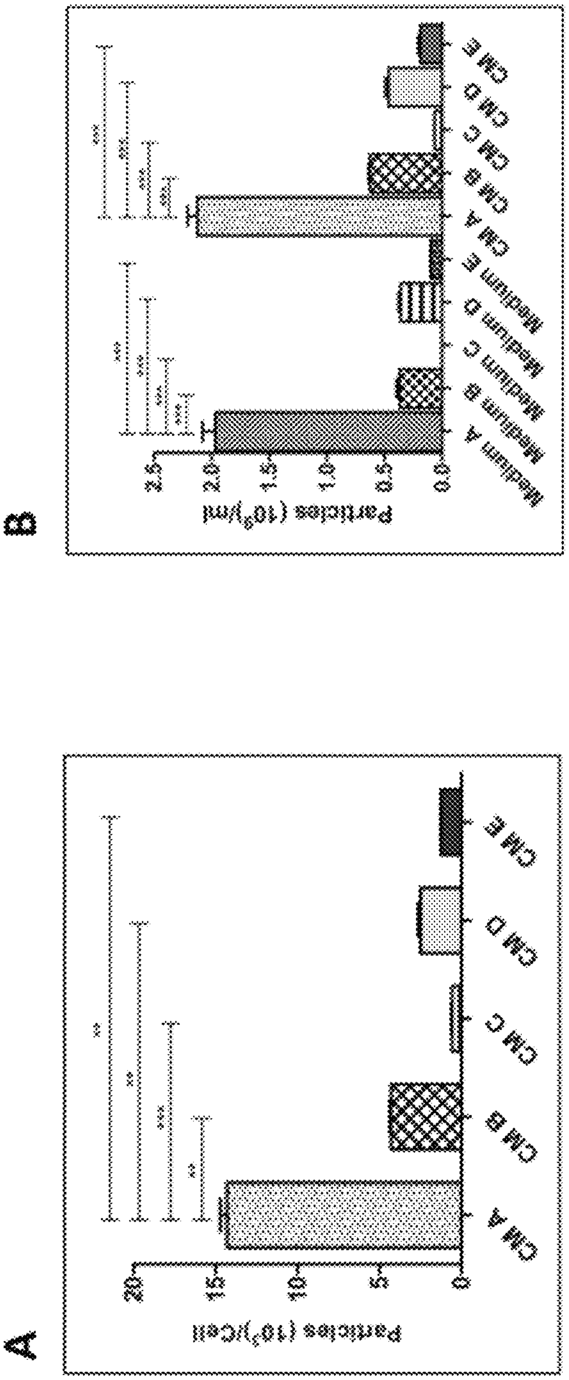
Figure 12:
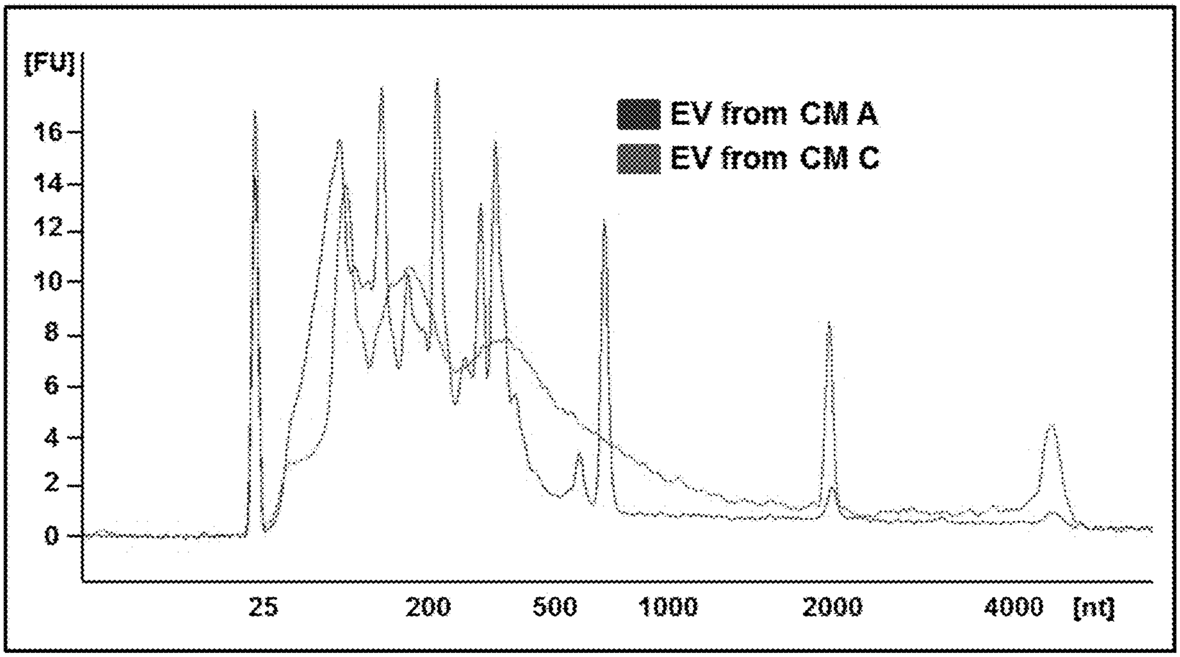
Figure 12:
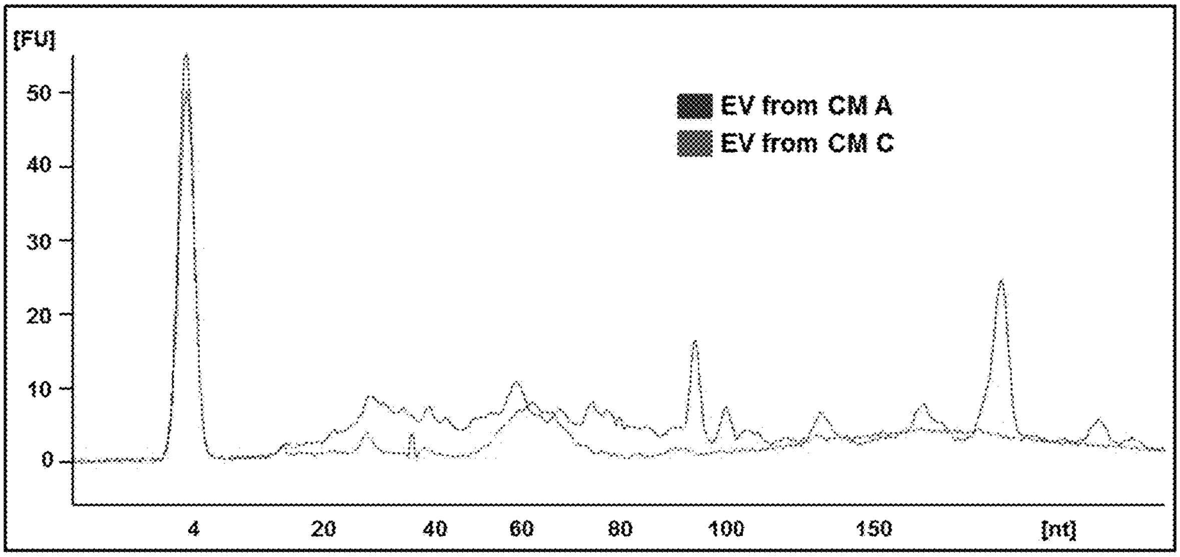
Figure 12:
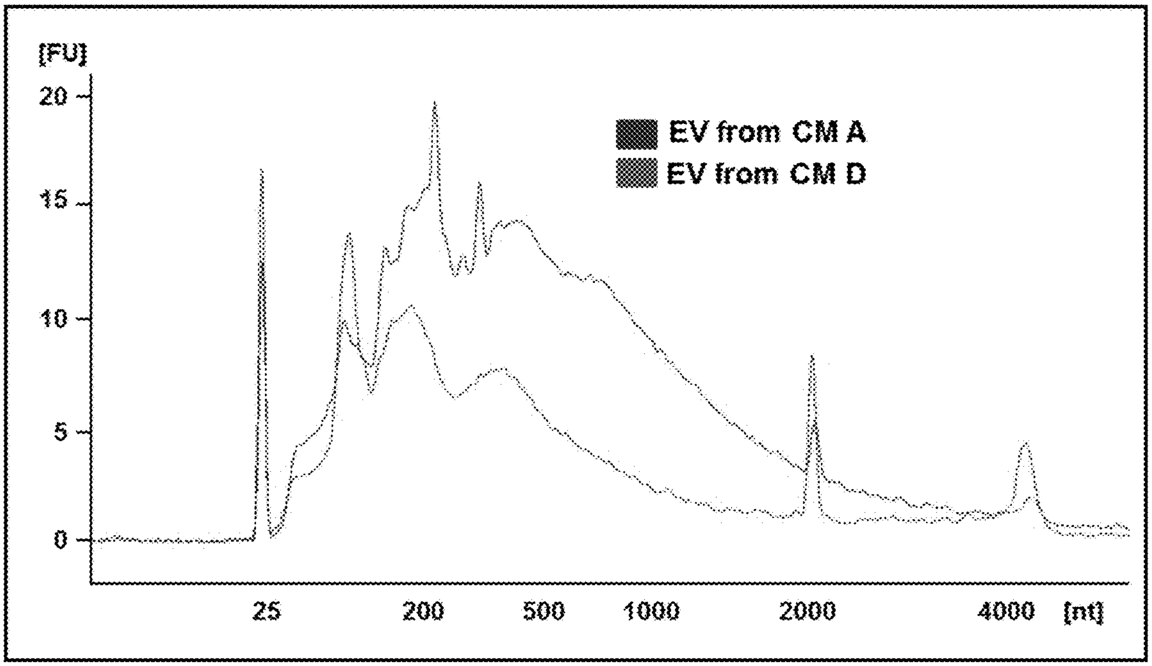
Figure 12:
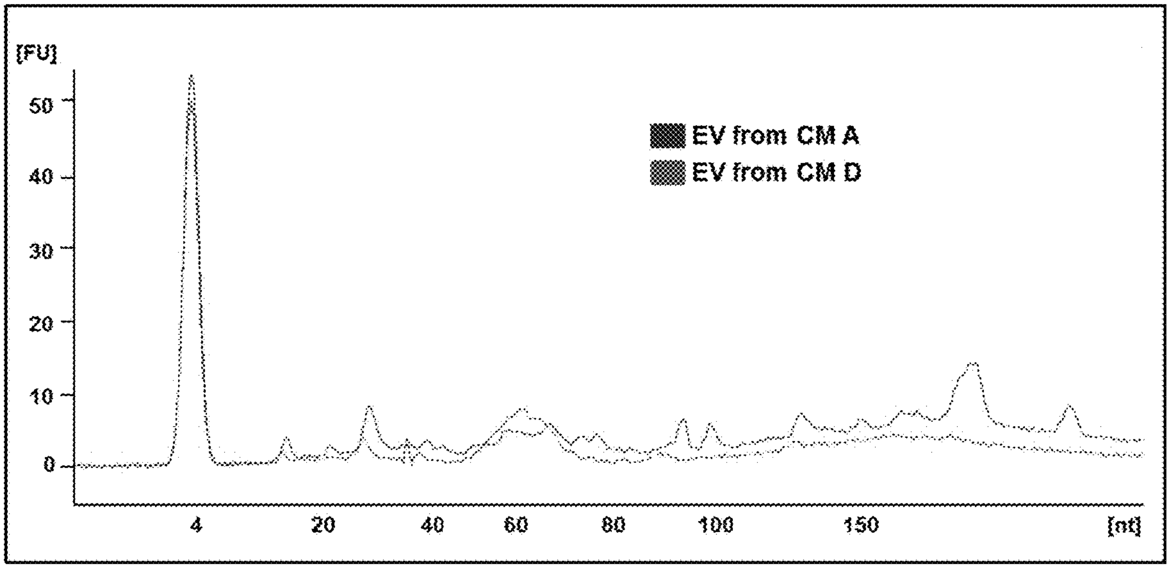
Figure 12:
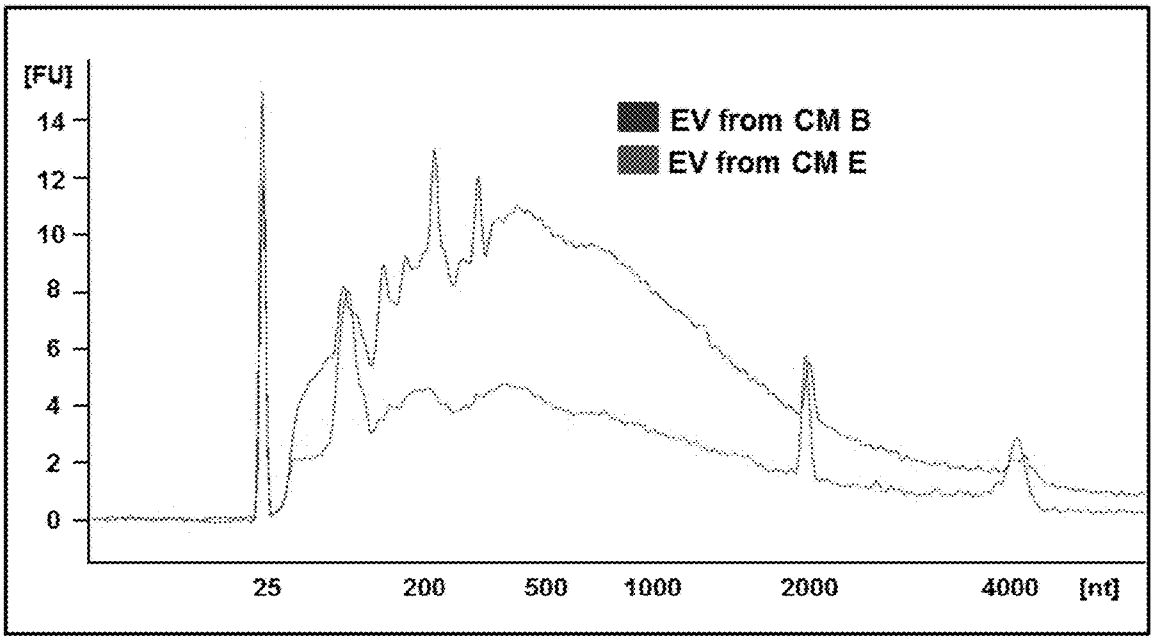
Figure 12:
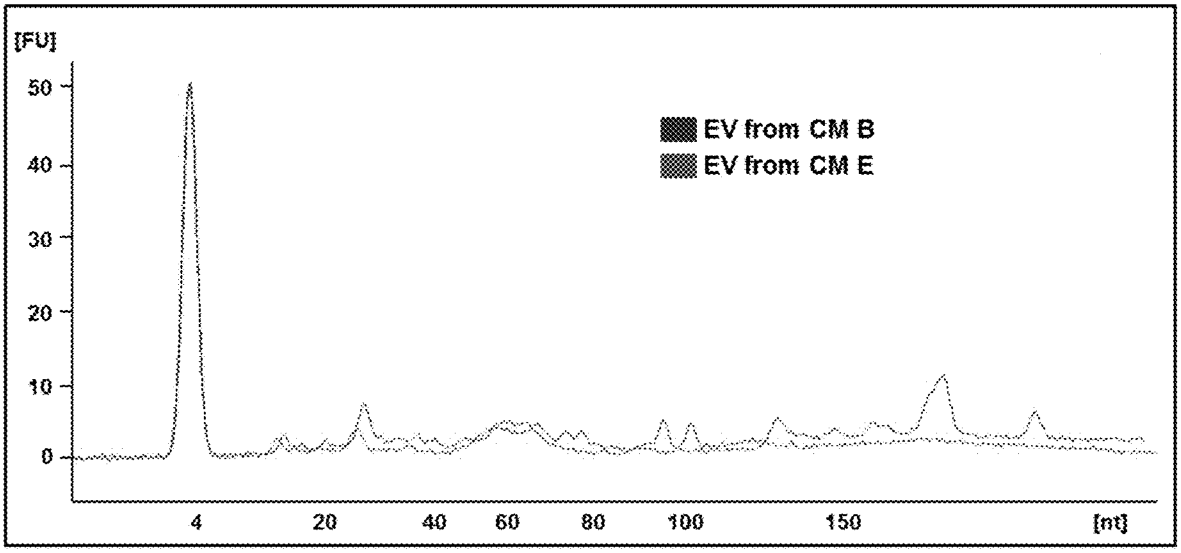
Figure 12:
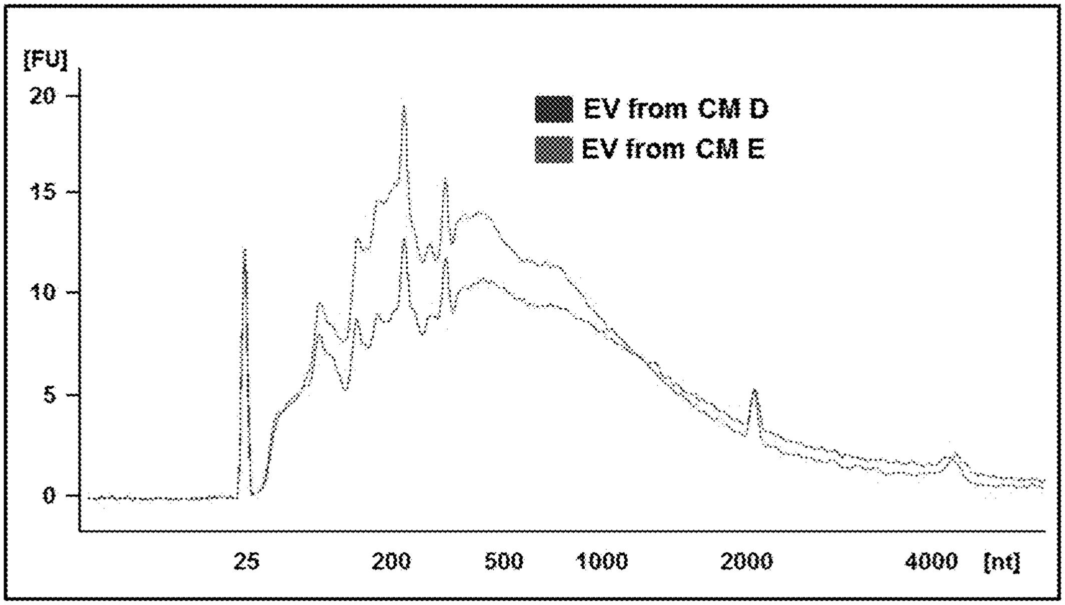
Figure 12:
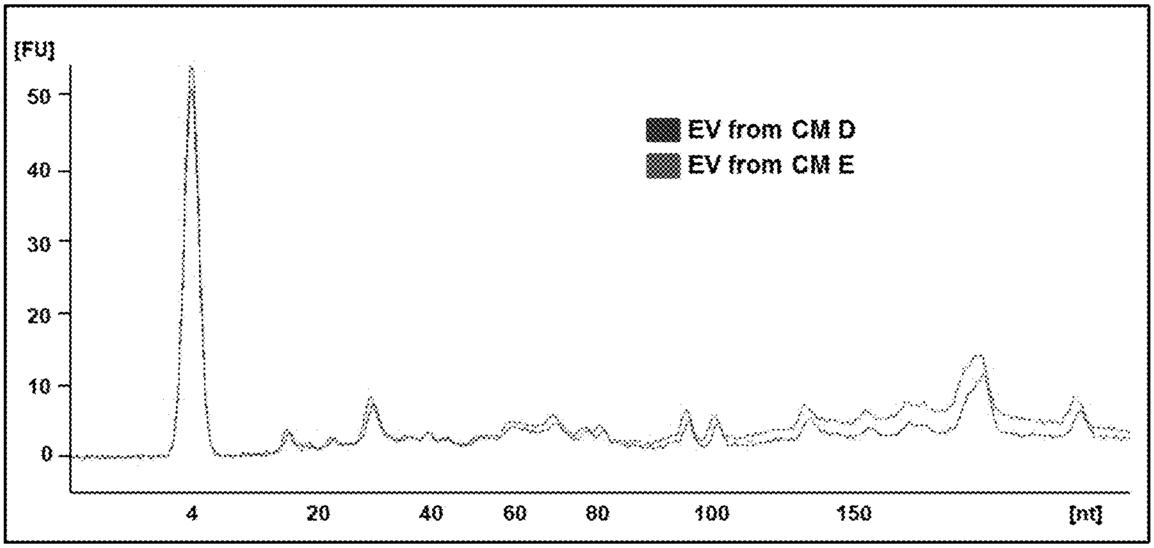

FIG. 12. pHPL-reduced or serum-/pHPL-free culture conditions strongly affect number and RNA content of BM-MSC-derived EV. BM-MSC were cultured in medium A (10% pHPL), B (10% pHPL/EV-depleted), C (pHPL-free), D (2% pHPL), or E (2% pHPL/EV-depleted), and EV were harvested from conditioned media (CM), n=3. Amounts of nanoparticles per cell (a) as well as per mL of medium or CM (b) were determined by NTA measurement (=p<0.01; *=p<0.001). RNA profiles (c-j) were obtained by harvesting EV from 60 ml of CM per medium type, extraction of EV RNA, and analysis with Agilent RNA 6000 Pico (c, e, g, i) and Agilent RNA Small (d, f, h, j) technique. The x-axes represent RNA size in nt, y-axes the arbitrary fluorescence intensity. pHPL-reduced or serum-/pHPL-free culture conditions lead to increased amounts of larger RNA species detected in EV.

Figure 13:
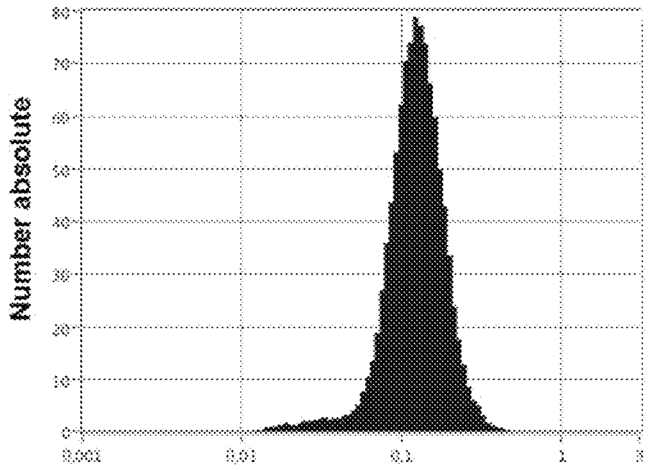
Figure 13:
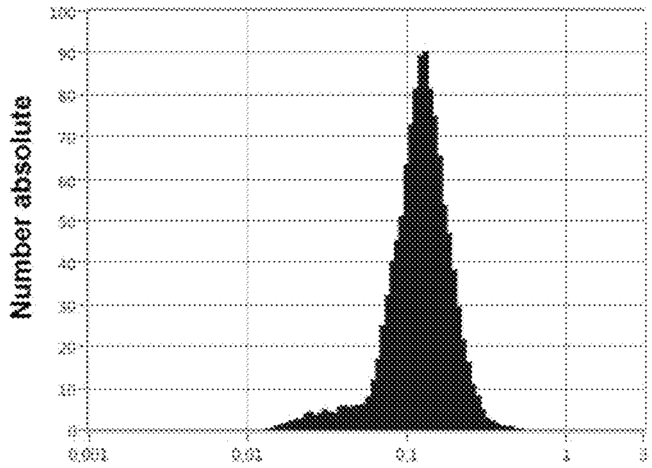
Figure 13:
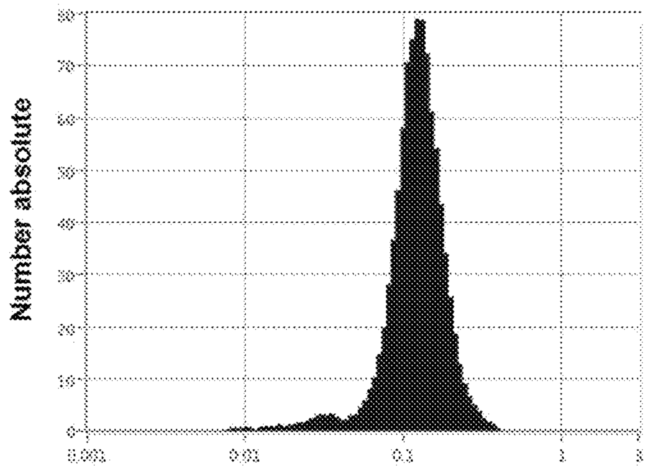

FIG. 13. Size distribution of serum-/pHPL-derived particles. EV were isolated from medium A (10% pHPL), medium B (10% pHPL/EV-depleted), and 10% FBS-containing medium by centrifugation at 120,000×g for 3 hours (n=3). Size of pelleted serum-/pHPL particles was determined by NTA. pHPL-derived EV (media A and B) display a mean diameter of 126 nm, FBS-derived particles of 124 nm. Representative curves are shown.

Figure 14:
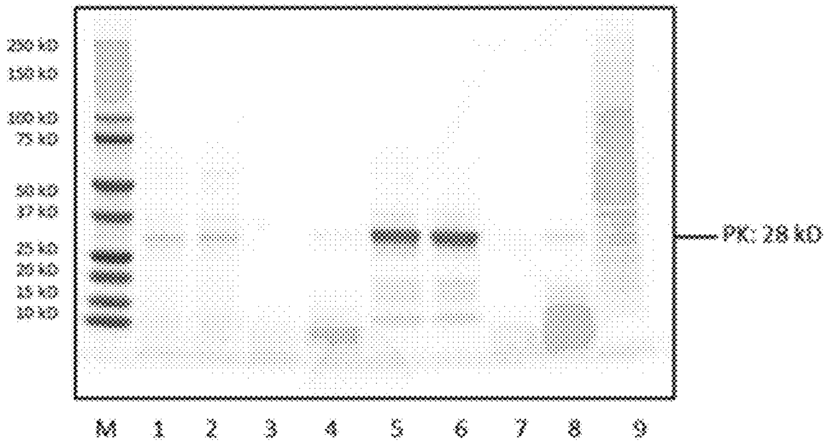

FIG. 14. Optimization of proteinase K treatment for proteinase and RNase protection assay. BM-MSC lysates containing 100 μg of total protein were incubated with two different concentrations of proteinase K (PK) at 37° C. for 30 minutes, followed by incubation at RT for 10 minutes with/without addition of PMSF, and subsequent incubation at 90° C. for 5 minutes, or at 4° C. for 5 minutes, respectively. Proteins and size marker (Precision Plus Protein Dual Color Standard, 161-0374, Bio-Rad) were separated on 4-15% gradient polyacrylamide gels and detected with Acqua Stain (Acqua Science). Based on the results, 0.05 μg/μl PK with subsequent incubation at 90° C. for 5 minutes was determined as optimal for proteinase and RNase protection assay.

Figure 15:
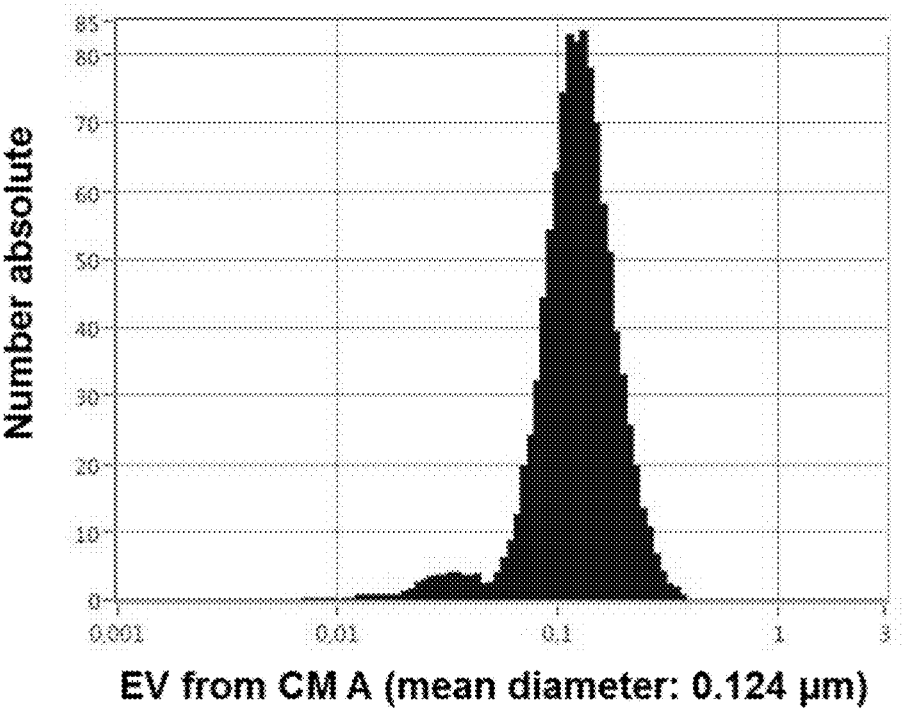
Figure 15:
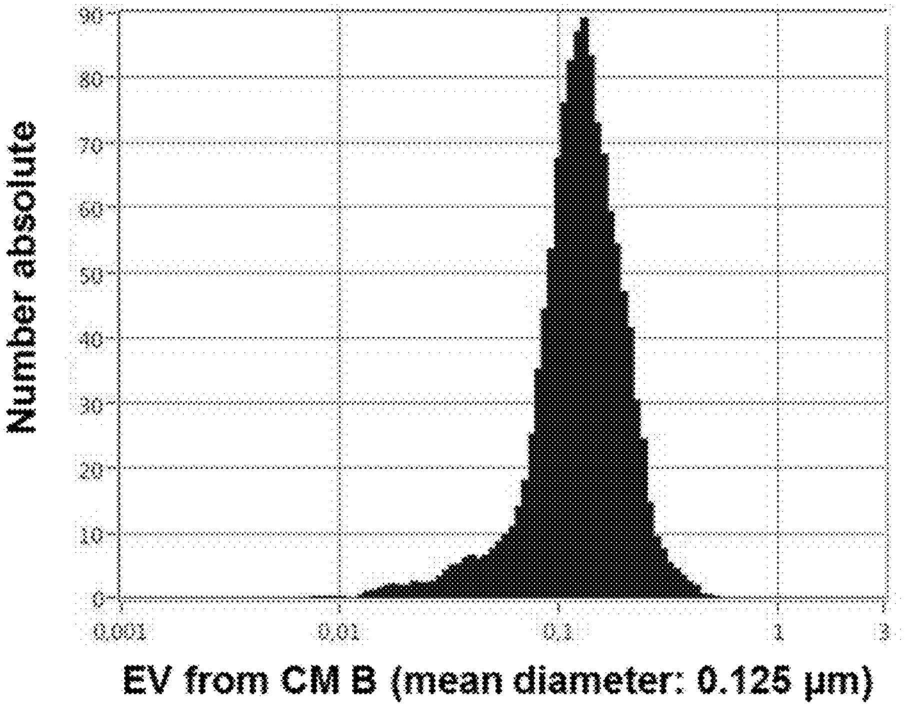

FIG. 15. Size distribution of BM-MSC-derived particles. BM-MSC were cultivated in medium A (10% pHPL) or medium B (10% pHPL/EV-depleted), and EV were isolated from conditioned media (CM) as described in Materials and Methods (n=3). Size of pelleted particles was determined by NTA. Particles from CM A display a mean diameter of 124 nm, particles from CM B of 125 nm. Representative curves are depicted.

Figure 16:
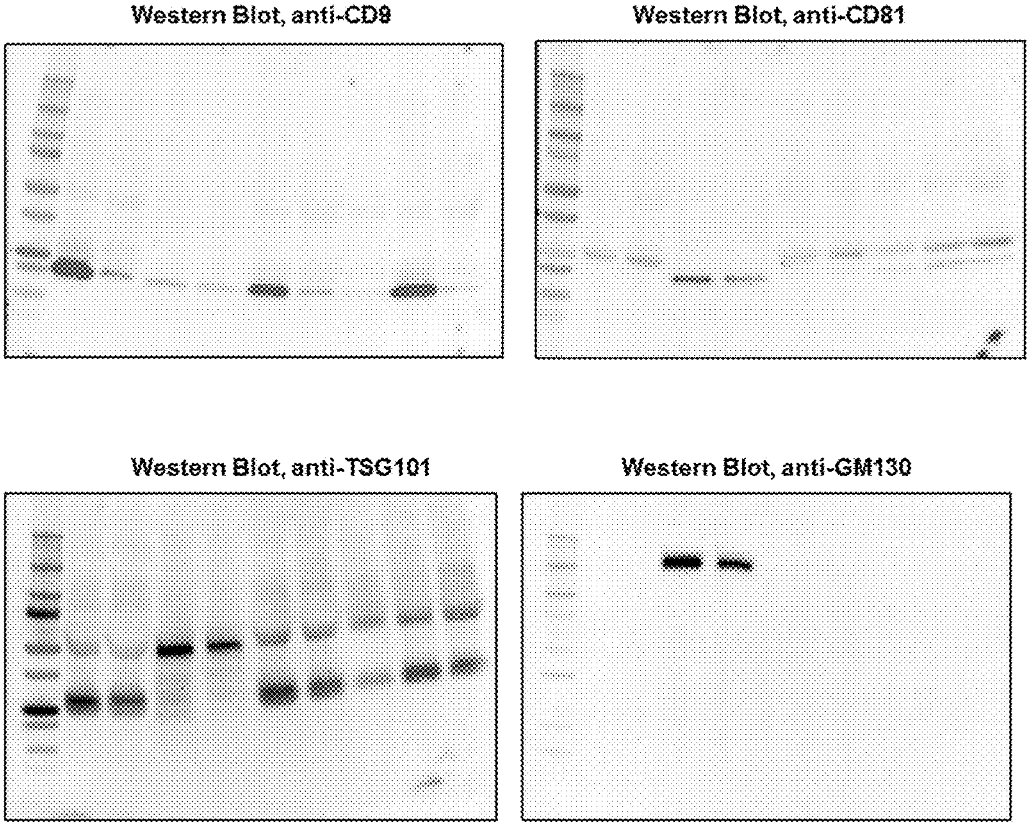

FIG. 16. Unprocessed Western Blot images. Protein size marker: Precision Plus Protein Dual Color Standard (161-0374, Bio-Rad).

Figure 17:
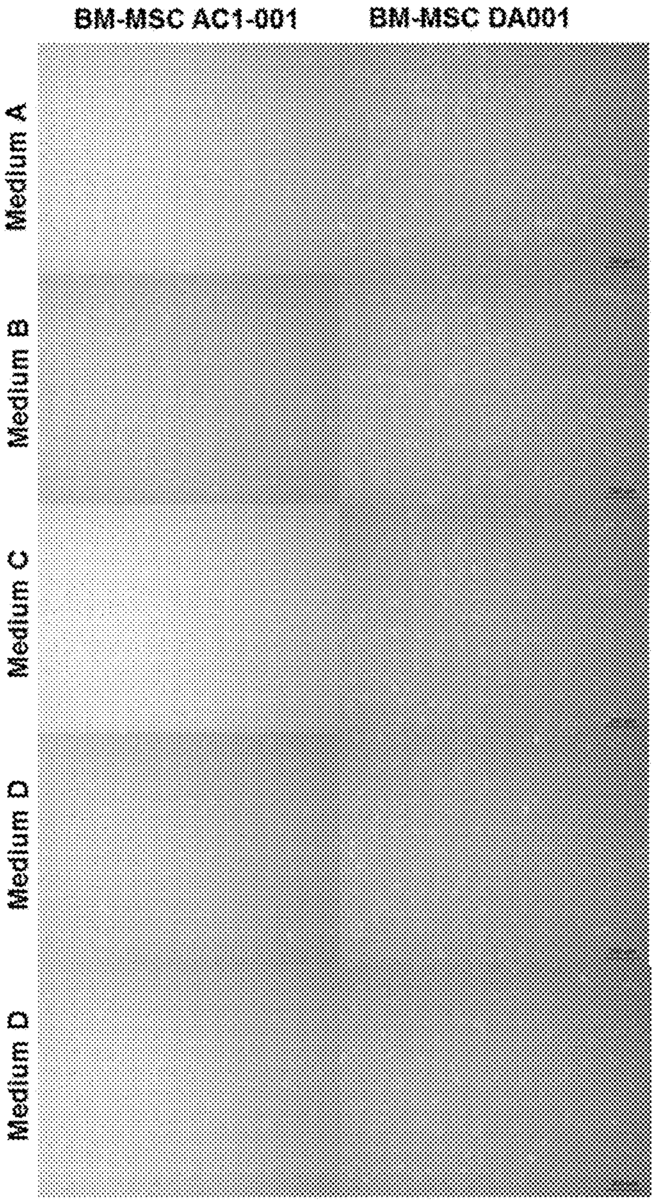

FIG. 17. Images of BM-MSC from two donors cultured in five different media.

Figure 18:
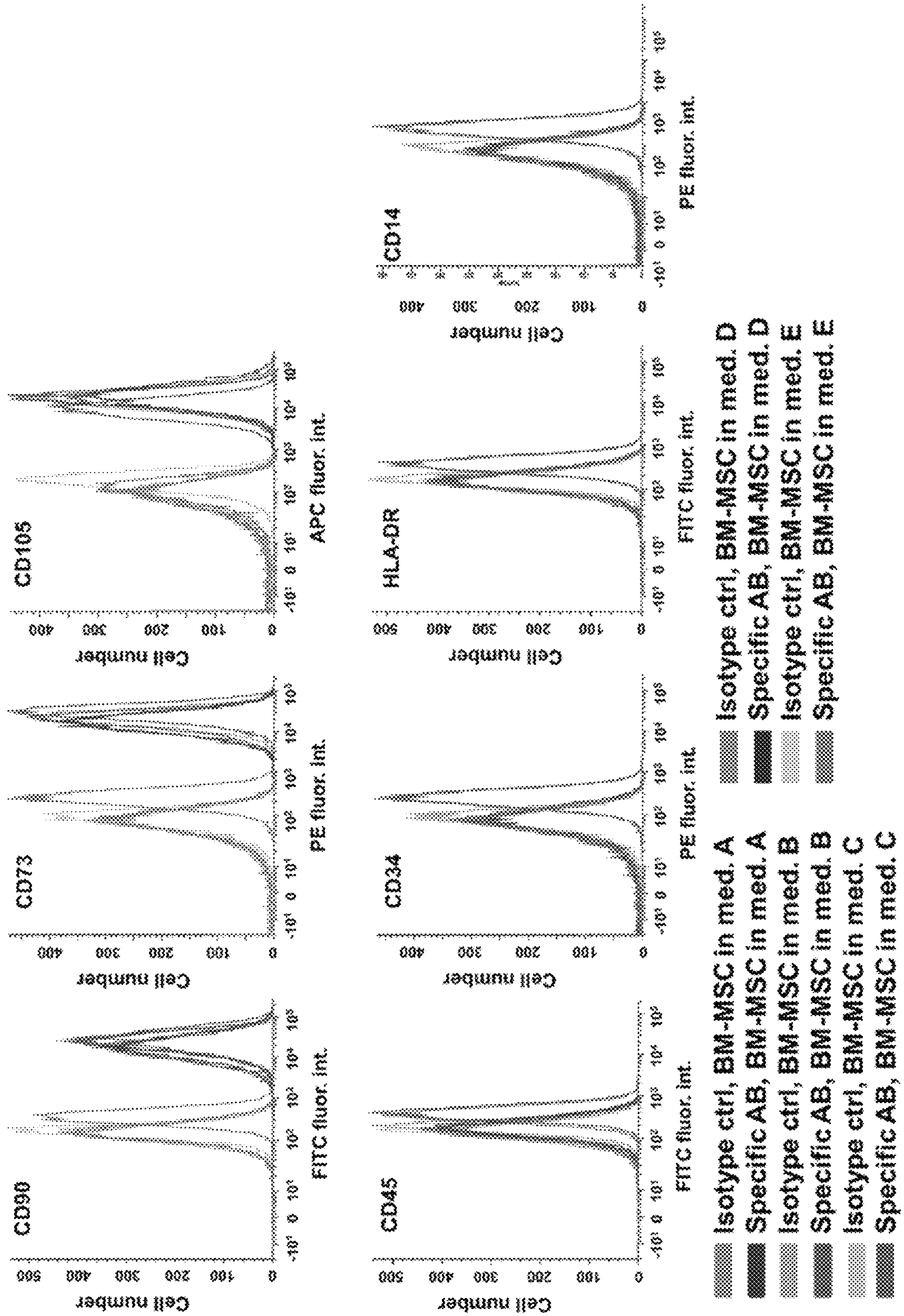

FIG. 18. Expression of MSC surface markers of BM-MSC DA001 cultured in five different media (n=2).

Figure 19:
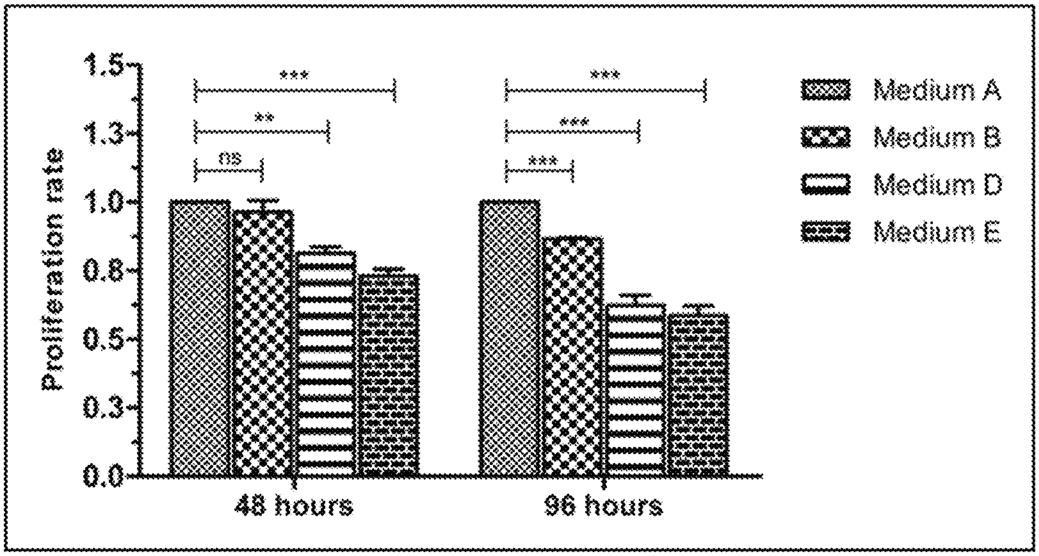

FIG. 19. Cell proliferation analysis of BM-MSC DA001 cultured in four different media (three individual experiments with 4 wells/condition). (ns=not significant; =p<0.01; *=p<0.001)

Figure 20:
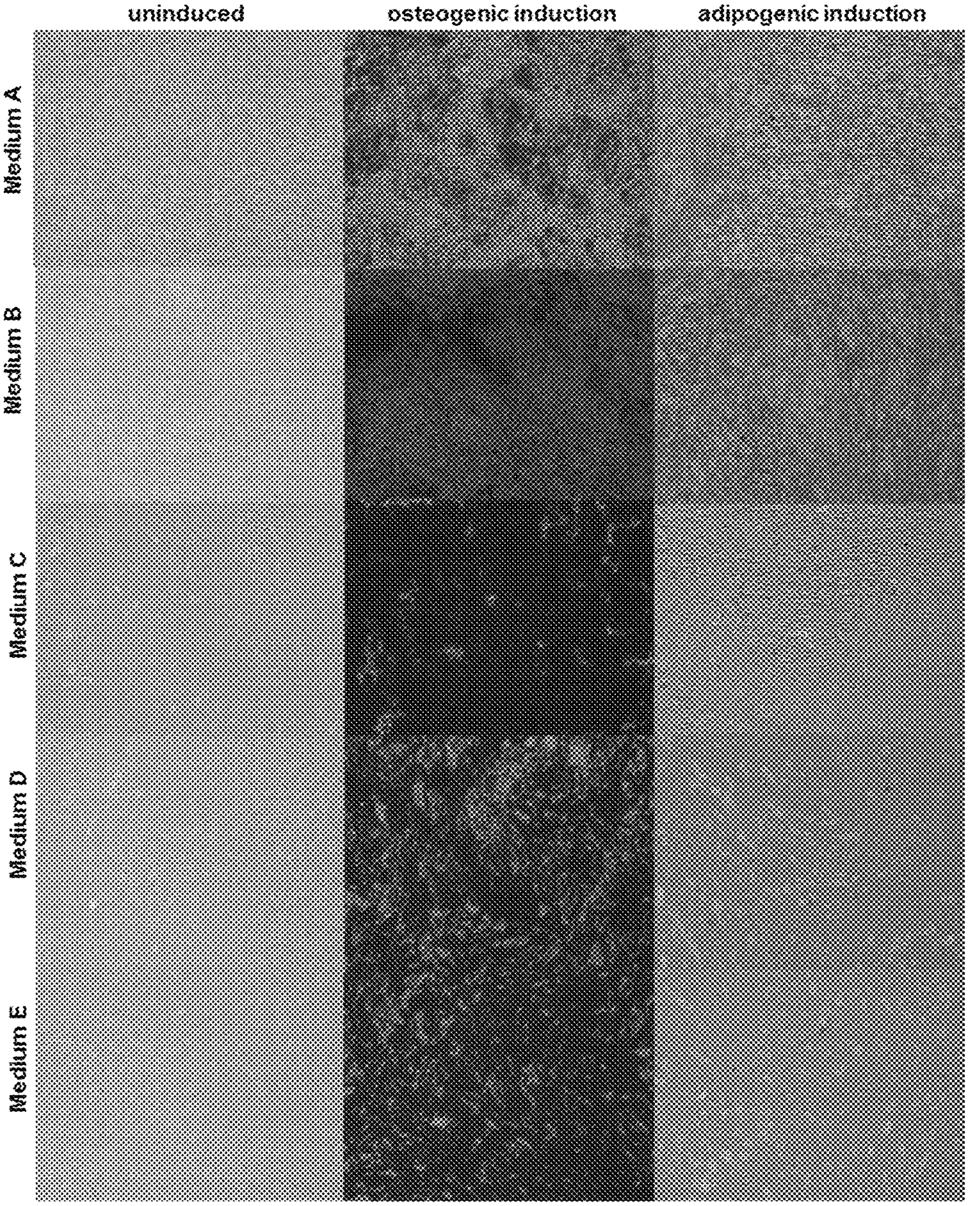

FIG. 20. Cell differentiation analysis of BM-MSC DA001 cultured in five different media (three individual experiments with 3 wells/condition).

FIG. 21. Characterization of number and identity of EV from BM-MSC DA001 cultured in five different media (n=3 EV isolates/condition). In (a) and (b) the NTA-determined number of particles per cell and per mL of CM, respectively, is given (*=p<0.05; **=p<0.01). In (c) EV RNA profiling as analysed with Agilent RNA 6000 Pico technique is depicted. In (d) a Western Blot analysis of EV/cellular proteins can be seen.

The present invention is additionally described by way of the following illustrative non-limiting examples that provide a better understanding of the present invention and of its many advantages.

Figure 22:
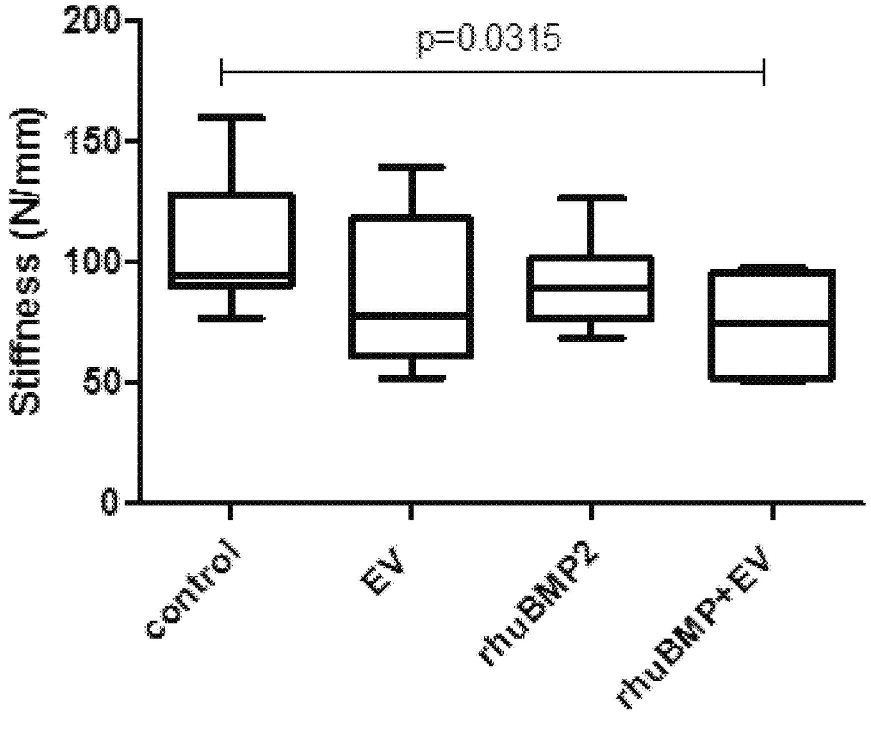

FIG. 22: Boxplot demonstrating stiffness values (N/mm) for the control group and the treatment groups (pairwise comparison; Mann Whitney test) 2 weeks after patellar enthesis surgery in rats.

EXAMPLE 1: MSC-DERIVED EXOSOMES ENHANCE BONE REGENERATION WITH OR WITHOUT LOW DOSE RHBMP2 IN A RAT FEMUR DEFECT MODEL

1. Methods

2.1 Medium Preparation

Heparin-free and fibrinogen-depleted medium was prepared as follows: Alpha-modified Minimal Essential Medium Eagle (alpha-MEM, M4526, Sigma-Aldrich) was supplemented with 5 mM (N2)-L-Alanyl-L-Glutamine (Dipeptiven, 11051014, Fresenius Kabi, Austria) and 10% pHPL. pHPL was produced as described earlier (Schallmoser, 2007). The mixture was immediately divided into 14 aliquots (40 mL in 50 mL centrifuge tubes), maintained for 4-6 h at 20-24° C. until biogel formation was completed, and stored at 4° C. for 12-18 h. To remove fibrin, the clotted medium was brought to 37° C. The fibrin gel was then physically collapsed by exceeding the shear forces to the matrix, and the precipitated fibrin was pelleted at 2,500×g at 20° C. for 12 minutes (Laner-Plamberger, 2015). Finally, the supernatant was filtered (0.22 μm). Heparin-free, fibrinogen-depleted and EV-depleted medium was produced from the above by a single centrifugation step at 120,000×g for 3 h (employing a Sorvall MX-120 or WX-80 ultracentrifuge, fixed angle rotor, Thermo Scientific). The resulting supernatant was filtered through a 0.22 μm filter, to yield EV-depleted medium. HPL-free medium was generated by adding 5 mM Dipeptiven to alpha-MEM, followed by filtration (0.22 μm).

2.2 Cell Culture

Cells were cultured at 37° C. and 5% $CO_2$. Experiments were performed with two different primary human BM-MSC and UC-MSC preparations, respectively. One BM aspirate was directly obtained from the University Clinic for Blood Group Serology and Transfusion Medicine, Paracelsus Medical University, Salzburg (Austria). The second BM aspirate was purchased from AllCells (California, USA). Both donors had signed an informed consent. BM-MSC were isolated from bone marrow as described and were tested negative for mycoplasma. For all experiments, cells were kept in 30 mL medium per T225 flask.

2.3 Isolation of pHPL- and MSC-Derived Extracellular Vesicles

EVs released by MSCs may contribute to biological processes like tissue regeneration, immunomodulation, and neuroprotection. Evaluation of the therapeutic potential of MSC-derived EV and their application in future clinical trials demand thorough characterisation of their content as well as production under defined medium conditions, devoid of both xenogenic substances and serum-derived vesicles. We have addressed the apparent need for such a growth medium and have developed a medium formulation based on pooled human platelet lysate (pHPL) that is free from animal-derived xenogenic additives and depleted from EVs, for the generation of exclusively MSC-derived EV. Depletion of EVs from complete growth medium was achieved by centrifugation at 120,000×g for three hours, which eliminated 94.4% (±1.4%) of RNA-containing pHPL EVs. MSCs propagated in this medium retain the characteristic surface marker expression, cell morphology, viability, and in vitro osteogenic and adipogenic differentiation potential. The proliferation rates are decreased by 4% after 48 hours and 13% after 96 hours. EVs collected from MSCs cultured in the EV-depleted medium reveal a similar RNA pattern compared to EVs generated in standard pHPL EV-containing medium, but displayed a more clearly defined pattern of proteins characteristic for EVs. Specifically, the EV marker CD9 is present in large amounts in EVs collected from unconditioned medium (see FIG. 21D). EVs enriched from conditioned medium that has not been clarified and depleted of serum/platelet-derived EVs are contaminated with these platelet-derived EVs and cause substantial miscalculations of the amount of purified MSC EVs. In particular, extracellular vesicles obtained by a cultivation in a culture medium (medium A) that is free of fibrin and heparin and that comprises vesicles derived from pHPL showed an increased level of CD9 in comparison to the extracellular vesicles obtained by a cultivation in a culture medium (medium B) that is free of fibrin and heparin and that is additionally depleted of vesicles comprised in pHPL (see FIG. 21 D). Further, the extracellular vesicles obtained by a cultivation in a culture medium (medium B) that is free of fibrin and heparin and that is additionally depleted of vesicles comprised in pHPL showed an increased level of CD9 in comparison to extracellular vesicles that are cultured in a culture medium (medium C) that does not comprise serum or lysate, such as FBS or pHPL (FIG. 9 E). Thus pHPL-based and EV-depleted medium, free from animal-derived xenogenic additives like heparin, is appropriate for the enrichment and purification of exclusively human MSC-derived EVs. With this GMP-grade protocol, characterisation and establishment of protein and RNA profiles from MSC-derived EV can now be achieved to identify active components in therapeutic EV for clinical application. Moreover, this protocol allows the definition of the MSC-derived active compounds as no other source of vesicle contamination other than the cultured and immunophenotyped MSCs contribute to the conditioned media.

Heparin-Free and Fibrinogen-Depleted Medium is Prepared as Follows:

Alpha-modified Minimal Essential Medium Eagle (alpha-MEM, M4526, Sigma-Aldrich) supplemented with 5 mM (N2)-L-Alanyl-L-Glutamine (Dipeptiven, 11051014, Fresenius Kabi, Austria) and 10% pHPL is mixed and immediately divided into 14 aliquots (40 mL in 50 mL centrifuge tubes), maintained for 4-6 h at 20-24° C. until biogel formation is completed, and stored at 4° C. for 12-18 h. To remove fibrin, the clotted medium is brought to 37° C. The fibrin gel is then physically collapsed by exceeding the shear forces to the matrix, and the precipitated fibrin was pelleted at 2,500×g at 20° C. for 12 minutes. Finally, the supernatant is filtered (0.22 μm). Heparin-free, fibrinogen-depleted and EV-depleted medium is produced by single centrifugation step at 120,000×g for 3 h (employing a Sorvall MX120 or WX80 ultracentrifuge, and a fixed angle rotor, Thermo Scientific). The resulting supernatant is filtered through a 0.22 μm filter.

Enrichment, Purification and Characterization of EVs

To obtain EVs released by BM- or UC-MSC, cells are first maintained in heparin-free medium until they reach 70% confluence, whereafter cells are washed with PBS and medium is changed to fresh Heparin-free, fibrinogen-depleted and EV-depleted medium. Conditioned media (CM) are harvested after 48 hours. The CM is first filtered through a 0.22 μm filter to remove cell debris and large vesicles, followed by centrifugation at 30,000×g for 20 minutes to pellet larger microvesicles. The supernatants are subjected to centrifugation at 120,000×g for 3 hours to pellet the EV. The resulting pellets are either resuspended in PBS or Ringer-Lactate solution (for nanoparticle tracking analysis) or in alpha-MEM without supplements (for proteinase and RNase protection assay), or directly lysed in RNA lysis buffer (for RNA isolation, buffer from mirVANA miRNA Isolation Kit, AM1561, Ambion) or RIPA buffer (for Western Blot analysis; R0278, Sigma-Aldrich). EVs are stored at −80° C. prior to nanoparticle tracking analyses (NTA).

After collection of CM, MSCs are removed from the culture vessel by the addition of TrypLE Select CTS (A12859-01, Gibco), stained with trypan blue and counted using a hemocytometer, and analyzed by flow cytometry to obtain an accurate cell count at the time of harvest. This enables the definition of a cell equivalent (CE) dose for further investigation of the therapeutic activity.

$2\times10^6$ cells are used to obtain an immunophenotype of the cells by flow cytometry (FACS). In order to indicate the MSC phenotype approved for administration to humans in clinical trials, the cells should demonstrate an MSC phenotype to meet modified and improved criteria based upon the minimal criteria for MSCs set forward by the International Society for Cell Therapy (ISCT; Dominici et al., 2006) and approved by international authorities.

Purification Strategy—TFF Vs UC

In order to obtain therapeutically active EVs from large volumes of conditioned media various techniques are available (see for example Nordin et al., 2015 comparing both biochemical and biophysical purification aspects and demonstrating (by NTA, WB and LC/MS/MS) that ultrafiltration techniques generated EVs with the same proteome as those vesicles purified by ultracentrifugation, albeit with even higher yield and purity, as determined by the vesicle-to-protein ratio).

We confirm in our own studies that the purification process by ultracentrifugation is suitable for obtaining therapeutically active EVs. Tangential flow filtration (TFF) has been evaluated as an alternative, scalable method. Our data demonstrate, that TFF can be used to obtain MSC-derived EVs from large volumes (2-10 L) of MSC conditioned medium and that the resulting RNA profile is not substantially affected and deviating from the criteria set above.

2.4 Immunophenotyping and Determination of Cell Viability by Flow Cytometry

Immunophenotype and viability analysis of MSCs cultured is carried out according to the minimal criteria for defining MSC identity (Dominici et al., 2006). In brief, collected cells are centrifuged (300×g for 6 min), resuspended in 5% v/v sheep serum-containing blocking buffer to reach a concentration of $1.5\times10^7$ cells/mL and incubated for 20 minutes at +4° C. in dark. $3\times10^5$ cells are stained with mouse anti-human monoclonal antibodies against CD90 (IM1839U, Beckman Coulter, France), CD105 (MCHD10505, Life Technologies, Austria), CD14, CD19, CD34, CD45, CD73, HLA-II (DR) (345785, 345802, 345808, 550257, 347400 Becton Dickinson, Austria), or with corresponding isotype controls (345815, 345818, 555743, 345816, 349051, Becton Dickinson, Austria) for 25 minutes at +4° C. in dark. Thereafter samples are washed with cold PBS and resuspended in 100 μL 7AAD-containing PBS (1:10 dilution, 0.0005 w/v % final concentration) and stained for 10 minutes at room temperature protected from light. Finally 400 μL cold PBS is added and the samples are measured immediately using FACSCanto II flow cytometer (Becton Dickinson) until 1000 events were recorded per staining. Blue (488 nm) and red (633 nm) laser excited fluorescence signals are detected with the following standard light filters: FITC: 530/30 nm; PE: 585/42 nm; APC: 660/20 nm; 7AAD: 670LP. Results are analyzed with WinList software 8.0 (Verity Software House, Topsham, USA). [FSCA, SSCA] dot plot analyses are applied for debris exclusion, and a doublet discrimination panel is set on the FSC channel for the detection of height and width of the fluorescence signals. The ratio of the viable cells is determined on [SSC, 7AAD] dot plot.

2.5 RNA Isolation and Detection

RNA was isolated from EV pellets using mirVana miRNA Isolation Kit (AM1561, Ambion) according to the manufacturer's instructions for total RNA isolation. One microliter of isolated RNA was analyzed for quality, size distribution and yield with Agilent RNA 6000 Pico chips (5067-1513) on an Agilent 2100 Bioanalyzer (Agilent Technologies, Santa Clara, CA) according to the manufacturer's protocol.

2.6 Proliferation Assays

Proliferative capacity of MSC is monitored in real-time employing the impedance-based growth measurement system xCELLigence RTCA DP (Roche/ACEA) and E-Plates 16 (05469830001, Roche/ACEA). Experiments are performed according to the manufacturer's instructions. For each data set 500 or 1000 cells per well are seeded in quadruplicates. The impedance value of each well is automatically monitored by the xCELLigence system every 5 minutes over a period of 96 hours and expressed as a CI (cell index) value. The rate of cell growth is determined by comparing the percent difference in the mean normalized CI values between the cells.

2.7 Differentiation Assays

MSC were grown until confluence. Osteogenic differentiation was induced in medium supplemented with 0.1 μM dexamethasone (D4902, Sigma-Aldrich), 10 mM beta-glycerophosphate (G9422, Sigma-Aldrich) and 0.05 mM L-ascorbic acid (A4403, Sigma-Aldrich). Adipogenic differentiation was initiated in medium supplemented with 10 μg/ml insulin (10516, Sigma-Aldrich), 1 μM dexamethasone (D4902, Sigma-Aldrich), 0.1 mM indomethacin (Landesapotheke Salzburg, Austria), and 0.5 mM 3-isobutyl-1-methylxanthine (15879, Sigma-Aldrich). Media were changed every 3 days, and 14 days after differentiation induction cells were fixed with 4% paraformaldehyde (0335.3, Roth). Osteogenic differentiation was detected by staining with 0.5% Alizarin Red S (A5533, Sigma-Aldrich), adipogenic differentiation by staining with 1% Sudan III (S4136, Sigma-Aldrich).

2.8 Proteinase and RNase Protection Assay

EV pellets isolated from BM-MSC conditioned medium A were resuspended in 4 mL of alpha-MEM (without Dipeptiven and pHPL), filtered through a 0.22 μm filter to remove persistent precipitates and divided into four aliquots. One sample was incubated with proteinase K (0.05 μg/μl final concentration, Sigma, P6556) at 37° C. for 30 minutes. Proteinase K activity was inhibited by incubation at 90° C. for 5 minutes. Subsequently, the sample was incubated with RNase A (0.5 μg/μl final concentration, Sigma, R4642) for 20 minutes at 37° C. As controls, samples were treated identically but adding PBS instead of proteinase K and/or RNase A. Samples were centrifuged at 120,000×g for 3 hours (S55-A2 fixed angle rotor, k-factor: 39.8), and finally RNA was extracted and analysed as described above. To evaluate effectiveness of the proteinase K and RNase A digestion, purified vesicular RNA was incubated with proteinase K with or without subsequent RNase A treatment.

2.9 Western Blot Analysis

Pelleted EV derived from media and conditioned media or cells as control were lysed in 1×RIPA buffer (R0278, Sigma-Aldrich) supplemented with proteinase inhibitor cocktail (P8340, Sigma-Aldrich) and incubated at 4° C. for 15 minutes with occasional mixing, followed by centrifugation at 12,000×g and 4° C. for 10 minutes. Protein concentration was determined with Agilent Protein chip (5067-1575) on an Agilent 2100 Bioanalyzer (Agilent Technologies, Santa Clara, CA). One hundred μg of protein lysates were separated on 4-15% polyacrylamide gradient gels (456-1084, Bio-Rad Laboratories) and transferred onto nitrocellulose membranes (170-4158, Bio-Rad Laboratories). The membranes were blocked with 5% non-fat dry milk in Tris-buffered saline containing 0.1% Tween-20 (TBS-T) for one hour at room temperature and probed with primary antibodies against CD9 (sc-13118, Santa Cruz Biotechnology), CD81 (sc-7637, Santa Cruz Biotechnology), TSG101 (sc-7964, Santa Cruz Biotechnology), and GM130 (610823, BD Transduction Laboratories), all diluted 1:250 in TBS-T containing 0.5% non-fat dry milk, with incubation at room temperature for 4 hours. After extensive washing with TBS-T, the secondary antibody (goat anti-mouse HRP-conjugated, K4004, DAKO), diluted 1:200 in TBS-T containing 0.5% non-fat dry milk, was applied for one hour at room temperature. The proteins were detected with ECL Prime Western Blotting Detection Reagent (RPN2232, GE Healthcare) and ChemiDoc MP System (Bio-Rad).

2.10 Animal Study Design

All animal experiments and procedures were conducted in accordance with Austrian laws on animal experimentation and were approved by Austrian regulatory authorities (permit number BMWF-66.012/0035-WF/V/3b/2016). 26 male Fischer-344 rats (age 2 months; weight approx. 200 grams; Charles River Laboratories, Germany) were randomly assigned to seven groups. A 5 mm, critical-sized, mid-femoral defect was created (see section 2.4) and bone defects were treated with a scaffold only (control I; n=4), received a collagen sponge with a low dose of rhBMP2 (1

μg control II; n=2), or received a scaffold loaded with EVs derived from bone marrow-derived mesenchymal stromal cells (BM-MSCs; treatment I; n=5), or umbilical cord-derived mesenchymal stromal cells (UC-MSCs; treatment II; n=5). In addition, one group each received BMSC-EVs (treatment III; n=5) or UC-MSC-EVs (treatment IV; n=5) combined with 1 μg of rhBMP2 respectively. Assessment of bone healing was performed by radiography (2, 4, and 6 weeks post-surgery), by histology (6 weeks post-surgery; n=2 per treatment), and μCT analysis (6 weeks post-surgery).

2.11 Implant Preparation

Cylinders of equine collagen sponges (Ø6 mm, Biopad Collagen, Euroresearch s.r.l, Italy) were prepared using dermal punches (pfm medical, Germany). BMSC-EVs and UCMSC-EVs resuspended in a final volume of 50 μl lactated Ringer's solution (Fresenius Kabi, Austria) were combined with 30 μl 2% NOVATACH MVG GRGDSP alginate solution (FMC Biopolymer, Norway) and loaded onto a collagen sponge. Gelation at room temperature was induced by the addition of 10 μl of a $CaCl_2$ solution (0.7 g/L in sterile water). For the treatment groups III and IV 1 μg of rhBMP2 (Peprotech, Austria) was added to the alginate in addition to 50 μl of EV preparation. For control groups, scaffolds were either loaded with an alginate/NaCl solution only (control I) or with 1 μg rhBMP2 in alginate (control II) in a final volume of 80 μl. Scaffold were implanted immediately after preparation.

2.12 Surgical Procedure

A 5 mm critical-sized femoral defect was created according to a modified version of a previously published procedure (Kunkel et al., 2015, Betz et al., 2010, Einhorn et al., 1984). Briefly, surgeries were performed under isoflurane gas anesthesia (4% for induction, 2% for maintenance; SomnoSuite, Kent Scientific, U.S.A.) in oxygen (450 ml/min) and were warmed using an electric heating pad to prevent hypothermia (Harvard Apparatus; Holliston, MA). After aseptic preparation for surgery a 3-4 cm skin incision was made and the shaft of the femur was carefully exposed. After creating four drill holes using a 0.9 mm drill bit (Gebrüder Brasseler, Lemgo, Germany) two custom-made fixation plates were secured to the femur using 4 threaded Kirschner wires (MEDE Technik, Emmingen, Germany). A 5 mm segmental defect was created using a Gigli wire saw (0.9 mm; RISystem, Davos, Switzerland) and subsequently the site was thoroughly rinsed with sterile 0.9% saline solution. A collagen sponge (control or loaded with MSC-EVs and/or rhBMP2; see section 1.2) was press-fitted into the defect area and the wound was subsequently closed in layers. After surgery, each animal was given an antibiotic (clindamycin, 45 mg/kg) and the analgesic meloxicam (1 mg/kg) and 3 ml 0.9% NaCl solution. After recovery from anesthesia animals were allowed free movement and analgesia was provided by subcutaneous injection of buprenorphine (0.01 mg/kg; 2× daily) and meloxicam (1 mg/kg; 1× daily) for three days after surgery. Animals had free access to food and water and were frequently monitored daily for any complications or abnormal behavior.

2.13 Radiographic Assessment

Bone-healing was evaluated with serial radiography 4, 6, and 8 weeks post-surgery. While under general anesthesia, craniocaudal and mediolateral radiographs of the operated femur were obtained.

2.14 Microcomputed Tomography

Blinded micro-CT scans of the explanted femurs were conducted using a SCANCO μCT 50 system (Scanco Medical, Basserdorf, Switzerland). All samples were scanned nominally to the diaphyseal axis of the femora at 70 kVp and 200 μA using a voxel size of 34.4 μm. For 3D reconstruction slices of 34.4 μm were recorded and subsequently a VOI including the entire osteotomy gap and 1 mm proximally and distally was chosen for analysis. Bone volume (BV) is expressed as mean±SD.

2.15 Descriptive Histology

Explanted femurs were fixed in 4% paraformaldehyde in PBS- for 48 hours, and decalcified samples were embedded in paraffin according to routine histological procedures. Sections of 7 μm were stained with Masson's Goldner trichrome stain following standard protocols (Mulisch et al., 2010). All images were acquired by bright-field microscopy and were processed with Adobe Photoshop CS6. Only global corrections were performed (i.e. unsharp masking) and no specific feature within an image was manipulated.

3 Results 3.1 EV miRNA Profile

Mesenchymal stromal cells (MSCs) of various tissue origin display differential therapeutic effects despite their overall similar surface marker expression. Similarly, extracellular vesicles (EVs) that largely mediate the paracrine effects of MSC differ with respect to their protein and RNA content. EVs are purified from naive MSCs by differential ultracentrifugation and characterized by NTA and Western blotting. Agilent Bioanalyzer-based total RNA profiling and miRNA Next Generation Sequencing (NGS) were employed to identify differences in the EVs RNA content.

RNA profiling revealed that EVs from UC-MSC contained significantly larger amounts of total RNA and miRNAs than EV from BM-MSC. miRNA sequencing results confirmed the increased content of miRNAs found in UC-MSC-derived EVs. However, the most abundant miRNA in EV from all three naive tissue sources was miR-146a, which is involved in immunosuppressive processes (see FIG. 1). miR-146a was determined to be comprised about in a level of 80% to 100% in extracellular vesicles.

Immunosuppressive miRNAs packaged into EV from naive MSC may reflect their immunomodulatory potential. miRNA profiling can thus be employed to define the targeted therapeutic activity in MSC-derived EV to promote future preclinical and clinical trials. miRNA 146a-5p was used as the reference miRNA since this miRNA consistently showed the high values (see FIG. 1) in EVs prepared according to the procedure described herein. The values were set to 100%. All other percentages were given in relation to this value and did not reflect total content percentages. This miRNA profile was distinctly different from that shown by Baglio et al (2015). Baglio et al (2015) examined the relative proportion of individual miRNAs in the repertoire of total miRNA reads. In Baglio et al (2015), the 5 most abundant miRNAs (miR-486-5p, miR-10a-5p, miR-10b-5p, miR-191-5p and miR-222-3p in adipose tissue derived MSC exosomes, and miR-143-3p, miR-10b-5p, miR-486-5p, miR-22-3p and miR-21-5p in bone marrow-derived MSC exosomes, accounted for 43-59% of the total miRNA reads. To evaluate the relative distribution of miRNAs in cells and exosomes, cellular and exosomal miRNAs were ranked based on the reads per million (rpm) (herein also referred to as transcripts per million (TPM)) values and were compared to the 20 most represented miRNAs in cells and exosomes. MiRNAs miR-21-5p, miR-22-3p, miR-10b-5p and miR-222-3p, were among the most represented in both cells and exosomes, however various miRNAs were only present either in the list of cellular or in the list of exosomal highly represented miRNAs in Baglio et al (2015).

Despite some overlapping miRNAs, the profiles for bone marrow and adipose tissue derived MSC exosomes reported in Baglio et al (2015) differ from the miRNA profiles in extracellular vesicles obtained by the herein described methods (see above and below). Therefore, the purified extracellular-vesicles of the present invention are different compared to the vesicles purified in Baglio et al.

Biomolecular signature profiles are required to determine the identity of the therapeutic agent. This present profile is well suited to support the animal data in vivo as well as the in vitro cell differentiation and proliferation data.

miRNA sequencing of EVs from BM-MSCs and UC-MSCs derived from different donors revealed a consistent profile that supports the observed pro-osteogenic activity observed in vitro and in vivo:

hsa-miR-146a-5p hsa-miR-92a-3p hsa-miR-21-5p hsa-miR-30d-5p hsa-miR-148a-3p hsa-miR-320a hsa-let-7i-5p hsa-miR-221-3p hsa-let-7f-5p Further, hsa-miR-22-3p/hsa-miR-30d-5p could individually be determined as occurring in amounts less than 2% in relation to 100% of hsa-miR-146a-5p.

On the basis of the above findings, further characterization of the miRNA profiling can be carried out. For example, the quantification may be ranked according to miRNA abundance and/or levels. The purification of the extracellular vesicles was herein described above and below. Therefore, the miRNA profile in extracellular vesicles and a ranking according to the level of the miRNA abundance was also determined for extracellular-vesicles derived from UC-MSCs (see Table 1). Comparison of the miRNA content of UCMSC-derived vesicles obtained by either ultracentrifugation or tangential flow filtration (TFF) and grown in either HPL-containing standard medium (herein referred to as culture medium) revealed the sensitivity of the biological process of extracellular vesicle production.

The data revealed that the levels of particular miRNAs among the 20 most abundant miRNAs remained constant in the extracellular vesicle preparations compared to extracellular vesicles obtained from cells that had been maintained in serum free medium devoid of growth factor containing serum. For example, the hsa-miR-146a-5p, hsa-miR-92a-3p, hsa-miR-21-5p, hsa-miR-148a-3p, hsa-miR-221-3p, hsa-let-7i-5p, and hsa-let-7f-5p was constantly determined among the 20 most abundant miRNAs (see Table 1), whereas miR-22-3p, miR-222-3p, miR-486-5p and miR-191-5p were not determined among the 15 most abundant miRNAs.

In particular, miRNA 486 was not significantly not detected among the 20 most abundant miRNAs in extracellular-vesicles obtained by the herein described methods compared to the extracellular-vesicles purified by other strategies and in the presence of heparin.

The miRNA ranking differed from that reported of other cell types and lineages provided with the methodology of the prior art.

TABLE 1

Comparison of miRNA content of MSC-derived vesicles obtained by ultracentrifugation or tangential flow filtration (TFF) and grown in HPL-containing culture medium. The miRNA levels were similar in the extracellular vesicles isolated by either ultracentrifugation or TFF.

| Standard med./Ultracentr. | | Standard med./TFF | |
|---|---|---|---|
| miRNA | TPM | miRNA | TPM |
| hsa-miR-148a-3p | 97730 | hsa-miR-92a-3p | 89803 |
| hsa-miR-21-5p | 95111 | hsa-miR-21-5p | 85704 |
| hsa-let-7f-5p | 82777 | hsa-miR-146a-5p | 79871 |
| hsa-miR-146a-5p | 75778 | hsa-let-7f-5p | 52473 |
| hsa-let-7i-5p | 68000 | hsa-miR-100-5p | 48681 |
| hsa-let-7g-5p | 43773 | hsa-miR-148a-3p | 46263 |
| hsa-miR-92a-3p | 40092 | hsa-let-7i-5p | 41879 |
| hsa-miR-100-5p | 37871 | hsa-miR-30d-5p | 41366 |
| hsa-miR-151a-3p | 33527 | hsa-miR-151a-3p | 30775 |
| hsa-miR-103a-3p | 31518 | hsa-let-7a-5p | 28170 |
| hsa-let-7a-5p | 29677 | hsa-let-7g-5p | 25289 |
| hsa-miR-26a-5p | 28120 | hsa-miR-221-3p | 23922 |
| hsa-miR-584-5p | 19316 | hsa-miR-26a-5p | 23248 |
| hsa-miR-221-3p | 18175 | hsa-miR-10a-5p | 22793 |
| hsa-miR-10a-5p | 13547 | hsa-miR-584-5p | 22637 |
| hsa-miR-30d-5p | 12635 | hsa-miR-103a-3p | 17568 |
| hsa-miR-320a | 11538 | hsa-miR-486-5p | 17433 |
| hsa-miR-126-3p | 11388 | hsa-miR-320a | 13582 |
| hsa-miR-143-3p | 10742 | hsa-miR-25-3p | 11917 |
| hsa-miR-191-5p | 10406 | hsa-miR-143-3p | 11013 |

Upon serum starvation an overrepresentation of miRNA 100 was observed. Comparative studies indicated that the origin of miR-100 dates back to the bilaterian ancestor. In human cancers, miR-100 has been reported to function as either a oncogenic miRNA or a tumor suppressive miRNA, which depends on tumor types and microenvironment. miR-100 functions in numerous important biological processes such as metabolism, cell cycle, migration, epithelial-mesenchymal transition, differentiation and cell survival. Moreover, miR-100 re-sensitizes tumor cells to chemotherapeutic drugs.

Accordingly, the umbilical cord MSC derived (and bone marrow derived) extracellular vesicles obtained by the herein described methods contain a unique miRNA profile that distinguish them from bone marrow or adipose tissue MSC derived EV preparations.

3.2 Immunomodulation in MLR Assay

A robust immunosuppression potency assay has been established (Ketterl et al., 2015) using CFSE pre-labeled pooled and cryopreserved PBMCs, which can be tested off-the-shelf for mitogenesis-driven lymphocyte proliferation and MLR. The inhibitory potential of individual MSCs is compared to pooled MSCs as a reference normalizing donor variation in this combined assay format. We have modified and utilized this assay to evaluate the immunomodulatory potential of EVs. Notably, EVs from UC-MSCs perform comparable to parental UC-MSCs. This is a unique modification of a cell-oriented potency assay that aids in the in vitro determination of the immunomodulatory potential of purified EVs.

3.3 NTA (Nanoparticle Tracking Analysis)

EV suspensions were diluted in PBS to result in a concentration of 4-7×$10^7$ particles/mL. Amount and size of particles were measured using a ZetaView Nanoparticle Tracking Analyzer (ParticleMetrix). Minimum brightness was set at 20 arbitrary units (AU), sensitivity at 85 AU and temperature at 20° C. Five exposures at 11 measurement positions were recorded for each sample. Particle size was calculated according to the Stokes-Einstein equation by the ZetaView software. Data on particle numbers are presented as arithmetic mean±standard deviation (see FIG. 2).

3.4 General Animal Health

One animal from treatment group II (UC-MSC-EV) died 2 days after surgery due to unknown reasons. One animal each from treatment group II and treatment group III (BMSC-EVs plus 1 μg rhBMP2) had to be excluded from the study due to fixator plate loosening. All other animals showed normal behavior with non-restricted weight bearing 48 hours after surgery and no obvious signs of adverse reactions were observed after implantation of the collagen scaffolds.

3.5 Radiographic Evaluation, μCT, and Descriptive Histology

For the vast majority of the animals from the treatment groups calcified tissue had formed within the defect region 6 weeks post-osteotomy (FIG. 3). However, generally no bony union was achieved, despite the significant formation of immature bone tissue. For most cases a bony closure of the medullary canal with a variable amount of appositional bone formation was evident. In contrast, for those animals that had received the scaffold without EVs or rhBMPs (control I), only minimal amounts of calcified tissue was evident (FIG. 3). Interestingly, for one femur which had been treated with 1 μg rhBMP-2 only (control II) a significant amount of calcified tissue had formed 6 weeks post-surgery, whereas for the second animal no significant amount of new bone was seen, as evidenced by X-ray and μCT analysis (FIG. 3).

Comparisons of the bone volume (BV) formed within the defect area 6 weeks after the surgery revealed no significant differences ($p>0.05$) between the various treatment groups (FIG. 4). The median volumes (BV; see table 2 for overview) of newly formed bone for the control group I (scaffold only; n=4) and the control group II (1 μg rhBMP-2 only; n=2) were 2.94 $mm^3$ [range 0.02-7.34] and 15.78 $mm^3$ [range 2.33-29.24], respectively. For femurs treated with BM-MSC-EVs (treatment I; n=5) the median BV was 11.13 $mm^3$ [range 5.50-21.29] and treatment with UC-MSC-EVs (treatment II; n=3) resulted in 14.64 $mm^3$ [range 14.06-21.74] newly formed bone. Combination of BM-MSC-EVs (treatment III; n=4) or UC-MSC-EVs (treatment IV; n=5) with 1 μg rhBMP2 resulted in median bone volumes of 24.11 $mm^3$ [range 19.86-27.86] and 27.47 $mm^3$ [range 18.27-35.09], respectively. All treatments, with the exception of UC-MSC-EV (p=0.057; due to the lower number of samples), resulted in the formation of significantly more immature bone when compared to the animals receiving the scaffold only control ($p<0.05$; Mann-Whitney U test). Further, although not statistically significant, the treatment with UC-MSC induced moderately more tissue regeneration and the co-application of 1 μg rhBMP2 further enhanced bone formation. This was also confirmed by histology as shown in FIG. 5, where areas of immature woven bone (WB) and also sections of compact bone (B) were detected in the defect area. Although not quantitatively assessed by histomorphometry, treatment with UC-MCS either with or without 1 μg rhBMP2 resulted in moderately more immature, woven bone-like areas (see FIG. 5).

TABLE 2

Bone Volumes (BV) in $mm^3$ determined from μCT scans

| BV ($mm^3$) | Treat. I (BM-MSC-EV; n = 5) | Treat. II (UC-MSC-EV; n = 3) | Treat. III (BM-MSC-EV + 1 μg rhBMP; n = 4) | Treat. IV (UC-MSC-EV + 1 μg rhBMP; n = 5) | Ctrl. I (scaffold only; n = 4) | Ctrl. II (1 μg rhBMP2; n = 2) |
|---|---|---|---|---|---|---|
| Median | 11.13 | 14.64 | 24.11 | 27.47 | 2.944 | 15.78 |
| Minimum | 5.495 | 14.06 | 19.86 | 18.27 | 0.0223 | 2.326 |
| Maximum | 21.29 | 21.74 | 27.86 | 35.09 | 7.339 | 29.24 |
| Mean | 12.32 | 16.82 | 23.98 | 25.87 | 3.313 | 15.78 |
| Std. Deviation | 6.317 | 4.277 | 4.305 | 6.818 | 3.404 | 19.03 |
| Lower 95% CI of mean | 4.473 | 6.189 | 17.13 | 17.4 | −2.103 | −155.2 |
| Upper 95% CI of mean | 20.16 | 27.44 | 30.84 | 34.33 | 8.728 | 186.8 |

4.2 Bone Formation Assessed by Rat Femur Segmental Defect Model

Animals of the rat femur segmental defect model were treated with BMSC-EV, UCMSC-EV and BMSC-EV plus BMPs2, and UCMSC-EV plus BMP2. For the vast majority of the animals from the treatment groups calcified tissue had formed within the defect region 6 weeks post-osteotomy. However, no bony union was achieved, despite the significant formation of immature bone tissue. Treatment with vesicles with or without a low dose of BMP2 resulted in a significantly higher bone volume (BV) when compared to the scaffold only group. For most cases a bony closure of the medullary canal with a variable amount of appositional bone formation was evident. In contrast, for those animals that had received the scaffold without EVs or rhBMPs (control I), only minimal amounts of calcified tissue was evident. Interestingly, for one femur which had been treated with 1 μg rhBMP-2 only (control II) a significant amount of calcified tissue had formed 6 weeks post-surgery, whereas for the second animal no significant amount of new bone was seen, as evidenced by X-ray and μCT analysis.

In summary, treatment of a critical-size defect with EVs isolated from MSCs resulted in the formation of significant amounts of calcified tissue. The treatment with UC-MSC-EVs induced moderately more tissue regeneration when compared to the treatment with BM-MSC-EVs. Further, the co-application of 1 μg rhBMP2 further enhanced bone formation. A dose of 1 μg rhBMP2 per defect may represent a low dose. By downscaling the clinical dose based on body weight (12 mg of rhBMP2 for patients with an average body weight of 75 kg), a dose of 33.3 μg/200 g would be administered in a preclinical study in rats. Interestingly, Yasko et al., compared rhBMP2 dosages in a 5 mm rat osteotomy defect and found that 11 μg rhBMP2 resulted in endochondral bone formation and gap bridging, while a reduction to 1.4 μg rhBMP2 could not induce healing in this critical size defect. Therefore, the co-administration of -EVs derived from MSCs further enhanced the osteoinductivity of rhBMP2.

EXAMPLE 2: A GMP-GRADE STANDARD PROTOCOL FOR EXCLUSIVELY HUMAN MESENCHYMAL STROMAL CELL-DERIVED EXTRACELLULAR VESICLES

As an alternative to serum-free cell culture conditions, serum/HPL depleted of its EV can be used for investigation and production of cell-derived EV. Several protocols for the depletion of FBS-derived EV have been reported and applied for EV research in the past, but the use of EV-depleted HPL for MSC propagation has not been reported thus far. A protocol for producing a medium is described that is free of xenogenic substances and based on supplementation with EV-depleted pHPL. The effect of this medium was evaluated on bone marrow (BM)-MSC morphology, immunophenotype, proliferation and differentiation properties as well as on RNA and protein composition in the purified EV. The data reveal that media produced under GMP compliant conditions and supplemented with 10% EV-depleted pHPL are suitable for the production and characterization of BM-MSC-derived EV.

Materials and Methods

Medium Preparation

Heparin-free and fibrinogen-depleted medium (medium A) was prepared as follows: Alpha-modified Minimal Essential Medium Eagle (alpha-MEM, M4526, Sigma-Aldrich) was supplemented with 5 mM (N2)-L-Alanyl-L-Glutamine (Dipeptiven, 11051014, Fresenius Kabi, Austria) and 10% pHPL. pHPL was produced as described earlier (Schallmoser et al., 2007). The mixture was immediately divided into 14 aliquots (40 mL in 50 mL centrifuge tubes), maintained for 4-6 h at 20-24° C. until biogel formation was completed, and stored at 4° C. for 12-18 h. To remove fibrin, the clotted medium was brought to 37° C. The fibrin gel was then physically collapsed, and the precipitated fibrin was pelleted at 2,500×g at 20° C. for 12 minutes (Laner Plamberger et al., 2015). Finally, the supernatant was filtered (0.22 μm) to yield medium A. Heparin-free, fibrinogen-depleted and EV-depleted medium (medium B) was produced from medium A by a single ultracentrifugation step at 120,000×g for 3 h (employing a Sorvall MX120 ultracentrifuge, fixed angle rotor S50-A, k-factor 60.7, Thermo Scientific). The resulting supernatant was filtered through a 0.22 μm filter, to yield medium B (EV-depleted medium). FBS-containing medium was prepared by adding 10% FBS (CC-4101A, Lonza) and 5 mM Dipeptiven to alpha-MEM, and immediate filtration (0.22 μm). Serum-/pHPL-free medium (medium C) was generated by adding 5 mM Dipeptiven to alpha-MEM, followed by filtration (0.22 μm). pHPL-reduced medium (medium D) was obtained by fivefold dilution of medium A with medium C; pHPL-reduced and EV-depleted medium (medium E) was prepared by fivefold dilution of medium B with medium C (see Table 3).

TABLE 3

Overview of media used in this study.

| Medium name | Medium content |
| --- | --- |
| Medium A (10% pHPL) | alpha-MEM + 5 mM Dipeptiven + 10% pHPL |
| Medium B (10% HPL/EV-depleted) | alpha-MEM + 5 mM Dipeptiven + 10% pHPL, EV-depleted |
| Medium C (serum-/pHPL-free) | alpha-MEM + 5 mM Dipeptiven |
| Medium D (2% pHPL) | alpha-MEM + 5 mM Dipeptiven + 2% pHPL |
| Medium E (2% pHPL/EV-depleted) | alpha-MEM + 5 mM Dipeptiven + 2% pHPL, EV-depleted |
| FBS Medium | alpha-MEM + 5 mM Dipeptiven + 10% FBS |

All pHPL-based media are heparin-free and fibrinogen-depleted.

Abbreviations: pHPL, pooled human platelet lysate; EV, extracellular vesicles; FBS, fetal bovine serum.

Cell Culture

Cells were cultured at 37° C. and 5% $CO_2$. Experiments were performed with two different primary human BM-MSC preparations. One BM aspirate was directly obtained from the University Clinic for Blood Group Serology and Transfusion Medicine, Paracelsus Medical University, Salzburg (Austria). The second BM aspirate was purchased from AllCells (California, USA). Both donors had signed an informed consent. BM-MSC were isolated from bone marrow as described (Lotvall, 2014) and tested negative for mycoplasma. Following primary cell isolation, medium A was used as the basic cell culture medium. For all experiments, cells were kept in 30 mL medium per T225 flask.

Isolation of pHPL-, FBS- and BM-MSC-Derived Extracellular Vesicles

EV present in pHPL were obtained by ultracentrifugation at 120,000×g for 3 hours. EV from FBS were isolated from alpha-MEM containing 10% FBS in the same manner. To obtain EV released by BM-MSC, cells were first maintained in medium A. At 70% confluence, cells were washed with PBS and medium was changed to fresh medium. Conditioned media (CM) were harvested after 48 hours. The CM were first filtered through a 0.22 μm filter to remove cell debris and large vesicles, followed by ultracentrifugation at 30,000×g for 20 minutes to pellet larger microvesicles. The supernatants were subjected to ultracentrifugation at 120,000×g for 3 hours to sediment the EV. The resulting pellets were either resuspended in PBS (for nanoparticle tracking analysis) or in alpha-MEM without supplements (for proteinase and RNase protection assay), or directly lysed in RNA lysis buffer from mirVANA miRNA Isolation Kit, AM1561, Ambion (for RNA isolation) or RIPA buffer (for Western Blot analysis; R0278, Sigma-Aldrich). Ultracentrifugation was performed in an S50-A fixed angle rotor (k-factor: 60.7, Thermo Scientific). EV were stored at −80° C. prior to nanoparticle tracking analyses (NTA). After collection of CM, cells were removed from the culture vessel by the addition of TrypLE Select CTS (A12859-01, Gibco), stained with trypan blue and counted using a hemocytometer for immunophenotyping and determining the live-dead ratio of the harvested cells.

Immunophenotyping and Determination of Cell Viability by Flow Cytometry

Immunophenotype and viability analysis of BM-MSC was carried out according to the minimal criteria for defining MSC identity (Dominici et al., 2006). In brief, collected cells were centrifuged (300×g for 6 min), resuspended in 5% v/v sheep serum-containing blocking buffer to reach a concentration of $1.5\times10^7$ cells/mL and incubated for 20 minutes at +4° C. in dark. $3\times10^5$ cells were stained with mouse anti-human monoclonal antibodies against CD90 (IM1839U, Beckman Coulter, France), CD105 (MCHD10505, Life Technologies, Austria), CD14, CD34, CD45, CD73, HLA-II (DR) (345785, 345802, 345808, 550257, 347400 Becton Dickinson, Austria), or with corresponding isotype controls (345815, 345818, 555743, 345816, 349051, Becton Dickinson, Austria) for 25 minutes at +4° C. in dark. Thereafter samples were washed with cold PBS and resuspended in 100 μL 7AAD-containing PBS (1:10 dilution, 0.0005 w/v % final concentration) and stained for 10 minutes at room temperature protected from light. Finally, 400 μL cold PBS was added and the samples were measured immediately using a FACSCanto II flow cytometer (Becton Dickinson). For each measurement 10.000 events were recorded per staining. Blue (488 nm) and red (633 nm) laser excited fluorescence signals were detected with the following standard light filters: FITC: 530/30 nm; PE: 585/42 nm; APC: 660/20 nm; 7AAD: 670LP. Results were analyzed with WinList software 8.0 (Verity Software House, Topsham, USA). [FSCA, SSCA] dot plot analyses were applied for debris exclusion, and a doublet discrimination panel was set on the FSC channel for the detection of height and width of the fluorescence signals. The ratio of the viable cells was determined on [SSC, 7AAD] dot plot.

RNA Isolation and Detection

RNA was isolated from EV pellets using mirVana miRNA Isolation Kit (AM1561, Ambion) according to the manufacturer's instructions for total RNA isolation. One microliter of isolated RNA was analyzed for quality, size distribution and yield with Agilent RNA 6000 Pico chips (5067-1513). The profile (based on size discrimination/nucleotide length determination) of the miRNA was determined by Agilent Small RNA chips (5067-1548) on an Agilent 2100 Bioanalyzer (Agilent Technologies, Santa Clara, CA) according to the manufacturer's protocol.

Nanoparticle Tracking Analysis

EV suspensions were diluted in PBS to obtain $4\text{-}7\times10^7$ particles/mL. Amount and size of particles were measured using a ZetaView Nanoparticle Tracking Analyzer (ParticleMetrix). Minimum brightness was set to 20 arbitrary units (AU), sensitivity to 85 AU and temperature to 20° C. Five exposures at 11 measurement positions were recorded for each sample. Particle size was calculated according to the Stokes-Einstein equation by the ZetaView software.

Proliferation Assays

The proliferative capacity of BM-MSC was monitored in real-time employing the impedance-based growth measurement system xCELLigence RTCA DP (Roche/ACEA) and E-Plates 16 (05469830001, Roche/ACEA). Experiments were performed according to the manufacturer's instructions. For each data set 500 or 1000 cells per well were seeded in quadruplicates. The impedance value of each well was automatically monitored by the xCELLigence system every 5 minutes over a period of 96 hours and expressed as a CI (cell index) value. The rate of cell growth was determined by comparing the difference in the mean normalized CI values between the cells.

Differentiation Assays

BM-MSC were grown in medium A until confluence. Osteogenic differentiation was induced using medium supplemented with 0.1 μM dexamethasone (D4902, Sigma-Aldrich), 10 mM beta-glycerophosphate (G9422, Sigma-Aldrich) and 0.05 mM L-ascorbic acid (A4403, Sigma-Aldrich). Adipogenic differentiation was initiated using medium supplemented with 10 μg/ml insulin (10516, Sigma-Aldrich), 1 μM dexamethasone (D4902, Sigma-Aldrich), 0.1 mM indomethacin (Landesapotheke Salzburg, Austria), and 0.5 mM 3-isobutyl-1-methylxanthine (15879, Sigma-Aldrich). Media were changed every 3 days, and 14 days after induction of differentiation cells were fixed with 4% paraformaldehyde (0335.3, Roth). Osteogenic differentiation was detected by staining with 0.5% Alizarin Red S (A5533, Sigma-Aldrich), adipogenic differentiation by staining with 1% Sudan III (S4136, Sigma-Aldrich).

Proteinase and RNase Protection Assay

EV pellets isolated from BM-MSC conditioned medium A were resuspended in 4 mL of alpha-MEM (without Dipeptiven and pHPL), filtered through a 0.22 μm filter to remove undisssolved precipitates and divided into four aliquots. One sample was incubated with proteinase K (0.05 μg/μL final concentration, Sigma, P6556) at 37° C. for 30 minutes. Proteinase K activity was inhibited by incubation at 90° C. for 5 minutes. Subsequently, the sample was incubated with RNase A (0.5 μg/μL final concentration, Sigma, R4642) for 20 minutes at 37° C. As controls, samples were treated identically but adding PBS instead of proteinase K and/or RNase A. Samples were centrifuged at 120,000×g for 3 hours (S55-A2 fixed angle rotor, k-factor: 39.8), and finally RNA was extracted and analysed as described above. To evaluate effectiveness of the proteinase K and RNase A digestion, purified vesicular RNA was incubated with proteinase K with or without subsequent RNase A treatment.

Western Blot Analysis

EV derived from growth media or conditioned media, or cells (as control) were lysed in 1×RIPA buffer (R0278, Sigma-Aldrich) supplemented with proteinase inhibitor cocktail (P8340, Sigma-Aldrich) and incubated at 4° C. for 15 minutes with occasional mixing, followed by centrifugation at 12,000×g at 4° C. for 10 minutes. Protein concentration was determined using an Agilent Protein chip (5067-1575) on an Agilent 2100 Bioanalyzer (Agilent Technologies, Santa Clara, CA). One hundred μg of protein lysates were separated on 4-15% gradient polyacrylamide gels (456-1084, Bio-Rad Laboratories) and transferred onto nitrocellulose membranes (170-4158, Bio-Rad Laboratories). The membranes were blocked with 5% non-fat dry milk in Tris-buffered saline (TBS) containing 0.1% Tween-20 (TBS-T) for one hour at room temperature and probed with primary antibodies against CD9 (sc-13118, Santa Cruz Biotechnology), CD81 (sc-7637, Santa Cruz Biotechnology), TSG101 (sc-7964, Santa Cruz Biotechnology), and GM130 (610823, BD Transduction Laboratories), all diluted 1:250 in TBS-T containing 0.5% non-fat dry milk, with incubation at room temperature for 4 hours. After extensive washing with TBS-T, the secondary antibody (goat anti-mouse HRP-conjugated, K4004, DAKO), diluted 1:200 in TBS-T containing 0.5% non-fat dry milk, was applied for one hour at room temperature. Proteins were detected with ECL Prime Western Blotting Detection Reagent (RPN2232, GE Healthcare) and ChemiDoc MP System (Bio-Rad).

Statistical Methods

Data are presented as arithmetic mean±standard error of the mean (SEM). Data were tested for Gaussian distribution using the Kolmogorov-Smirnov normality test and for outliers by Grubb's test. Data were compared using two-tailed unpaired t-test (*, $p<0.05$; , $p<0.01$; *, $p<0.001$). The significance level was 0.05 (95% confidence intervals). Analysis was achieved using GraphPad Prism 5 software and Microsoft Office EXCEL 2010.

Results

A Single Ultracentrifugation Step Eliminates RNA-Containing EV Derived from pHPL Below Detection Limit The standard medium A used in this study is entirely free from xenogenic substances and is supplemented with 10% pHPL. For depletion of pHPL-derived EV, medium A was centrifuged at 120,000×g for three hours. The resulting supernatant is referred to as medium B (EV-depleted medium), the resulting pellet was used to analyze the pHPL-derived EV in medium A. To assess the efficacy of EV depletion, medium B was subjected to another 3-hour centrifugation step at 120,000×g, and the EV yield from medium A and B was compared (FIG. 7). Following the single centrifugation step at 120,000×g for three hours, only 18.8±2.5% of nanoparticles obtained from medium A were isolated from medium B (FIG. 7*a*). Medium supplemented with 10% FBS instead of pHPL contained significantly fewer nanoparticles (FIG. 7*a*). The size distribution for EV isolated from any of the three medium types was comparable with a mean diameters of 126 nm for pHPL-derived EV and 124 nm for FBS-derived EV (see FIG. 13). The typical EV/exosome protein markers CD9, CD81, and TSG101 were detected in pHPL-based EV preparations (see FIG. 9*e*). RNA analysis of EV pellets obtained after centrifugation of equal amounts of medium A, B, or FBS-supplemented medium revealed differences in RNA composition (FIG. 7*b*). Although fewer particles could be recovered from the FBS-based medium than from pHPL-based medium, FBS-derived particles contained more RNA than pHPL-derived particles. We also detected a high portion of small RNA species as well as RNA species up to 1000 nucleotides (nt) in FBS-derived particles, while pHPL particles were mainly composed of small RNAs. The RNA concentration of particles obtained from medium B was only 8 pg/μL±2 pg/μl, which is below the detection limit of the Agilent RNA Pico system (FIG. 7*b*). Thus, a single centrifugation step at 120,000×g for three hours is sufficient to remove detectable amounts of RNA-containing pHPL EV from 10% HPL containing medium.

BM-MSC Propagated in EV-Depleted Medium Retain their Characteristic Morphology, Phenotype, Viability and Differentiation Potential, but Exhibit Slightly Decreased Proliferation Potential We examined whether the EV-depleted medium is suitable for propagation and ex vivo expansion of MSC. BM-MSC isolated from two different donors and cultured in EV-depleted medium were tested for surface marker expression, proliferation and differentiation potential. No morphological changes could be observed between BM-MSC grown in medium A versus medium B (see FIG. 17). BM-MSC cultured in medium B continued to display the characteristic fibroblast-like morphology, and MSC-specific surface marker expression was unaltered after cultivation in medium B for two passages (FIG. 8*a* and FIG. 18). Almost 100% of cells (>98.42%) stained positive for the MSC markers CD73, CD90, and CD105, while few cells (<0.20%) stained positive for hematopoietic markers CD14, CD34, CD45, and HLA-DR. Also, cell viability was unaltered as determined by flow cytometric viability testing (minimum cell viability 94.9%).

The proliferation rate of BM-MSC propagated in medium B did not change significantly after 48 hours but was decreased by 13% after 96 hours, compared to cells in medium A (FIG. 8*b* and FIG. 19). However, there was no significant difference in proliferation irrespective of a prior propagation of the cells in either medium A or B. The proliferation rate did not further decrease after a second passage in medium B. The potential of BM-MSC to differentiate into osteoblasts and adipocytes in the EV-depleted medium as basal differentiation medium was comparable to that observed with standard medium A as a basis (FIG. 8*c* and FIG. 20).

EV-Depleted Medium Conditions Result in Enrichment of BM-MSC-Derived EV

Next we analyzed the EV released from cells expanded in EV-depleted medium. BM-MSC were first grown in medium A to reach a confluence of 70%, followed by a medium change to either fresh medium A or medium B. EV were purified from conditioned media after 48 hours. CM B contained on average 70% fewer particles than CM A, when calculated either per cell or per mL (FIGS. 9*a*, 9*b* and FIGS. 21*a*, 21*b*). The number of particles detected in CM A ($2.13\times10^9$ particles per mL) was not significantly elevated compared to the number of particles purified from starting medium A ($1.97\times10^9$ particles per mL; FIG. 9*b*). In contrast, the amount of particles detected in CM B revealed a twofold increase compared to the starting medium B (FIG. 9*b*). The mean diameter of EV isolated from both CM was 125 nm and corresponded to that of pHPL-derived nanosized EV particles (see FIG. 15).

EV RNA profiles from identical volumes of CM demonstrated that CM A contained more vesicular RNA than CM B, but that the size distribution of isolated RNA was similar (FIGS. 9*c*, 9*d* and FIG. 21*c*). CM A contained three times more EV than CM B, explaining the increased total amount of vesicular RNA. The same volume of medium A, however, contained little overall RNA, and in medium B, the overall RNA level was below the detection limit of the assay (FIG. 9*c*).

To confirm that the RNA purified from BM-MSC-derived EV pellets is present in vesicles and not in extracellular protein-RNA complexes, EV pellets derived from cells cultured in medium A were treated with RNase, with or without pre-treatment with proteinase K. Proteinase K digestion was optimized using cell lysates (see FIG. 14), proteinase K and RNase A treatments were controlled by incubation of purified vesicular RNA with proteinase K with or without subsequent RNase A digestion (FIG. 10*c*). RNA profiling revealed that RNA from cell-derived EV pellets was protected from RNase treatment, even in combination with proteinase K treatment (FIGS. 10*a* and 10*b*), indicating that the isolated RNA originated from vesicles rather than from protein-RNA complexes. The RNA yield in all four combinations (FIGS. 10*a* and 10*b*) is lower than that observed in other RNA isolations (see FIG. 9*c*). This loss may be explained by the introduction of a second centrifugation step to collect the EV after RNase/proteinase K treatment. EV/exosomal protein markers CD9, CD81, and TSG101 were detected in EV harvested from CM A, CM B, as well as medium A and B, while the Golgi marker GM130 was not detectable in the EV isolates (FIG. 9*e* and FIG. 21*d*). Notably, EV pellets from CM A and medium A showed a higher expression of CD9 than EV from CM B and medium B. CD9 is one of the most abundant protein on the surface of platelets and is required for the microparticle release, and CD9 was demonstrated on platelet-derived exosomes. Thus, the majority of the CD9 signal in EV from CM A may originate from pHPL-derived vesicles. Apart from the difference in CD9 expression, EV harvested from CM A and CM B showed similar expression of the tested proteins. Analysis of cell lysates compared to lysates from EV preparations revealed an increased electrophoretic mobility of CD81 in cell lysates (FIG. 9*e* and FIG. 21*d*). This may reflect a reduced palmitoylation level of CD81 in the cell lysates. Palmitoylation can occur on at least six cysteine residues of CD81, leading to a difference in molecular mass of several kDa. Taken together the use of EV-depleted medium leads to EV pellets enriched in BM-MSC-derived EV.

pHPL-Reduced Culture Conditions Strongly Affect MSC Proliferation and Differentiation Capacities as Well as EV RNA Profiles Media formulations using reduced pHPL levels (e.g. 2% versus 10%) seem advantageous for large scale expansions and clinical scale EV purification, as smaller amounts of fibrinogen-depleted and EV-depleted medium (medium B) have to be produced. To assess whether such media are equally suitable, we compared BM-MSC characteristics and RNA profiles of EV released in 10% pHPL (medium A), 10% pHPL/EV-depleted (medium B), 0% pHPL (serum-/pHPL-free, medium C), 2% pHPL (medium D), and 2% pHPL/EV-depleted (medium E) alpha-MEM (see Table 3). Flow cytometric analyses indicated no change in the MSC immunophenotype after two passages in pHPL-reduced media D and E (FIG. 11*a* and FIG. 18). BM-MSC stop proliferation in serum-/pHPL-free alpha-MEM (medium C)—thus, BM-MSC were maintained in medium C for five days prior to flow cytometric analysis. Analysis of the properties of cells in medium C revealed a shift in green and red fluorescence intensity of negative markers and isotype controls of the investigated proteins. This fluorescence shift may be explained by an increased autofluorescence of starving cells due to their changed metabolic state [9]. However, this phenomenon does not reveal an altered immunophenotype of BM-MSC grown in medium C (FIG. 11*a* and FIG. 18).

Notably, cells showed no signs of increased cell death in either medium, as investigated by microscopy (see FIG. 17) and FACS-mediated viability testing (minimum cell viability of 94.9%).

When BM-MSC were transferred from medium A to medium D (2% pHPL) or medium E (2% pHPL/EV-depleted), we detected a reduction in the proliferative capacity to 81% and 72.5%, respectively, after 48 hours. After 96 hours, proliferation in media D and E were reduced to 56% (donor AC 1-001)/62% (donor DA001) and 49% (donor AC 1-001)/59% (donor DA001), respectively, compared to cells in medium A (FIG. 11*b* and FIG. 19).

The most striking differences between cells cultured in 10% pHPL versus 2% pHPL or 0% pHPL were observed for their differentiation potential. With serum-/pHPL-free or pHPL-reduced media as basal differentiation medium, BM-MSC exhibited a significantly increased propensity for matrix mineralization following chemical induction of osteogenic differentiation (FIG. 8*c* and FIG. 20). Conversely, the capacity of BM-MSC to differentiate into adipocytes was strongly reduced in 2% pHPL-containing media, and undetectable in serum-/pHPL-free medium.

To further characterize EV released by BM-MSC cultured in pHPL-reduced or serum-/pHPL-free media, cells were first maintained in standard medium A until 70% confluence, followed by a period of 48 hours in media C, D, or E and subsequent EV isolation. CM D contained 17.6±1.9% (donor AC 1-001)/22.5±0.5% (donor DA001), CM E 8.8±0.4% (donor AC 1-001)/11.8±0.4% (donor DA001) of the amount of nanosized EV particles detected in CM A per cell. In CM C, only 4±0.4% (donor AC 1-001)/6.3±0.5% (donor DA001) of the number of EV determined for CM A per cell were detected (FIG. 12*a* and FIG. 21*a*). Medium C did not contain any detectable nanoparticles (FIG. 12*b*). These data support the conclusion that particles measured in CM C originated from BM-MSC. Medium D was found to harbor 18.3±1.97%, and medium E 5.1±0.37% of the particles measured in medium A (FIG. 12*b*). EV harvested from an equal volume of the different CM showed significant differences in their RNA profiles. When cells were propagated in serum-/pHPL-free medium, the profile for vesicular RNA revealed the presence of larger amounts of small RNA species as well as a shift towards larger RNA species compared to 10% pHPL-containing media (FIGS. 12*c*, 12*d* and FIG. 21*c*). Larger amounts of small RNAs as well as RNA species containing more than 200 nt were also detected in cells maintained in pHPL-reduced conditions compared to 10% pHPL conditions (FIG. 12*e*, 12*f*, 12*g*, 12*h* and FIG. 21*c*), although fewer EV were detected per mL CM (FIG. 12*b* and FIG. 21*b*). The RNA pattern of EV harvested from the two pHPL-reduced CM types were similar, with more RNA detectable in CM without prior pHPL depletion (FIGS. 12*i*, 12*j* and FIG. 21*c*). EV/exosomal protein markers (CD9, CD81, TSG101) were detected in EV obtained from CM C, CM D, and CM E, while Golgi marker GM130 was not identified in these samples (FIG. 9*e*). Similar to EV derived from CM B and medium B, EV obtained from serum-/pHPL-free conditioned medium (CM C) and pHPL-reduced/pHPL EV-depleted conditioned medium (CM E) showed reduced expression of CD9 compared to EV from medium A, CM A, and CM D, the latter three containing pHPL EV.

Thus, BM-MSC propagated in pHPL-reduced or entirely serum-/pHPL-free media display variations in their proliferation and differentiation potential and release EV with altered RNA contents in comparison to cells cultured in standard medium.

In this study, a protocol was developed for the production of a pHPL-supplemented medium that is fibrinogen-depleted, free of non-human components and depleted of pHPL-derived EV, and investigated its suitability for the collection and characterization of human BM-MSC-derived EV.

This pHPL EV depletion protocol demonstrated considerable effectiveness in terms of eliminating vesicle-derived RNA. After centrifugation, no RNA-containing pHPL EV were detected. The overall nanoparticle content in the EV-depleted medium was reduced to around 19% of the starting content Evidence was provided that pHPL EV-depleted medium was suitable for propagation and large scale expansion of BM-MSC. Cells displayed high viability, exhibited characteristic MSC immunophenotype and were able to differentiate into osteogenic and adipogenic cells. The proliferation rate was decreased to 87% of the rate in standard pHPL medium after 96 hours. However, standard pHPL medium can be used for cell propagation until the desired cell confluence is reached, and changed for EV-depleted medium only prior to EV collection, thereby circumventing a longer EV production time due to decreased proliferative capacity of the parental cells. Application of EV-depleted medium for the production of BM-MSC-derived EV showed that the overall EV RNA pattern remained unchanged. The RNA profiles reflected the EV RNA content and composition. RNA was protected from proteinase K and RNase degradation indicating that the RNA purified from the EV pellets is present inside the membrane-encircled compartment of the vesicles that cannot be penetrated by proteinase K, and is not part of larger, RNA protecting structures such as AGO-2 or HDL.

BM-MSC EV harvested from cells propagated in standard pHPL medium may represent a mixture of BM-MSC-derived EV and pHPL-derived EV. In standard pHPL medium, the amount of nanoparticles prior to cell propagation was comparable to that in the conditioned medium after 48 hours. Thus, uptake and/or degradation of EV and release of EV by BM-MSC seemed to be balanced under this medium condition. In contrast, the conditioned pHPL EV-depleted medium contained twice the amount of nanoparticles determined in the pHPL EV-depleted starting medium, suggesting that in BM-MSC cultured in a medium, which was reduced by 81.2% in pHPL-derived EV, the release of EV can exceed their uptake/degradation. Significant amounts of RNA in EV-depleted medium were not detected. Thus, the RNA present in EV from pHPL EV-depleted conditioned medium originated from BM-MSC.

Removal of serum-/HPL-derived EV from a culture medium prior to collection of CM for EV enrichment from any cell type is recommended in order to yield an exclusively cell-derived EV population. Cell-derived EV fractions of highest achievable purity and a minimum of co-purifying substances are required to determine their therapeutic effect and to exclude that any measurable therapeutic effect arises from HPL-derived EV. HPL contains a large amount of growth factors and cytokines that contribute to tissue regeneration. A reduction of pHPL from 10% to 2% with or without prior EV-depletion strongly promoted the osteogenic differentiation potential of BM-MSC, but decreased the differentiation towards adipocytes. Also in serum-/pHPL-free alpha-MEM, BM-MSC displayed elevated osteogenic differentiation, but showed no sign of adipogenic differentiation.

EXAMPLE 3

Cytokine Profiling of Extracellular Vesicle Preparations Obtained by the Methods Provided Herein Comparative analysis of cytokine content in extracellular-vesicle preparations from cells expanded in the presence of HPL or in synthetic media was performed. The extracellular-vesicles were analyzed by the ProcartaPlex multiplex immunoassays for the Luminex platform (Invitrogen; ProcartaPlex Mix&Match Human 20-plex (affymetrix eBioscience), Cat.no.: EPX200-19407-801, Lot no.: 140982000). ProcartaPlex multiplex immunoassays are bead-based assays for protein quantification based on the principles of a sandwich ELISA with the use of Luminex xMAP (multianalyte profiling) technology. ProcartaPlex assays are suitable for use with serum, plasma, cell and tissue lysates, and cell culture supernatants. Assays are provided in multiple formats across six species (including human, mouse, rat, nonhuman primate, porcine, and canine).

The use of multiplex immunoassays for multiple analyte detection is a valuable tool for the comprehensive study of biological systems. As these systems are comprised of networks of secreted proteins including cytokines, chemokines, growth factors, and other proteins, multiplex immunoassays are an efficient method for biomarker profiling of a large set of proteins from a small sample; see INVITROGEN's procartaplex multiplex immunoassays brochure for more details.

The cytokine profiles of UC-MSC EVs obtained from cells either grown in standard HPL containing medium and serum-free synthetic medium and enriched by either ultracentrifugation (Ultracentrif.) or tangential flow filtration (TFF) were compared.

For each assay 50 microliter of EV solution were used, corresponding to a cell equivalent of $20\times10^6$ cells.

Any cytokine detectable in HPL but not in synthetic medium indicated the contribution of the platelet lysate. Only cytokines that were detected in both preparations were considered for analysis and evaluation. Of note, cytokine profiling of EV-containing therapeutic preparations was a novelty, owing to the stringent focus on vesicles.

TABLE 4

Cytokine profiling of UCMSC-derived extracellular vesicle preparations.

| NAME | Condition Standard med./ Ultracentri-fugation | Condition Standard med./TFF | Condition Syn. medium/ Ultracentri-fugation | Condition Syn. medium/ TFF |
|---|---|---|---|---|
| SDF-1 alpha | 1277.7 ± 470.9 | 636.5 ± 367.5 | 183.7 ± 80.4 | 209.3 ± 63.0 |
| IL-27 | 42.9 ± 0.4 | 70.9 ± 3.3 | 11.5 ± 0.1 | 11.5 ± 0.1 |
| IL-1 beta | 3.6 ± 0.1 | 3.7 ± 0.3 | 2.5 ± 0.1 | 2.5 ± 0.0 |
| IL-2 | 201.6 ± 2.1 | 259.7 ± 3.4 | 0.0 | 0.0 |
| IL-5 | 123.0 ± 10.3 | 163.8 ± 35.4 | 0.0 | 0.0 |
| IL-6 | 390.4 ± 6.3 | 1167.5 ± 158.0 | 16.4 ± 16.4 | 144.2 ± 32.7 |
| IL-8 | 302.3 ± 21.0 | 432.2 ± 85.3 | 49.5 ± 10.3 | 82.6 ± 2.6 |
| IL-10 | 7.9 ± 0.2 | 9.5 ± 3.6 | 0.0 | 0.0 |
| Eotaxin | 33.9 ± 0.3 | 44.1 ± 1.3 | 0.0 | 4.4 ± 1.0 |
| IL-1RA | 844.1 ± 70.1 | 754.2 ± 221.3 | 0.0 | 0.0 |
| RANTES | 104.1 ± 0.1 | 109.4 ± 10.5 | 48.8 ± 10.5 | 75.8 ± 5.3 |
| IFN-gamma | 5.6 ± 0.6 | 10.8 ± 1.1 | 0.0 | 0.0 |
| GM-CSF | 58.0 ± 0.2 | 80.3 ± 1.7 | 25.8 ± 0.3 | 27.0 ± 0.7 |
| TNF-alpha | 86.9 ± 6.6 | 108.6 ± 0.0 | 0.0 | 0.0 |
| VEGF-D | 10.9 ± 0.9 | 30.6 ± 3.6 | 0.0 | 0.0 |
| bNGF | 145.1 ± 8.5 | 160.2 ± 34.9 | 0.0 | 0.0 |
| EGF | 37.5 ± 2.7 | 64.8 ± 3.9 | 0.0 | 0.0 |
| BDNF | 125.6 ± 24.7 | 208.6 ± 65.7 | 119.8 ± 93.7 | 230.6 ± 90.1 |
| IL-15 | 59.1 ± 0.7 | 102.8 ± 8.0 | 0.0 | 0.0 |
| PDGF-BB | 35.2 ± 2.5 | 68.1 ± 0.5 | 0.0 | 0.0 |

Median Values:

| | |
|---|---|
| SDF1 | 600 pg/mL |
| IL-6 | 800 pg/mL |
| IL8 | 350 pg/mL |
| GM-CSF | 70 pg/mL |
| BDNF | 170 pg/mL |

BDNF 329 aa

Differential analysis of extracellular-vesicle-associated cytokines revealed a specific enrichment in the neuroprotective cytokine Brain Derived Neurotrophic Factor (BDNF). Enrichment and purification strategies that take advantage of the Tangential Flow System versus conventional ultracentrifugation increase the BDNF content by 70%. BDNF is specifically produced by the therapeutically-active UC-MSCs and packaged into or onto vesicles and is not serum-derived since identical values of BDNF were retained in extracellular-vesicle preparations derived from both HPL containing and serum-free synthetic culture media. The HPL-containing medium was prepared as described above in Example 1 (e.g. section 2.1) and Example 2.

Synthetic medium was prepared by combining the basal TheraPEAK Medium (Lonza) and the supplement (Cat. No.: MSCGM-CD™ Bulletkit 00190632) according to manufacturer's guidelines. Medium was sterile filtered by 0.22 micron filtration. Purification of MSC-derived extracellular vesicles from cells grown in synthetic serum-free medium was conducted as for the standard medium derived extracellular vesicles.

Demonstrated Immunomodulatory Activity

The regenerative and immunomodulatory activity of MSCs is partially mediated by secreted vesicular factors. EVs exocytosed by MSCs are gaining increased attention as prospective non-cellular therapeutics for a variety of diseases. However, the lack of suitable in vitro assays to monitor the therapeutic potential of EVs currently restricts their application in clinical studies.

We have evaluated a dual in vitro immunomodulation potency assay that reproducibly reported the inhibitory effect of MSCs on induced T-cell proliferation and the alloantigen-driven mixed leukocyte reaction of pooled peripheral blood mononuclear cells in a dose-dependent manner. Phytohemagglutinin-stimulated T-cell proliferation was inhibited by MSC-derived EVs prepared by the above described methods in a dose-dependent manner comparable to MSCs. In contrast, inhibition of alloantigen-driven mixed leukocyte reaction was only observed for MSCs, but not for EVs. These results supported an immunomodulatory potential of EVs obtained by the methods of the invention.

TSG-6 Expression and Therapeutic Activity

TSG-6 (277 aa) is a biomarker to predict efficacy of human MSCs in modulating inflammation in vivo. Comparison of hMSCs from a small cohort suggested that hMSCs from female donors compared with male donors were more effective in suppressing inflammation in the cornea model, expressed higher levels of TSG-6. The use of TSG-6 expression as a biomarker could improve selection of the most effective MSCs for clinical trials and overcome some of the variations in patient responses. The clinical trials with human MSCs from bone marrow and other tissues are proceeding even though cultures of the cells are heterogeneous and there is large variability among preparations of hMSCs due to differences among donors, culture conditions, and inconsistent tissue sampling. However, there was currently no in vitro bioassay for the evaluation of hMSC efficacy in vivo. Therefore, the value of the data obtained from current clinical trials may well be compromised by variations in the quality of the hMSCs used. This study provides the first biomarker that can predict the efficacy of hMSCs in suppressing sterile inflammation in vivo (Lee et al., 2014).

We have confirmed the specific enrichment of TSG-6 in umbilical cord MSC-derived extracellular vesicles obtained by the above described methods.

Patellar Tendon Enthesis Defect Model:

The regenerative capacity of the UC-MSC-derived extracellular-vesicles obtained by the methods described above was demonstrated by the treatment of tendon defects (enthesopathies). The UC-MSC-derived extracellular-vesicles were analyzed in to a patellar tendon enthesis defect model in rats. A total of 57 skeletally mature rats (age 3 months; weight approx. 300 grams; Janvier Labs, France) were randomly assigned to 5 groups. Under general anaesthesia a window defect in the patellar tendon (right hind limb) was created using a 2 mm sterile dermal punch (pfm medical, Germany) and the cartilaginous enthesis was thoroughly removed using the punch in order to thoroughly destroy the tendon insertion site. Subsequently, the defect were either left untreated (empty control; n=9), treated with a fibrin clot only (25 µl, TISSEEL; Baxter, Germany), or received fibrin clots loaded with either UC-MSC-derived extracellular-vesicles only (10E6 cell equivalents), 0.5 µg rhuBMP2 only (Peprotech, UK), or a combination of UC-MSC-derived extracellular-vesicles (10E6 cell equivalents) and 0.5 µg rhuBMP2. Subsequently the wound was closed and the animals were allowed to move freely and to immediately load the treated limb. 2 weeks post-surgery the animals were sacrificed, X-Ray analysis was conducted to exclude heterotopic ossification and tissue samples (tibia-patellar tendon-quadriceps muscle) were harvested for biomechanical evaluation using a uniaxial tensile testing regimen (Zwick/Roell, Germany).

For maximum tensile loads no significant differences between the test samples were observed. To the contrary, the stiffness of the samples did differ by trend. Pairwise comparisons between the control group and the treatment groups revealed:

First the defects treated with a combination of UC-MSC-derived extracellular-vesicles and 0.5 µg BMP2 were significantly less stiffer when compared to the control group (p=0.0315; Mann-Whitney test); see FIG. 22 and Table 5. Therefore, the enthesis showed the highest elasticity (flexibility) in case of the defects treated with the extracellular vesicles of the invention and BMP2. An increased elasticity/flexibility prevents further defects, e.g. the rupture of the tendon, in particular the tendon enthesis.

Second, the median values of the defects treated with UC-MSC-derived extracellular-vesicles alone were lower by trend when compared to the control group.

TABLE 5

Stiffness of specimens 2 weeks post-surgery

| | Stiffness (N/mm) | | | |
|---|---|---|---|---|
| | control | EVs | rhuBMP2 | rhuBMP + EVs |
| n | 9.0 | 8.0 | 9.0 | 9.0 |
| Minimum | 77.2 | 52.6 | 68.4 | 50.7 |
| 25% Percentile | 90.6 | 61.6 | 76.6 | 52.7 |
| Median | 95.3 | 78.5 | 90.0 | 74.5 |
| 75% Percentile | 128.1 | 118.3 | 101.6 | 95.6 |
| Maximum | 160.0 | 139.4 | 126.6 | 98.0 |

REFERENCES

Al-Saqi, S. H. et al. Cytotherapy 16, 915-26 (2014)

Arroyo, J. D. et al. Proc Natl Acad Sci USA. 108, 5003-5008 (2011)

Baglio, S. R., Pegtel, D. M. & Baldini, N. Frontiers in Physiology 3, 359 (2012)

Baglio, S. R. et al. Stem Cell Research & Therapy, 6, 127 (2015)

Balaj, L. et al. Sci Rep. 5, 10266 (2015)

Beer, L. et al. Apoptosis 12, 1336-1353 (2016)

Betz, O. B. et al. Tissue Engineering. Part A 16, 1093-1101 (2010)

Bi, Y. et al. Nature Medicine 13, 1219-1227 (2007)

Bonnet N. et al. Mol. Cell Endocrinology 432, 75-82 (2016)

Burger, D. et al. The American Journal of Pathology 185, 2309-2323 (2015)

Burnout, T. et al. Biomaterials 76, 371-387 (2016)

Chassin, C., et al. Cell Host Microbe 8, 358-368 (2010)

Crescitelli, R. et al. J Extracell Vesicles. 2 (2013)

Dale, G. L. et al. Platelets 20, 361-6 (2009)

Dawson, J. I. et al. Stem Cells 32, 35-44 (2014)

De Jong, O. G. et al. Frontiers in Immunology 5, 608 (2014)

Delandre, C. et al. Exp Cell Res. 315, 1953-1963 (2009)

Docheva D, et al.; Adv Drug Deliv Rev. 84:222-39 (2015)

Doeppner, T. R. et al. Stem Cells Translational Medicine 4, 1131-1143 (2015)

Dominici, M. et al. Cytotherapy 8, 315-317 (2006)

Dowthwaite, G. P. et al. J Cell Sci 117, 889-897 (2004)

Eguchi, T. et al. PLOS one 8, e58796

Einhorn, T. A. et al. J Bone Joint Surg Am 66, 274-279 (1984)

Eitan, E. et al. J Extracell Vesicles. 4, 26373 (2015)
E L Andaloussi, S. et al. Nat Rev Drug Discov. 12, 347-357 (2013)
Gambim, M. H. et al. Crit Care 1, R107 (2007).
Gangoda, L. et al. Proteomics 15, 260-271 (2015)
Gardiner, C. et al. Journal of Extracellular Vesicles 5, 32945 (2016)
Glatt, V. et al. J Bone Joint Surg Am. 20; 98(8):677-87 (2016)
Gomez-Barrena, E. et al. Journal of Cellular and Molecular Medicine 15, 1266-1286 (2011)
Gould, S. J. & Raposo, G. J Extracell Vesicles 2, 20389 (2013)
Haider, T. et al. Experimental Neurol. 267, 2302-42 (2015)
Heinemann, M. L. et al. J Chromatogr A. 1371, 125-135 (2014)
Hemeda, H. et a. Cytotherapy 0.16, 170-180 (2014)
Hou, C. et al. Molecular Medicine Reports 12, 4877-4886 (2015)
Hu, G. W. et al. Stem Cell Research & Therapy 6, 10 (2015)
Huang, S. et al. Stem Cells and Development 21, 2531-2540 (2012)
Jiang, Z. Z. et al. Stem Cell Research & Therapy 7, 24 (2016)
Kalomoiris, S. et al. J. Cellular Biochemistry 117, 2128-2137 (2016)
Kang, H. and Hata, A. BMB Reports 48, 319-326, (2015)
Katagiri T, Cold Spring Harb Perspect Biol. 8(6). pii: a021899 (2016)
Keramaris, N. C. et al. Injury 39 Suppl 2, S45-57, (2008)
Ketterl, N. et al. Stem Cell Res Ther. 6, 236 (2015)
Kim, J. W. et al. Ann Hematol 83, 733-738 (2004)
Klatte-Schulz F, et al.; Sci Rep. 11; 6:29703 (2016)
Kozasa, T. et al. Biologicals. 39, 242-248 (2011)
Kunkel, N. et al. Journal of Tissue Engineering and Regenerative Medicine (2015)
Lai, R. C. et al. J Extracell Vesicles. 5, 29828 (2016)
Laner-Plamberger, S. et al. Journal of Translational Medicine 13, 354 (2015)
Li, L. et al. J. Cell. Biochem. 113, 1235-1244 (2012)
Li, J. et al. J Extracell Vesicles 4, 26883 (2015)
Liu, X. Y. et al. Am J Cancer Res. 5, 2569-2589 (2015)
Liu, J. et al. Biomaterials 52, 148-60 (2015)
Lin, T. M. et al. Biochem. Biophys. Res. Commun. 361, 883-889 (2007)
Linares, R. et al. Journal of Extracellular Vesicles 4, 29509 (2015)
Lotvall, J. et al. J Extracell Vesicles. 3, 26913 (2014)
Lu, L.-F. et al. Cell 142, 914-929 (2010)
Mackensen, A. et al. Cancer Immunol Immunother. 49, 152-156 (2000)
Maji, S. et al. J. Applied Toxicol. DOI 10.1002/ja.3362 (2016)
Mulcahy, L. A. et. al. Journal of Extracellular Vesicles 3, 24641 (2014)
Morita, T. et al. Neuroscience 335, 221-231 (2016)
Mulisch, M. et al. Spektrum Akademischer Verlag, (2010)
Nakamura, Y. et al. FEBS Left 589, 1257-1265 (2015)
Nikfarjam, L. & Farzaneh, P. Cell J. 13, 203-212 (2012)
Nordin, J. Z. et al. J Extracell Vesicles 4, 26316 (2015)
Nuttall, P. A. et al. Nature 266, 835-837 (1977)
Park et al. J. Biol. Chem. 290, 2831-2841 (2015)
Raposo, G. & Stoorvogel, W. J Cell Biol. 200, 373-383 (2013)
Ratajczak, M. Z. et al. Clinical and Translational Medicine 7 (2016)
Reyes, J. M. et al. Stem Cells 24, 1213-1217 (2006)

Rosset, P., Deschaseaux, F. & Layrolle, P. Orthop Traumatol Surg Res 100, S107-112 (2014)
Salingcarnboriboon, R. et al. Exp Cell Res 287, 289-300 (2003)
Schallmoser, K. et al. Transfusion 47, 1436-1446 (2007)
Schallmoser, K. et al. Biomed Mater Eng. 19, 271-276 (2009)
Schmidt-Bleek, K., et al. Cytokine & Growth Factor Reviews 27, 141-148 (2016)
Selvaggi, T. A. et al. Blood. 89, 776-779 (1977)
Seo, B. M. et al. Lancet 364, 149-155 (2004)
Shelke, G. V. et al. J Extracell Vesicles 3, 24783 (2014)
So, A. Y-L. et al Immunological Reviews 253, 129-145 (2013)
Steinmann, J. C. & Herkowitz, H. N. Clin Orthop Relat Res, 80-90 (1992)
Swamynathan, P. et al. Stem Cell Res Ther. 5, 88 (2014)
Tempfer, H. et al. Histochemistry and Cell Biology 131, 733-741 (2009)
Thery, C. et al. Curr Protoc Cell Biol. Chapter 3: Unit 3.22. (2006)
Tonti, G. A. & Mannello, F. Int J Dev Biol. 52, 1023-1032 (2008)
Torreggiani, E. et al. Eur Cell Mater. 28, 137-151 (2014)
Tuschong, L. et a. Hum Gene Ther. 13, 1605-10 (2002)
van der Pol, E. et al. J Thromb Haemost. (2016)
Vickers, K. C. et al. Nat Cell Biol. 13, 423-433 (2011)
Walker, J. T. et al. Cell Tissue Research DOI 10.1007/s00441-016-2426-6 (2016)
Wang, J. H. et al. Osteoarthritis and Cartilage 21, 1987-1996 (2913)
Wang, X. et al. Hypertension 66, 776-785 (2015)
Wei, J. et al. Stem Cells and Development 23, 1452-1463 (2014)
Wright, K. T. et al. Stem Cells 2, 169-178 (2011)
Xin, H., Li, Y. & Chopp, M. Frontiers in Cellular Neuroscience 8, 377 (2014)
Yan, S. et al. J. Cellular Biochemistry 116, 1680-1692 (2015)
Yasko A W, et al. J Bone Joint Surg Am. 74(5):659-70 (1992)
Yeh, C.-H. et al. The Spine Journal 16, 896-904 (2916)
Yoshimura, H. et al. Cell Tissue Res 327, 449-462 (2007)
Yu, B. et al. Int J Mol Sci. 15, 4142-4157 (2014)
Zhang, B. et al. Stem Cells and Development 23, 1233-1244 (2014)
Note for guidance on minimising the risk of transmitting animal spongiform encephalopathy agents via human and veterinary medicinal products (EMA/410/01 rev.3). Official Journal of the European Union. 2011; C 73/01.

The invention claimed is:

1. A pharmaceutical composition, comprising extracellular-vesicles derived from mesenchymal stromal cells (MSCs), wherein the extracellular-vesicles comprise at least about 80%, 85%, 90%, 94.4%, 95%, 99% or 99.5% of extracellular vesicles derived from the MSCs, wherein the extracellular-vesicles are essentially free of heparin, wherein the pharmaceutical composition of the extracellular vesicles is/are in a scaffold, wherein the pharmaceutical composition comprises Bone Morphogenic Protein 2 (BMP2), wherein said BMP2 is at a dose of from 375 μg to 900 μg, wherein the extracellular-vesicles are at a dose of from $1\times10^7$ to $1\times10^{12}$ particles, wherein the MSCs are umbilical cord-derived mesenchymal stromal cells (UC-MSCs), wherein the extracellular vesicles are positive for CD9, CD81 and TSG101 and are negative for GM130, wherein the MSCs are positive for surface markers CD73, CD90 and CD105 and negative for surface markers CD14, CD19, CD34, CD45 and HLA-DR, and wherein the extracellular-vesicles comprise hsa-miR-146a-5p, hsa-miR-92a-3p, hsa-miR-21-5p, hsa-miR-148a-3p, hsa-miR-221-3p, hsa-let-7i-5p, and hsa-let-7f-5p.

2. A pharmaceutical composition, comprising extracellular-vesicles derived from mesenchymal stromal cells (MSCs), wherein the extracellular-vesicles comprise at least about 80%, 85% 90% 94.4%, 95%, 99% or 99.5% of extracellular-vesicles derived from the MSCs, wherein the extracellular-vesicles are essentially free of heparin, wherein the pharmaceutical composition or the extracellular vesicles is/are in a scaffold, wherein the pharmaceutical composition comprises Bone Morphogenic Protein 2 (BMP2), wherein said BMP2 is at a dose of from 375 μg to 900 μg, wherein the extracellular-vesicles are at a dose of from $1\times10^{7}$ to $1\times10^{12}$ particles, wherein the MSCs are umbilical cord-derived mesenchymal stromal cells (UC-MSCs), wherein the extracellular vesicles are positive for CD9, CD81 and TSG101 and are negative for GM130, wherein the MSCs are positive for surface markers CD73, CD90 and CD105 and negative for surface markers CD14, CD19, CD34, CD45 and HLA-DR, and wherein the extracellular-vesicles are essentially free of hsa-miR-133, hsa-miR-135, hsa-miR-204, hsa-miR-211, hsa-miR-17, and hsa-miR-106.

3. A pharmaceutical composition, comprising extracellular-vesicles derived from mesenchymal stromal cells (MSCs), wherein the extracellular-vesicles comprise at least about 80%, 85%, 90%, 94.4%, 95%, 99% or 99.5% of extracellular-vesicles derived from the MSCs, wherein the extracellular-vesicles are essentially free of heparin, wherein the pharmaceutical composition or the extracellular vesicles is/are in a scaffold, wherein the pharmaceutical composition comprises Bone Morphogenic Protein 2 (BMP2), wherein said BMP2 is at a dose of from 375 μg to 900 μg, wherein the extracellular-vesicles are at a dose of from $1\times10^{7}$ to $1\times10^{12}$ particles, wherein the MSCs are umbilical cord-derived mesenchymal stromal cells (UC-MSCS), wherein the extracellular vesicles are positive for CD9, CD81 and TSG101 and are negative for GM130, wherein the MSCs are positive for surface markers CD73, CD90 and CD105 and negative for surface markers CD14, CD19, CD34, CD45 and HLA-DR, and wherein the extracellular-vesicles comprise:

100% of hsa-miR-146a-5p, less than about 0.1% hsa-miR-133, less than about 0.1% hsa-miR-135, less than about 0.1% hsa-miR-204, less than about 0.1% hsa-miR-211, less than about 0.1% hsa-miR-17, and less than about 0.1% hsa-miR-106, wherein the level of hsa-miR-146a-5p is set to 100%.

4. A pharmaceutical composition, comprising extracellular-vesicles derived from mesenchymal stromal cells (MSCs), wherein the extracellular-vesicles comprise at least about 80%, 85%, 90%, 94.4%, 95%, 99% or 99.5% of extracellular-vesicles derived from the MSCs, wherein the extracellular-vesicles are essentially free of heparin, wherein the pharmaceutical composition or the extracellular vesicles is/are in a scaffold, wherein the pharmaceutical composition comprises Bone Morphogenic Protein 2 (BMP2), wherein said BMP2 is at a dose of from 375 μg to 900 μg, wherein the extracellular-vesicles are at a dose of from $1\times10^{7}$ to $1\times10^{12}$ particles, wherein the MSCs are umbilical cord-derived mesenchymal stromal cells (UC-MSCs) and wherein the extracellular-vesicles comprise:

100% of hsa-miR-146a-5p, at least about 50% of hsa-miR-92a-3p, at least about 15% of hsa-miR-21-5p, at least about 10% of hsa-miR-148a-3p, at least about 15% of hsa-miR-221-3p, at least about 5% of hsa-let-7i-5p, and at least about 5% of hsa-let-7f-5p, wherein the level of hsa-miR-146a-5p is set to 100%.

5. A pharmaceutical composition, comprising extracellular-vesicles derived from mesenchymal stromal cells (MSCs), wherein the extracellular-vesicles comprise at least about 80%, 85%, 90%, 94.4%, 95%, 99% or 99.5% of extracellular-vesicles derived from the MSCs, wherein the extracellular-vesicles are essentially free of heparin, wherein the pharmaceutical composition or the extracellular vesicles is/are in a scaffold, wherein the pharmaceutical composition comprises Bone Morphogenic Protein 2 (BMP2), wherein said BMP2 is at a dose of from 375 μg to 900 μg, wherein the extracellular-vesicles are at a dose of from $1\times10^{7}$ to $1\times10^{12}$ particles, wherein the MSCs are umbilical cord-derived mesenchymal stromal cells (UC-MSCs), wherein the extracellular-vesicles comprise:

100% of hsa-miR-146a-5p, at least about 50% of hsa-miR-92a-3p, at least about 15% of hsa-miR-21-5p, at least about 10% of hsa-miR-148a-3p, at least about 15% of hsa-miR-221-3p, at least about 5% of hsa-let-7i-5p, and at least about 5% of hsa-let-7f-5p, wherein the level of hsa-miR-146a-5p is set to 100%, wherein the extracellular vesicles are positive for CD9, CD81 and TSG101 and are negative for GM130, wherein the MSCs are positive for the surface markers CD73, CD90 and CD105, and optionally wherein the MSCs are negative for the surface markers CD14, CD19, CD34, CD45 and HLA-DR.

* * * * *